US011845954B2

(12) United States Patent
Buchholz et al.

(10) Patent No.: US 11,845,954 B2
(45) Date of Patent: Dec. 19, 2023

(54) METHODS AND MEANS FOR GENETIC ALTERATION OF GENOMES UTILIZING DESIGNER DNA RECOMBINING ENZYMES

(71) Applicant: TECHNISCHE UNIVERSITÄT DRESDEN, Dresden (DE)

(72) Inventors: Frank Buchholz, Dresden (DE); Martin Schneider, Dresden (DE); Felix Lansing, Dresden (DE)

(73) Assignee: TECHNISCHE UNIVERSITÄT DRESDEN, Dresden (DE)

( * ) Notice: Subject to any disclaimer, the term of this patent is extended or adjusted under 35 U.S.C. 154(b) by 913 days.

(21) Appl. No.: 16/622,937

(22) PCT Filed: Jun. 14, 2018

(86) PCT No.: PCT/EP2018/065881
§ 371 (c)(1),
(2) Date: Dec. 16, 2019

(87) PCT Pub. No.: WO2018/229226
PCT Pub. Date: Dec. 20, 2018

(65) Prior Publication Data
US 2021/0147878 A1 May 20, 2021

(30) Foreign Application Priority Data
Jun. 14, 2017 (EP) .................................... 17175895

(51) Int. Cl.
C12N 15/90 (2006.01)
C12N 9/22 (2006.01)
C12N 15/10 (2006.01)
C12Q 1/6869 (2018.01)
C12N 9/00 (2006.01)
C12N 9/12 (2006.01)

(52) U.S. Cl.
CPC ............. *C12N 15/907* (2013.01); *C12N 9/22* (2013.01); *C12N 15/1058* (2013.01); *C12Q 1/6869* (2013.01)

(58) Field of Classification Search
None
See application file for complete search history.

(56) References Cited

U.S. PATENT DOCUMENTS

| 4,861,719 | A  | 8/1989  | Miller          |
|-----------|----|---------|-----------------|
| 5,278,056 | A  | 1/1994  | Bank et al.     |
| 5,882,877 | A  | 3/1999  | Gregory et al.  |
| 5,981,830 | A  | 11/1999 | Wu et al.       |
| 6,013,516 | A  | 1/2000  | Verma et al.    |
| 6,774,279 | B2 | 8/2004  | Dymecki         |
| 7,422,889 | B2 | 9/2008  | Sauer et al.    |
| 7,915,037 | B2 | 3/2011  | Sauer et al.    |
| 8,645,115 | B2 | 2/2014  | Collins et al.  |
| 8,697,359 | B1 | 4/2014  | Richter et al.  |
| 10,017,832 | B2 | 7/2018 | Havranek et al. |
| 10,316,301 | B2 | 6/2019 | Hauber et al.   |
| 10,344,301 | B2 | 7/2019 | Ghadessy et al. |
| 10,392,674 | B2 | 8/2019 | Liu et al.      |
| 11,078,493 | B2 | 8/2021 | Makhija et al.  |
| 11,104,967 | B2 | 8/2021 | Liu et al.      |
| 2003/0082723 | A1 | 5/2003 | Altmann et al. |
| 2004/0003435 | A1 | 1/2004 | Baszczynski et al. |
| 2009/0217400 | A1 | 8/2009 | Carmi et al.   |
| 2013/0164271 | A1* | 6/2013 | Hauber ................ C12N 9/1241 435/348 |
| 2015/0093802 | A1 | 4/2015 | McCray et al.  |
| 2017/0058297 | A1 | 3/2017 | Havranek et al. |
| 2018/0355381 | A1 | 12/2018 | Hangzhou et al. |

FOREIGN PATENT DOCUMENTS

| EP | 0220009  | A2 | 4/1987  |
|----|----------|----|---------|
| EP | 1288295  | A2 | 3/2003  |
| EP | 1032680  | B1 | 2/2006  |
| EP | 1214440  | B1 | 6/2006  |
| EP | 1751180  | A2 | 2/2007  |
| EP | 1681355  | B1 | 10/2009 |

(Continued)

OTHER PUBLICATIONS

Bolusani et al., "Evolution of variants of yeast site-specific recombinase Flp that utilize native genomic sequences as recombination target sites", Nucleic Acid Research, Sep. 20, 2006, 34(18): 5259-5269.
Buchholz et al., "Alteration of Cre recombinase site specificity by substrate-linked protein evolution", Nature Biotechnology 19(11):1047-1052, 2001.
Chen et al., "Fusion Protein Linkers: Property, Design, and Functionality", Adv. Drug Deliv. Rev. 65(10):1357-1369, 2013.
European Search Report for European Patent Application No. 18731446.3, dated Mar. 5, 2021.
European Examination Report for European Patent Application No. 18731446.3, dated Feb. 11, 2022.
Gelato et al., "Spatially Directed Assembly of a Heterotetrameric Cre-Lox Synapse Restricts Recombination Specificity", J. Mol. Biol., 2008, 378(3): 653-665.

(Continued)

Primary Examiner — Suzanne M Noakes
Assistant Examiner — Jae W Lee
(74) Attorney, Agent, or Firm — LATHROP GPM LLP; James H. Velema, Esq.; Michael Spellberg, Esq.

(57) ABSTRACT

The invention provides methods for specifically altering the DNA sequence in a genome, in particular for genome editing by deleting or replacing a sequence of interest. Advantageously, the invention uses two non-identical sequences naturally occurring in a genome as target sites two which DNA-recombining enzymes are generated. The invention is in particular useful for medicine, in particular to repair a mutation in a genome or to delete predefined genetic material from cells or tissue and to cure diseases. An advantage of the invention is that it allows precise site directed altering of DNA without engaging host DNA repair pathways and thereby works without inducing random insertions and deletions (indels).

12 Claims, 23 Drawing Sheets
Specification includes a Sequence Listing.

(56) References Cited

FOREIGN PATENT DOCUMENTS

| EP | 2094855 B1 | 2/2012 |
|---|---|---|
| EP | 2590676 A2 | 5/2013 |
| EP | 2576798 B1 | 4/2016 |
| EP | 3115064 A1 | 1/2017 |
| EP | 3290518 A1 | 3/2018 |
| EP | 3831939 A1 | 6/2021 |
| WO | WO 1994/019478 A1 | 9/1994 |
| WO | WO 1995/014785 A1 | 6/1995 |
| WO | WO 1996/022378 A1 | 7/1996 |
| WO | WO 1999/025840 A1 | 5/1999 |
| WO | WO 1999/025841 A1 | 5/1999 |
| WO | WO 2001/016345 A2 | 3/2001 |
| WO | WO 2002/044409 A2 | 6/2002 |
| WO | WO 2005/081632 A2 | 9/2005 |
| WO | WO 2008/083931 A1 | 7/2008 |
| WO | WO 2009/007982 A1 | 1/2009 |
| WO | WO 2010/143606 A1 | 12/2010 |
| WO | 2011147590 | 12/2011 |
| WO | WO 2011/147590 A2 | 12/2011 |
| WO | WO 2012/006376 A2 | 1/2012 |
| WO | WO 2016/034553 A1 | 3/2012 |
| WO | WO 2012/088381 A1 | 6/2012 |
| WO | WO 2014/016248 A1 | 1/2014 |
| WO | WO 2014/093330 A1 | 6/2014 |
| WO | WO 2014/134412 | 9/2014 |
| WO | WO 2016/022075 A1 | 2/2016 |
| WO | WO 2016/089866 A1 | 6/2016 |
| WO | WO 2017/015545 A1 | 1/2017 |
| WO | WO 2018/031683 A1 | 2/2018 |
| WO | WO 2018/229226 A1 | 12/2018 |
| WO | WO 2021/015997 A1 | 2/2021 |
| WO | WO 2021/110846 A1 | 6/2021 |
| WO | WO 2021/158651 A1 | 8/2021 |
| WO | WO 2021/204807 A1 | 10/2021 |
| WO | WO 2021/207401 A1 | 10/2021 |

OTHER PUBLICATIONS

Hoersten et al., "Pairing of single mutatuins yield obligate Cre-type site-specific recombinases", Nucleic Acids Res., 2022, 50(2): 1174-1186.

International Search Report and Written Opinion for PCT International Patent Application No. PCT/EP2018/065881, dated Aug. 6, 2018.

International Search Report and Written Opinion for PCT International Patent Application No. PCT/EP2020/084489, dated Feb. 23, 2021.

Karpinski et al., "Directed evolution of a recombinase that excises the provirus of most HIV-1 primary isolates with high specificity(incl Online Methods)", Nature Biotechnology, Apr. 2016, 34(4): 401-409 +4 pages online methods, DOI: 10.1038/nbt.3467.

Karpinski et al., "Designer-Rekombinasen für präzises Genome Editing", BIOspektrum, 2017, 23(2):151-154.

Konieczka et al., "Recombination of Hybrid Target Sites by Binary Combinations of Flp Variants: Mutations that Foster Interprotomer Collaboration and Enlarge Substrate Tolerance", J. Mol. Biol., 2004, 339(2): 365-378.

Lansing et al., "Correction of a Factor VIII genomic inversion with designer-recombinases", Nat Commun., 2022, 13: 422.

Surendranath et al., "SeLOX—a locus of recombination site search tool for the detection and directed evolution of site-specific recombination systems", Nucleic Acids Research, Jul. 2010, 38(Web Server Issue): W293-W298.

Wang et al., "Efficient delivery of genome-editing proteins using bioreducible lipid nanoparticles", PNAS, 2016, 113: 2868-2873.

Zhang et al., "Redesign of the monomer-monomer interface of Cre recombinase yields an obligate heterotetrameric complex", Nucleic Acids Res., 2015, 41(18): 9076-9085.

S. Bolusani et al: Evolution of variants of yeast site-specific recombinase Flp that utilize native genomic sequences as recombination target sites, Nucleic Acid Research. vol. 34. No. 18, Sep. 20, 2006, pp. 5259-5269.

Karpinski Janet et al: "Directed evolution of a recombinase that excises the provirus of most HIV-1 primary isolates with high specificity (incl Online Methods)", Nature Biotechnology, vol. 34, No. 4, Apr. 2016, pp. 401-409 +4pp.

Surendranath Vineeth et al: "SeLOX—a locus of recombination site search tool for the detection and directed evolution of site-specific recombination systems." Nucleic Acids Research, vol. 38, No. Web Server Issue, Jul. 2010, pp. W293-W298.

Karpinski Janet et al: "Designer-Rekombinasen fur prazisesGenome Editing", Biospektrum, vol. 23, No. 2, Mar. 29, 2017, pp. 151-154.

Konieczka J H et al: "Recombination of Hybrid Target Sites by Binary Combinations of Flp Variants: Mutations that Foster Interprotomer Collaboration and Enlarge Substrate Tolerance", Journal of Molecular Bio, vol. 339, No. 2, May 28, 2004, pp. 365-378.

U.S. Appl. No. 18/046,066, filed Oct. 22, 2022, Frank Buchholz, Methods and Means for Genetic Alteration of Genomes Utilizing Designer DNA Recombining Enzymes.

U.S. Appl. No. 17/780,136, filed May 26, 2022, Frank Buchholz, Fusion of Site-Specific Recombinases for Efficient and Specific Genome Editing.

U.S. Appl. No. 18/055,545, filed Nov. 15, 2022, Jenna Hoersten, Site Specific Recombinases for Efficient and Specific Genome Editing.

Abi-Ghanem et al., "Engineering of a target site-specific recombinase by a combined evolution- and structure-guided approach", Nucleic Acids Res., Dec. 28, 2012, 41(4): 2394-2403.

Abi-Ghanem et al., "Insights into the preferential order of strand exchange in the Cre/loxP recombinase system: impact of the DNA spacer flanking sequence and flexibility", J Comput Aid Mol Des., Mar. 2015, 29(3): 271-282.

Anastassiadis et al., "Gene Targeting and Site-Specific Recombination in Mouse ES Cells", Methods Enzymol, 2013, 533: 133-155.

Carroll, "Genome engineering with targetable nucleases. Annual Review of Biochemistry", Annual Review of Biochem., Jun. 2014, 83: 409-439.

Chandras et al., "CreZOO—the European virtual repository of Cre and other targeted conditional driver strains", Jun. 21, 2012, Database, 2012: bas029.

Chen et al., "Characterization of 582 natural and synthetic terminators and quantification of their design constraints", Nat. Methods, Jun. 2, 2013, 10: 659-664.

Cox et al., "Therapeutic Genome Editing: Prospects and Challenges", Nature Medicine, Feb. 2015, 21(2): 121-131.

Cyranoski, "CRISPR gene-editing tested in a person for the first time", Nature, Nov. 24, 2016, 539(7530): 479.

Duyne, "Cre Recombinase", Microbiol. Spectr., Feb. 2015, 3(1), 119-138.

Esposito et al., "The integrase family of tyrosine recombinases: evolution of a conserved active site domain", Nucleic Acids Res., Sep. 15, 1997, 25(18): 3605-3614.

Extended European Search Report for European Patent Application No. 21208214.3, dated May 11, 2022.

Gibb et al., "Requirements for catalysis in the Cre recombinase active site", Nucleic Acids Res., May 12, 2010, 38(17): 5817-5832.

Hauber et al., "Highly Significant Antiviral Activity of HIV-1 LTR-Specific Tre-Recombinase in Humanized Mice", Plos. Pathog., Sep. 2013, 9(9): e1003587.

He et al., "Enhancing the precision of genetic lineage tracing using dual recombinases", Nat Med, Dec. 2017, 23(12): 1488-1498.

Herman et al., "Incorporating Synthetic Oligonucleotides via Gene Reassembly (ISOR): a versatile tool for generating targeted libraries", Protein Eng., Des., & Sel., May 5, 2007, 20(5): 219-226.

International Search Report and Written Opinion for PCT International Patent Application No. PCT/EP2022/081868, dated Mar. 3, 2023.

Karimova et al., "Vika/vox, a novel efficient and specific Cre/loxP-like site-specific recombination system", Nucleic Acids Res, Jan. 2013, 41(2): e37-e37.

Kosicki et al., "Repair of double-strand breaks induced by CRISPR-Cas9 leads to large deletions and complex rearrangements", Nature Biotechnology, 2018, 36: 765-771.

(56) References Cited

OTHER PUBLICATIONS

Lannoy et al., "Principles of genetic variations and molecular diseases: applications in hemophilia A", Crit Rev Oncol Hemat, Aug. 2016, 104: 1-8.
Lansing et al., "Wie Designer-Rekombinasen Erbkrankheiten heilen könnten", BioSpektrum, Mar. 23, 2021, 27(2): 139-141.
Lansing et al., "A heterodimer of evolved designer-recombinases precisely excises a human genomic DNA locus", Nucleic Acids Res., Jan. 19, 2020, 48(1): 472-485.
Lapique et al., "Digital switching in a biosensor circuit via programmable timing of gene availability", Nat Chem Biol, Oct. 14, 2014, 10: 1020-1027.
Luo et al., "Small-molecule control of protein function through Staudinger reduction", Nat. Chem., Nov. 2016, 8(11): 1027-1034.
Martin et al., "Modulation of the Active Complex Assembly and Turnover Rate by Protein-DNA Interactions in Cre-LoxP Recombination", Biochemistry, Jun. 14, 2003, 42(22): 6814-6826.
Meinke et al., "Cre Recombinase and Other Tyrosine Recombinases", Chemical reviews, Oct. 26, 2016, 116(20): 12785-12820.
Monetti et al., "PhiC31 integrase facilitates genetic approaches combining multiple recombinases", Methods, Apr. 2011, 53(4), 380-385.
Murray et al., "Beyond knockouts: cre resources for conditional mutagenesis", Mamm Genome, Oct. 2012, 23(0): 587-599.
Oldenburg et al., "Historical Review on Genetic Analysis in Hemophilia A", Seminars Thrombosis Hemostasis, Nov. 2014, 40(8): 895-902.
Park et al., "Functional Correction of Large Factor VIII Gene Chromosomal Inversions in Hemophilia A Patient-Derived iPSCs Using CRISPR-Cas9", Cell Stem Cell, Aug. 6, 2015, 17(2): 213-220.
Petyuk et al., "Functional Mapping of Cre Recombinase by Pentapeptide Insertional Mutagenesis", J Biol Chem, Aug. 27, 2004, 279(35): 37040-37048.
Qasim et al., "First Clinical Application of Talen Engineered Universal CAR19 T Cells in B-ALL", Blood, 2015, 126(23): 2046.
Saraf-Levy et al., "Site-specific recombination of asymmetric lox sites mediated by a heterotetrameric Cre recombinase complex", Bioorgan. Med. Chem., May 1, 2006, 14(9): 3081-3089.
Sarkar et al., "HIV-1 Proviral DNA Excision Using an Evolved Recombinase", Science, Jun. 29, 2007, 316(5833): 1912-1915.
Shah et al., "Target-specific variants of Flp recombinase mediate genome engineering reactions in mammalian cells", Febs J., Sep. 2015, 282(17): 3323-3333.
Soni et al., "Nearest-neighbor amino acids of specificity-determining residues influence the activity of engineered Cre-type recombinases", Aug. 19, 2020, Sci. Rep., 10: 13985.
Tebas et al., "Gene editing of CCR5 in autologous CD4 T cells of persons infected with HIV", The New England Journal of Medicine, Mar. 6, 2014, 370(10): 901-910.
Wang et al., "Non-viral delivery of genome-editing nucleases for gene therapy", Gene Therapy, Mar. 2017, 24(3): 144-150.
Yamanashi et al., "A Modified Cre-lox Genetic Switch to Dynamically Control Metabolic Flow in *Saccharomyces cerevisiae*", Acs Synth Biol, Feb. 7, 2012, 1(5): 172-180.

\* cited by examiner

| Recombinase | Sequence alignment | SEQ ID No. |
|---|---|---|
| Cre | MSNLLTVHQNLPALPVDATSDEVRKNLMDMFRDRQAFSEHTWKMLLSVCRSWAAWCKLNN 60 | 39 |
| R#1 | MSKLQTIHQNLSAILVDATSDEARKNLMDVIRDRQAFSKHTWRVLLSVCRSWAAWCELNN 60 | 34 |
| R#7-B5 | MSKLQTIHQDLSAILVDVTSDEARKNLMDVIRDRQAFSKHTWRVLLSVCRSWAAWCELNN 60 | 35 |
| F9-3 | MDKLQTIHQDLSAILVDVTSDEARKNLMDVIRDRQAFSRHTWRVLLSVCRSWAAWCELNN 60 | 36 |
| | * :*:**:* :*   *:*** :*:*:***********:* | |
| Cre | RKWFPAEPEDVRDYLLYLQARGLAVKTIQQHLGQLNMLHRRSGLPRPSDSNAVSLVMRRI 120 | 39 |
| R#1 | RKWFPAEPEDVRDYLLHLQTRGLIFVNTIQQHLCPLNLLHRRSGLPRPGDSNAVSLVMRRI 120 | 34 |
| R#7-B5 | RKWFPAEPEDVRDYLLHLQTRGLIHTIFVNTIQQHLCPLNLLHRRSGLPRPGDSNAVSLVMRRI 120 | 35 |
| F9-3 | RKWFPAEPEDVRDYLLQLQTRGLIEVNTIQQHLCPLNLLHRRSGLPRPGDSNAVSLVMRRI 120 | 36 |
| | **************:* ** *: ****  *****.****** | |
| Cre | RKENVDAGERAKQALAFERTDFDQVRSLMENSDRCQDIRNLAFLGIAYNTLLRLAEIARI 180 | 39 |
| R#1 | RKENIDAGERVKQALAFERTDFDQVRSLMENSDRCQDIRNLAFLGVAYNTLLRISEIARI 180 | 34 |
| R#7-B5 | RKENIDAGERVKQALAFERTDFDQVRSLMENSDRCQDIRNLAFLGVAYNTLLRISEIARI 180 | 35 |
| F9-3 | RKENIDAGERVKQALAFERTDFDQVRSLMENSDRCQDIRNLAFLGVAYNTLLRISEIARI 180 | 36 |
| | **:*.*************************:***::*** | |
| Cre | RVKDISRTDGGRMLIHIGRTKTLVSTAGVEKALSLGVTKLVERWISVSGVADDPNNYLFC 240 | 39 |
| R#1 | RVRDIRTDGGRMLIHIGRTKTLVSAAGVEKALSLGVTKLVERWISVSGVADDPNNYLFC 240 | 34 |
| R#7-B5 | RVRDIRTDGGRMLIHIGRTKTLVSAAGVEKALSLGVTKLVERWISVSGVADDPNNHLFC 240 | 35 |
| F9-3 | RVRDIRTDGGRMLIHIGITKTLVSAAGVEKALSLGVTKLVERWISVSGVADDPNNHLFC 240 | 36 |
| | :.********** * .********************* :* | |
| Cre | RVRKNGVAAPSATSQLSTRALEGIFEATHRLIYGAKDDSGQRYLAWSGHSARVGAARDMA 300 | 39 |
| R#1 | RVRRNGVAAPSATSQLSTPALQGVFAAAHRLIHGAKDASGQRYITWSGHSARVGAARDMA 300 | 34 |
| R#7-B5 | RVRRNGVAAPSAISQLSTPALQGVFAAAHRLIHGAKDASGQRYITWSGHSARVGAARDMA 300 | 35 |
| F9-3 | RVRRNGVAAPSAISQLSTPALQGVFAAAHRLIHGAKDDSGQRYITWSGHSARVGAARDMA 300 | 36 |
| | :*****.*  : :.* ********** | |
| Cre | RAGVSIPEIMQAGGWTNVNIVMNYIRNLDSETGAMVRLLEDGD- 343 | 39 |
| R#1 | RAGVSVAEIMQAGGWTTVESVMNYLRNLDSETGAMVRLLEDGD* 343 | 34 |
| R#7-B5 | RAGVSVAEIMQAGGWTTVESVMNYLRNLDSETGAMVRLLEDGD* 343 | 35 |
| F9-3 | RAGVEAEIMQAGGWTTVESVMSYLRNLDSETGAMVRLLEDGD* 343 | 36 |
| | **** ********** *:**.*:***************** | |

Fig. 17

Example: target sites for knock-outs of human protein-coding genes

1. Extracting coordinates of all human protein-coding genes annotated by GENCODE, version 26 from 2017/03

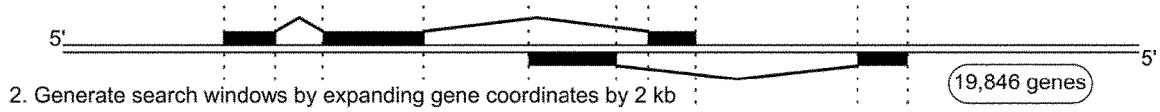

19,846 genes

2. Generate search windows by expanding gene coordinates by 2 kb

3. Remove fragments overlapping with other genes 17,682 fragments covering 17,417 genes

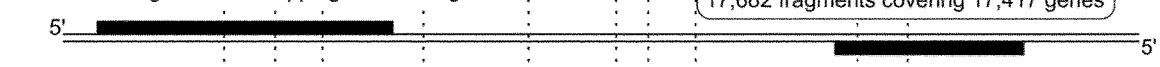

4. In each fragment, identify all spacer sequences that are repeated at least once, and generate all combinations of identical pairs

ATGAGGAC  ATGAGGAC

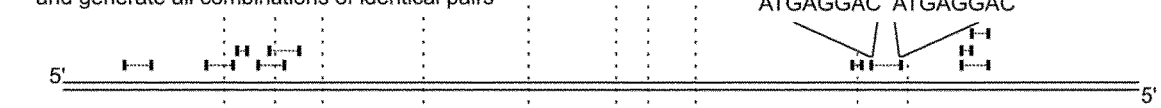

4. Discard pairs of target sites that are not overlaping with gene exons

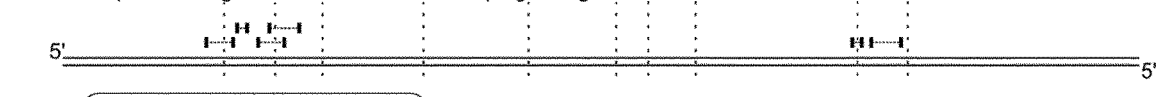

1,703,123,168 pairs of target sites
~97,785 per gene

6. Identifying required number of recombinases by analyzing sequence homology between sets of half-sites

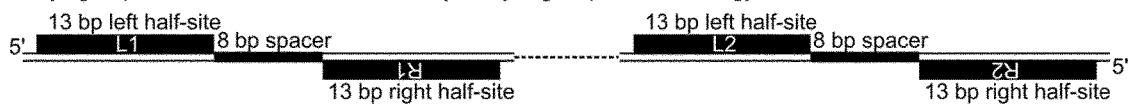

a) 1 recombinase all half-sites dffer at maximum 4 positions:   b) 2 recombinases, pairwise difference of maximum 4 mismatches:

c) 3 recombinases, only one pair of half-sites with max. 4 mismatches:      d) 4 recombinases:

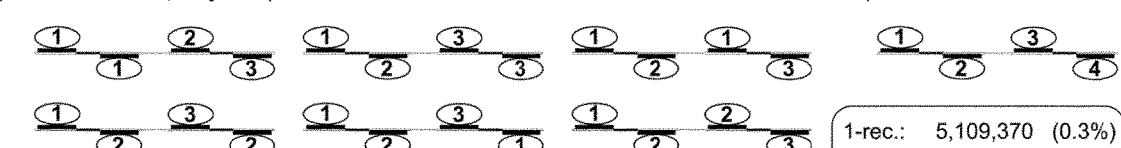

1-rec.:     5,109,370   (0.3%)
2-rec.: 667,624,282 (39.2%)
3-rec.: 141,359,223   (8.3%)
4-rec.: 889,030,294 (52.2%)

7. Genome-wide off-target search by looking for sequences matching the half-sites

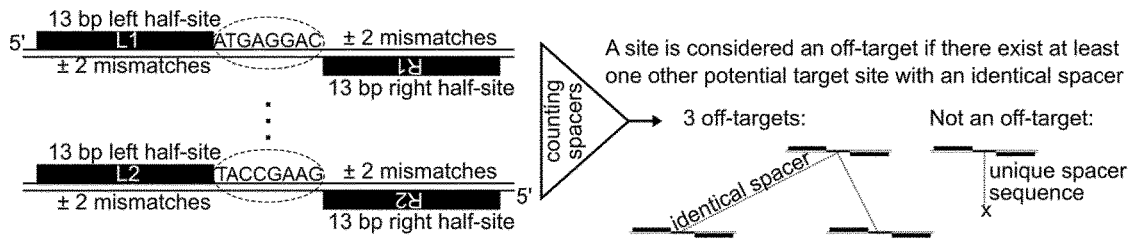

A site is considered an off-target if there exist at least one other potential target site with an identical spacer 3 off-targets:        Not an off-target:

identical spacer      unique spacer sequence
                      x

Estimated counts (based on results of the 2 kb windows) of pairs of target sites
without predicted off-targets, assuming 97,785 pairs per gene:
1-rec.:  0.3% -      293 per gene    3-rec.:  1.8% -     8116 per gene
2-rec.:  0.4% - 38,332 per gene    4-rec.: 24.5% - 51,044 per gene

Fig. 19

Example: 2 kb intervals spanning all human chromosomes

1. Generate search windows by creating consecutive 2 kb intervals over human reference genome, version GRCh38.p10 from 2017/01/06

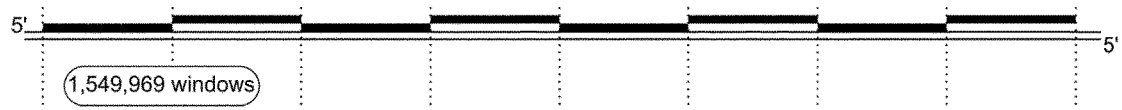

1,549,969 windows

2. In each window, identify all spacer sequences that are repeated at least once, and generate all combinations of identical pairs

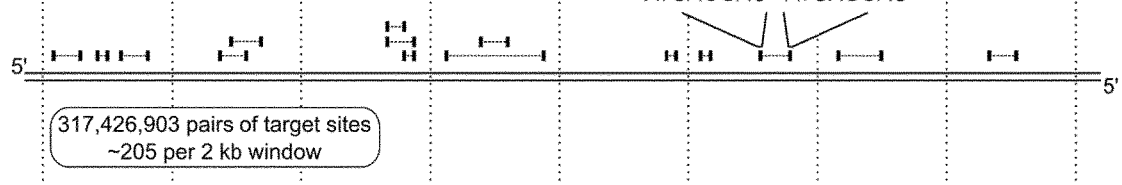

317,426,903 pairs of target sites ~205 per 2 kb window

3. Identifying required number of recombinases by analyzing sequence homology between sets of half-sites

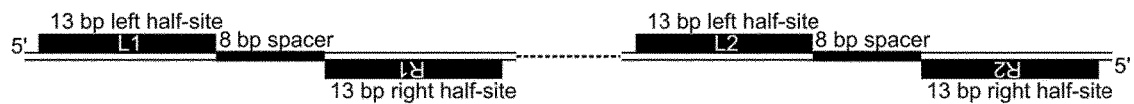

a) 1 recombinase all half-sites differ at maximum 4 positions:
b) 2 recombinases, pairwise difference of maximum 4 mismatches:

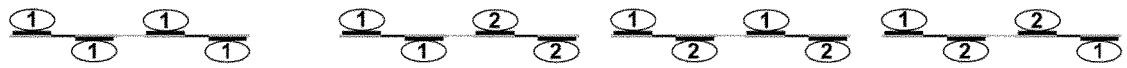

c) 3 recombinases, only one pair of half-sites with max. 4 mismatches:

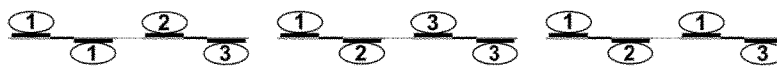

d) 4 recombinases:

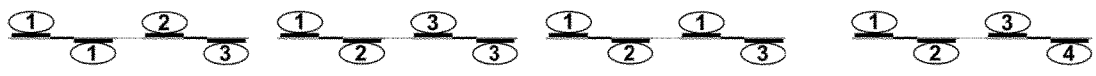

1-rec.: 1,107,787 (0.4%)
2-rec.: 117,923,973 (37.1%)
3-rec.: 34,680,593 (10.9%)
4-rec.: 163,714,550 (51.6%)

4. Genome-wide off-target search by looking for sequences matching the half-sites

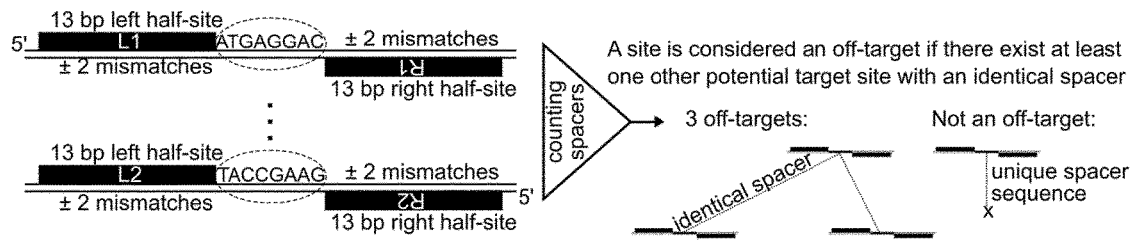

A site is considered an off-target if there exist at least one other potential target site with an identical spacer 3 off-targets:  Not an off-target:
identical spacer  unique spacer sequence Counts of pairs of target sites without predicted off-targets:
1-rec.: 7 out of 2,500 tested (0.3%)   3-rec.: 44 out of 2,500 tested (1.8%)
2-rec.: 9 out of 2,500 tested (0.4%)   4-rec.: 612 out of 2,500 tested (24.5%)

Fig. 20

Schematic figure of the plasmid substrate

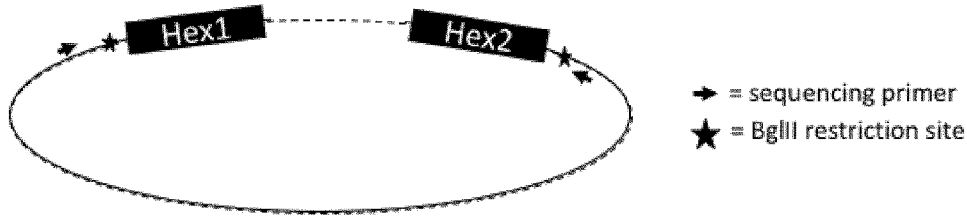

→ = sequencing primer
★ = BglII restriction site

Sequencing of the target sites on the plasmid

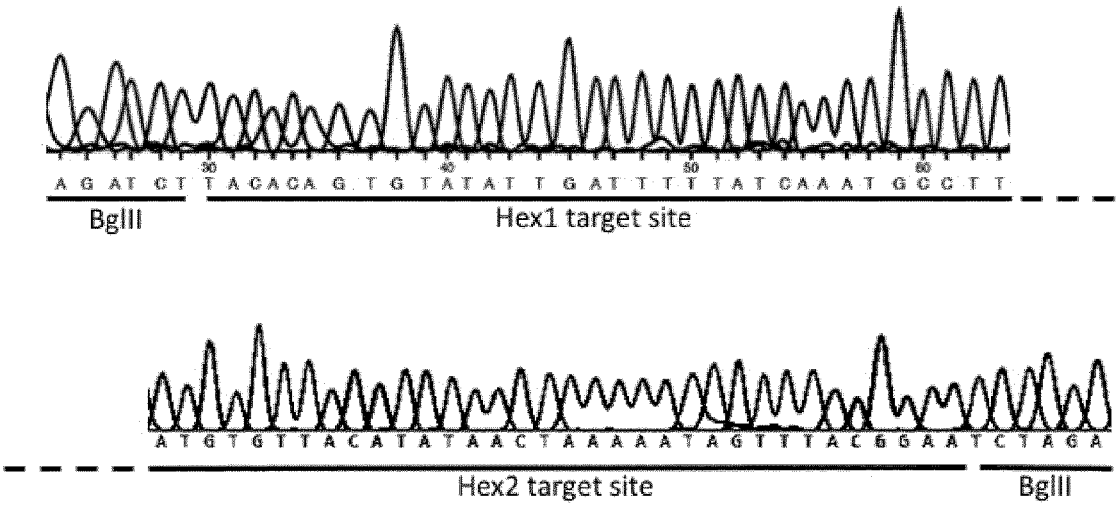

AGATCT TACACA GTG TATAT T GAT TTT TAT CAAAT GCCTT
BglII          Hex1 target site ATGTGTTACATATAACTAAAAATAGTTTACGGAATCTAGA
         Hex2 target site                BglII Schematic figure of the plasmid substrate after recombination

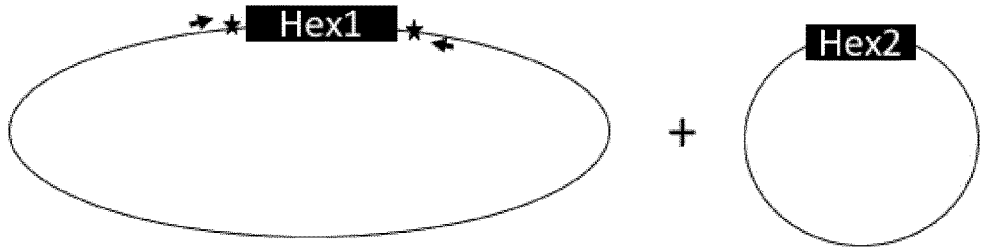

+

Sequencing of the recombined plasmid substrate

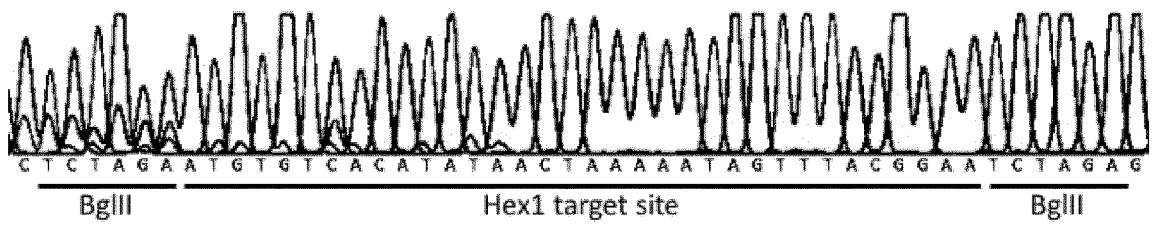

CTCTAGAATGTGTCACATATAACTAAAAATAGTTTACGGAATCTAGAG
BglII              Hex1 target site              BglII

Fig. 22

SEQUENCE LISTING

```
<160> NUMBER OF SEQ ID NOS: 49

<210> SEQ ID NO 1
<211> LENGTH: 343
<212> TYPE: PRT
<213> ORGANISM: Artificial Sequence
<220> FEATURE:
<223> OTHER INFORMATION: Recombinase F9-1
<220> FEATURE:
<221> NAME/KEY: MISC_FEATURE
<222> LOCATION: (17)..(17)
<223> OTHER INFORMATION: Xaa can be any naturally occurring amino acid,
      preferably aspartic acid or glycine
<220> FEATURE:
<221> NAME/KEY: MISC_FEATURE
<222> LOCATION: (19)..(19)
<223> OTHER INFORMATION: Xaa can be any naturally occurring amino acid,
      preferably threonine or alanine
<220> FEATURE:
<221> NAME/KEY: MISC_FEATURE
<222> LOCATION: (22)..(22)
<223> OTHER INFORMATION: Xaa can be any naturally occurring amino acid,
      preferably glycine or glutamic acid
<220> FEATURE:
<221> NAME/KEY: MISC_FEATURE
<222> LOCATION: (30)..(30)
<223> OTHER INFORMATION: Xaa is a small unpolar amino acid, preferably
      selected from valine, leucine, isoleucine, alanine and glycine
<220> FEATURE:
<221> NAME/KEY: MISC_FEATURE
<222> LOCATION: (43)..(43)
<223> OTHER INFORMATION: Xaa is a positively charged amino acid,
```

```
      preferably lysine or arginine
<220> FEATURE:
<221> NAME/KEY: MISC_FEATURE
<222> LOCATION: (60)..(60)
<223> OTHER INFORMATION: Xaa can be any naturally occurring amino acid,
      preferably aspartic acid or asparagine
<220> FEATURE:
<221> NAME/KEY: MISC_FEATURE
<222> LOCATION: (68)..(68)
<223> OTHER INFORMATION: Xaa can be any naturally occurring amino acid,
      preferably proline or serine
<220> FEATURE:
<221> NAME/KEY: MISC_FEATURE
<222> LOCATION: (69)..(69)
<223> OTHER INFORMATION: Xaa is a charged  amino acid, preferably
      selected form aspartic acid, glutamic acid, lysine or arginine
<220> FEATURE:
<221> NAME/KEY: MISC_FEATURE
<222> LOCATION: (81)..(81)
<223> OTHER INFORMATION: Xaa is a polar amino acid, preferably selected
      from serine, threonine, cysteine, lysine or arginine
<220> FEATURE:
<221> NAME/KEY: MISC_FEATURE
<222> LOCATION: (84)..(84)
<223> OTHER INFORMATION: Xaa can be any naturally occurring amino acid,
      preferably alanine or threonine
<220> FEATURE:
<221> NAME/KEY: MISC_FEATURE
<222> LOCATION: (89)..(89)
<223> OTHER INFORMATION: Xaa can be any naturally occurring amino acid,
      preferably leucine or glutamine
<220> FEATURE:
<221> NAME/KEY: MISC_FEATURE
<222> LOCATION: (93)..(93)
<223> OTHER INFORMATION: Xaa is a small amino acid, preferably selected
      from cysteine, serine and alanine
<220> FEATURE:
<221> NAME/KEY: MISC_FEATURE
<222> LOCATION: (140)..(140)
<223> OTHER INFORMATION: Xaa can be any naturally occurring amino acid,
      preferably isoleucine or threonine
<220> FEATURE:
<221> NAME/KEY: MISC_FEATURE
<222> LOCATION: (166)..(166)
<223> OTHER INFORMATION: Xaa is an unpolar amino acid, preferably
      selected from isoleucine, leucine and valine
<220> FEATURE:
<221> NAME/KEY: MISC_FEATURE
<222> LOCATION: (177)..(177)
<223> OTHER INFORMATION: Xaa is an unpolar amino acid, preferably
      selected from isoleucine, leucine and valine
<220> FEATURE:
<221> NAME/KEY: MISC_FEATURE
<222> LOCATION: (182)..(182)
<223> OTHER INFORMATION: Xaa is an unpolar amino acid, preferably
      selected from isoleucine, leucine and valine
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: MISC_FEATURE
<222> LOCATION: (184)..(184)
<223> OTHER INFORMATION: Xaa is a postively cahrged amino acid,
      preferably selected from lysine and arginine
<220> FEATURE:
<221> NAME/KEY: MISC_FEATURE
<222> LOCATION: (186)..(186)
<223> OTHER INFORMATION: Xaa is a polar amino acid, preferably selected
      from serine or threonine
<220> FEATURE:
<221> NAME/KEY: MISC_FEATURE
<222> LOCATION: (206)..(206)
<223> OTHER INFORMATION: Xaa can be any naturally occurring amino acid,
      preferably alanine or threonine
<220> FEATURE:
<221> NAME/KEY: MISC_FEATURE
<222> LOCATION: (222)..(222)
<223> OTHER INFORMATION: Xaa can be any naturally occurring amino acid,
```

```
      preferably valine or glutamic acid
<220> FEATURE:
<221> NAME/KEY: MISC_FEATURE
<222> LOCATION: (225)..(225)
<223> OTHER INFORMATION: Xaa is an unpolar amino acid, preferably
      selected from isoleucine, leucine and valine
<220> FEATURE:
<221> NAME/KEY: MISC_FEATURE
<222> LOCATION: (237)..(237)
<223> OTHER INFORMATION: Xaa is a polar amino acid, preferably selected
      from serine, threonine, cysteine or tyrosine
<220> FEATURE:
<221> NAME/KEY: MISC_FEATURE
<222> LOCATION: (239)..(239)
<223> OTHER INFORMATION: Xaa is an unpolar amino acid, preferably
      selected from isoleucine, leucine, valine or phenylalanine
<220> FEATURE:
<221> NAME/KEY: MISC_FEATURE
<222> LOCATION: (249)..(249)
<223> OTHER INFORMATION: Xaa is a small unpolar amino acid, preferably
      selected from alanine, glycine, isoleucine, leucine and valine
<220> FEATURE:
<221> NAME/KEY: MISC_FEATURE
<222> LOCATION: (259)..(259)
<223> OTHER INFORMATION: Xaa can be any naturally occurring amino acid,
      preferably phenylalanine or proline
<220> FEATURE:
<221> NAME/KEY: MISC_FEATURE
<222> LOCATION: (260)..(260)
<223> OTHER INFORMATION: Xaa can be any naturally occurring amino acid,
      preferably threonine or alanine
<220> FEATURE:
<221> NAME/KEY: MISC_FEATURE
<222> LOCATION: (264)..(264)
<223> OTHER INFORMATION: Xaa can be any naturally occurring amino acid,
      preferably alanine or aspartic acid
<220> FEATURE:
<221> NAME/KEY: MISC_FEATURE
<222> LOCATION: (278)..(278)
<223> OTHER INFORMATION: Xaa can be any naturally occurring amino acid,
      preferably leucine or glutamine
<220> FEATURE:
<221> NAME/KEY: MISC_FEATURE
<222> LOCATION: (284)..(284)
<223> OTHER INFORMATION: Xaa is an unpolar amino acid, preferably
      selected from isoleucine, leucine or valine
<220> FEATURE:
<221> NAME/KEY: MISC_FEATURE
<222> LOCATION: (318)..(318)
<223> OTHER INFORMATION: Xaa is an unpolar amino acid, preferably
      selected from isoleucine, leucine or valine
<220> FEATURE:
<221> NAME/KEY: MISC_FEATURE
<222> LOCATION: (342)..(342)
<223> OTHER INFORMATION: Xaa can be any naturally occurring amino acid,
      preferably glycine or aspartic acid

<400> SEQUENCE: 1

Met Ser Asn Leu Gln Thr Leu His Gln Asn Leu Ser Ala Leu Leu Val
1               5                   10                  15

Xaa Ala Xaa Ser Asp Xaa Ala Arg Lys Asn Leu Met Asp Xaa Phe Arg
            20                  25                  30

Asp Arg Gln Ala Phe Ser Glu His Thr Trp Xaa Val Leu Leu Ser Val
        35                  40                  45

Cys Arg Ser Trp Ala Ala Trp Cys Lys Leu Asn Xaa Arg Lys Trp Phe
    50                  55                  60

Pro Ala Glu Xaa Xaa Asp Val Arg Asp Tyr Leu Leu His Leu Gln Ala
65                  70                  75                  80

Xaa Gly Leu Xaa Val Asn Thr Ile Xaa Gln His Leu Xaa Gln Leu Asn
                85                  90                  95

Met Leu His Arg Arg Ser Gly Leu Pro Arg Pro Gly Asp Ser Asn Ala
            100                 105                 110
```

```
Val Ser Leu Val Met Arg Arg Ile Arg Lys Glu Asn Val Asp Ala Gly
        115                 120                 125

Glu Arg Val Lys Gln Ala Leu Ala Phe Glu Arg Xaa Asp Phe Asp Gln
130                 135                 140

Val Arg Ser Leu Met Glu Asn Ser Asp Arg Cys Gln Asp Ile Arg Asn
145                 150                 155                 160

Leu Ala Phe Leu Gly Xaa Ala Tyr Asn Thr Leu Leu Arg Ile Ser Glu
                165                 170                 175

Xaa Ala Arg Ile Arg Xaa Xaa Asp Ile Xaa Arg Thr Asp Gly Gly Arg
            180                 185                 190

Met Leu Ile His Ile Gly Arg Thr Lys Thr Leu Val Ser Xaa Ala Gly
        195                 200                 205

Val Glu Lys Ala Leu Ser Leu Arg Val Thr Arg Leu Val Xaa Arg Trp
    210                 215                 220

Xaa Ser Val Ser Gly Val Ala Asp Asp Pro Asn Asn Xaa Leu Xaa Cys
225                 230                 235                 240

Arg Val Arg Arg Asn Gly Val Ala Xaa Pro Ser Ala Thr Ser Gln Leu
                245                 250                 255

Ser Thr Xaa Xaa Leu Gln Gly Xaa Phe Ala Ala His Arg Leu Ile
            260                 265                 270

Tyr Gly Ala Arg Asp Xaa Ser Gly Gln Arg Tyr Xaa Thr Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Xaa Glu Ser
305                 310                 315                 320

Val Met Asn Tyr Ile Arg Asn Leu Asp Ser Glu Thr Gly Ala Met Val
                325                 330                 335

Arg Leu Leu Glu Asp Xaa Asp
            340

<210> SEQ ID NO 2
<211> LENGTH: 343
<212> TYPE: PRT
<213> ORGANISM: Artificial Sequence
<220> FEATURE:
<223> OTHER INFORMATION: Recombinase F9-2
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
```

```
<222> LOCATION: (31)..(31)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (182)..(183)
<223> OTHER INFORMATION: Xaa can be any naturally occurring amino acid
<220> FEATURE:
<221> NAME/KEY: misc_feature
<222> LOCATION: (186)..(186)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (259)..(260)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (276)..(276)
<223> OTHER INFORMATION: Xaa can be any naturally occurring amino acid
<220> FEATURE:
```

```
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (306)..(306)
<223> OTHER INFORMATION: Xaa can be any naturally occurring amino acid
<220> FEATURE:
<221> NAME/KEY: misc_feature
<222> LOCATION: (325)..(325)
<223> OTHER INFORMATION: Xaa can be any naturally occurring amino acid

<400> SEQUENCE: 2

Met Ser Xaa Leu Xaa Thr Leu Xaa Gln Asn Leu Ser Ala Xaa Leu Xaa
1               5                   10                  15

Asp Xaa Xaa Xaa Xaa Glu Ala Arg Lys Asn Leu Met Asp Val Xaa Arg
            20                  25                  30

Asp Arg Gln Ala Phe Ser Xaa His Thr Trp Arg Val Leu Leu Ser Val
        35                  40                  45

Cys Arg Ser Trp Ala Ala Trp Cys Glu Leu Asn Asn Arg Lys Trp Phe
50                  55                  60

Pro Ala Glu Pro Glu Asp Val Arg Asp Tyr Leu Leu His Leu Gln Xaa
65                  70                  75                  80

Arg Gly Leu Xaa Val Asn Thr Ile Gln Gln His Leu Xaa Gln Leu Asn
                85                  90                  95

Xaa Leu His Arg Arg Ser Gly Leu Pro Arg Pro Gly Asp Ser Asn Ala
            100                 105                 110

Val Ser Leu Val Met Arg Arg Ile Arg Lys Glu Asn Xaa Asp Ala Gly
        115                 120                 125

Glu Arg Val Xaa Gln Ala Leu Ala Phe Glu Arg Thr Asp Phe Asp Gln
130                 135                 140

Val Arg Ser Leu Met Glu Asn Ser Asp Arg Cys Gln Asp Ile Arg Asn
145                 150                 155                 160

Leu Ala Phe Leu Gly Val Ala Tyr Asn Thr Leu Leu Arg Ile Ser Glu
                165                 170                 175

Ile Ala Arg Ile Arg Xaa Xaa Asp Ile Xaa Arg Thr Asp Gly Gly Arg
            180                 185                 190

Met Leu Xaa His Ile Gly Arg Thr Lys Thr Leu Val Ser Xaa Ala Gly
        195                 200                 205

Val Glu Lys Ala Leu Ser Leu Xaa Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Arg Val Arg Arg Asn Gly Val Ala Xaa Pro Ser Ala Xaa Ser Gln Leu
                245                 250                 255

Ser Thr Xaa Xaa Leu Gln Gly Xaa Phe Xaa Ala Ala His Arg Leu Ile
            260                 265                 270

Xaa Gly Ala Xaa Asp Xaa Ser Gly Gln Arg Tyr Leu Thr Trp Ser Gly
        275                 280                 285

His Ser Ala Arg Val Gly Ala Ala Arg Asp Met Ala Arg Ala Gly Val
290                 295                 300

Ser Xaa Ala Glu Ile Met Gln Ala Gly Gly Trp Thr Thr Val Glu Ser
305                 310                 315                 320

Val Met Asn Tyr Xaa Arg Asn Leu Asp Ser Glu Thr Gly Ala Met Val
                325                 330                 335

Arg Leu Leu Glu Asp Gly Asp
            340
```

```
<210> SEQ ID NO 3
<211> LENGTH: 343
<212> TYPE: PRT
<213> ORGANISM: Artificial Sequence
<220> FEATURE:
<223> OTHER INFORMATION: Recombinase F9-1a

<400> SEQUENCE: 3

Met Ser Asn Leu Gln Thr Leu His Gln Asn Leu Ser Ala Leu Leu Val
 1               5                  10                  15

Asp Ala Thr Ser Asp Gly Ala Arg Lys Asn Leu Met Asp Val Phe Arg
            20                  25                  30

Asp Arg Gln Ala Phe Ser Glu His Thr Trp Lys Val Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu His Leu Gln Ala
65                  70                  75                  80

Cys Gly Leu Ala Val Asn Thr Ile Leu Gln His Leu Ala Gln Leu Asn
                85                  90                  95

Met Leu His Arg Arg Ser Gly Leu Pro Arg Pro Gly Asp Ser Asn Ala
            100                 105                 110

Val Ser Leu Val Met Arg Arg Ile Arg Lys Glu Asn Val Asp Ala Gly
        115                 120                 125

Glu Arg Val Lys Gln Ala Leu Ala Phe Glu Arg Ile Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ser Glu
                165                 170                 175

Val Ala Arg Ile Arg Ile Lys Asp Ile Ser Arg Thr Asp Gly Gly Arg
            180                 185                 190

Met Leu Ile His Ile Gly Arg Thr Lys Thr Leu Val Ser Ala Ala Gly
        195                 200                 205

Val Glu Lys Ala Leu Ser Leu Arg Val Thr Arg Leu Val Val Arg Trp
    210                 215                 220

Val Ser Val Ser Gly Val Ala Asp Asp Pro Asn Asn Tyr Leu Phe Cys
225                 230                 235                 240

Arg Val Arg Arg Asn Gly Val Ala Val Pro Ser Ala Thr Ser Gln Leu
                245                 250                 255

Ser Thr Phe Thr Leu Gln Gly Val Phe Ala Ala Ala His Arg Leu Ile
            260                 265                 270

Tyr Gly Ala Arg Asp Ala Ser Gly Gln Arg Tyr Leu Thr Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Glu Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 4
```

<211> LENGTH: 343
<212> TYPE: PRT
<213> ORGANISM: Artificial Sequence
<220> FEATURE:
<223> OTHER INFORMATION: Recombinase F9-2a

<400> SEQUENCE: 4

Met Ser Lys Leu Pro Thr Leu His Gln Asn Leu Ser Ala Leu Leu Ala
1               5                   10                  15

Asp Ala Thr Ser Asp Glu Ala Arg Lys Asn Leu Met Asp Val Leu Arg
            20                  25                  30

Asp Arg Gln Ala Phe Ser Lys His Thr Trp Arg Val Leu Leu Ser Val
        35                  40                  45

Cys Arg Ser Trp Ala Ala Trp Cys Glu Leu Asn Asn Arg Lys Trp Phe
    50                  55                  60

Pro Ala Glu Pro Glu Asp Val Arg Asp Tyr Leu Leu His Leu Gln Thr
65                  70                  75                  80

Arg Gly Leu Thr Val Asn Thr Ile Gln Gln His Leu Cys Gln Leu Asn
                85                  90                  95

Leu Leu His Arg Arg Ser Gly Leu Pro Arg Pro Gly Asp Ser Asn Ala
            100                 105                 110

Val Ser Leu Val Met Arg Arg Ile Arg Lys Glu Asn Ile Asp Ala Gly
        115                 120                 125

Glu Arg Val Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Thr Arg Thr Asp Gly Gly Arg
            180                 185                 190

Met Leu Ile His Ile Gly Arg Thr Lys Thr Leu Val Ser Ala Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Arg Asn Gly Val Ala Ala Pro Ser Ala Ile Ser Gln Leu
                245                 250                 255

Ser Thr Pro Ala Leu Gln Gly Val Phe Ala Ala His Arg Leu Ile
            260                 265                 270

His Gly Ala Lys Asp Ala Ser Gly Gln Arg Tyr Leu Thr Trp Ser Gly
        275                 280                 285

His Ser Ala Arg Val Gly Ala Ala Arg Asp Met Ala Arg Ala Gly Val
    290                 295                 300

Ser Val Ala Glu Ile Met Gln Ala Gly Gly Trp Thr Thr Val Glu Ser
305                 310                 315                 320

Val Met Asn Tyr Leu Arg Asn Leu Asp Ser Glu Thr Gly Ala Met Val
                325                 330                 335

Arg Leu Leu Glu Asp Gly Asp
            340

<210> SEQ ID NO 5
<211> LENGTH: 343
<212> TYPE: PRT
<213> ORGANISM: Artificial Sequence
<220> FEATURE:
<223> OTHER INFORMATION: Recombinase F9-1b

<400> SEQUENCE: 5

```
Met Ser Asn Leu Gln Thr Leu His Gln Asn Leu Ser Ala Leu Leu Val
1               5                   10                  15

Gly Ala Ala Ser Asp Glu Ala Arg Lys Asn Leu Met Asp Ala Phe Arg
                20                  25                  30

Asp Arg Gln Ala Phe Ser Glu His Thr Trp Arg Val Leu Leu Ser Val
            35                  40                  45

Cys Arg Ser Trp Ala Ala Trp Cys Lys Leu Asn Asp Arg Lys Trp Phe
        50                  55                  60

Pro Ala Glu Ser Lys Asp Val Arg Asp Tyr Leu Leu His Leu Gln Ala
65                  70                  75                  80

Arg Gly Leu Thr Val Asn Thr Ile Gln Gln His Leu Cys Gln Leu Asn
                85                  90                  95

Met Leu His Arg Arg Ser Gly Leu Pro Arg Pro Gly Asp Ser Asn Ala
                100                 105                 110

Val Ser Leu Val Met Arg Arg Ile Arg Lys Glu Asn Val Asp Ala Gly
            115                 120                 125

Glu Arg Val Lys Gln Ala Leu Ala Phe Glu Arg Thr Asp Phe Asp Gln
        130                 135                 140

Val Arg Ser Leu Met Glu Asn Ser Asp Arg Cys Gln Asp Ile Arg Asn
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Thr Arg Thr Asp Gly Gly Arg
                180                 185                 190

Met Leu Ile His Ile Gly Arg Thr Lys Thr Leu Val Ser Thr Ala Gly
            195                 200                 205

Val Glu Lys Ala Leu Ser Leu Arg Val Thr Arg Leu Val Glu Arg Trp
        210                 215                 220

Ile Ser Val Ser Gly Val Ala Asp Pro Asn Asn Cys Leu Ile Cys
225                 230                 235                 240

Arg Val Arg Arg Asn Gly Val Ala Ala Pro Ser Ala Thr Ser Gln Leu
                245                 250                 255

Ser Thr Pro Ala Leu Gln Gly Ile Phe Ala Ala His Arg Leu Ile
                260                 265                 270

Tyr Gly Ala Arg Asp Asp Ser Gly Gln Arg Tyr Gln Thr Trp Ser Gly
            275                 280                 285

His Ser Ala Arg Val Gly Ala Ala Arg Asp Met Ala Arg Ala Gly Val
        290                 295                 300

Ser Ile Ala Glu Ile Met Gln Ala Gly Gly Trp Thr Thr Ile Glu Ser
305                 310                 315                 320

Val Met Asn Tyr Leu Arg Asn Leu Asp Ser Glu Thr Gly Ala Met Val
                325                 330                 335

Arg Leu Leu Glu Asp Asp Asp
            340
```

<210> SEQ ID NO 6
<211> LENGTH: 343
<212> TYPE: PRT
<213> ORGANISM: Artificial Sequence
<220> FEATURE:
<223> OTHER INFORMATION: F9-2b

<400> SEQUENCE: 6

```
Met Ser Asn Leu Gln Thr Leu Thr Gln Asn Leu Ser Ala Ile Leu Val
1               5                   10                  15

Asp Gly Ala Asn Gly Glu Ala Arg Lys Asn Leu Met Asp Val Phe Arg
            20                  25                  30

Asp Arg Gln Ala Phe Ser Glu His Thr Trp Arg Val Leu Leu Ser Val
        35                  40                  45

Cys Arg Ser Trp Ala Ala Trp Cys Glu Leu Asn Asn Arg Lys Trp Phe
50                  55                  60

Pro Ala Glu Pro Glu Asp Val Arg Asp Tyr Leu Leu His Leu Gln Ala
65                  70                  75                  80

Arg Gly Leu Ala Val Asn Thr Ile Gln Gln His Leu Ala Gln Leu Asn
                85                  90                  95

Met Leu His Arg Arg Ser Gly Leu Pro Arg Pro Gly Asp Ser Asn Ala
            100                 105                 110

Val Ser Leu Val Met Arg Arg Ile Arg Lys Glu Asn Val Asp Ala Gly
        115                 120                 125

Glu Arg Val Arg Gln Ala Leu Ala Phe Glu Arg Thr Asp Phe Asp Gln
130                 135                 140

Val Arg Ser Leu Met Glu Asn Ser Asp Arg Cys Gln Asp Ile Arg Asn
145                 150                 155                 160

Leu Ala Phe Leu Gly Val Ala Tyr Asn Thr Leu Leu Arg Ile Ser Glu
                165                 170                 175

Ile Ala Arg Ile Arg Ile Lys Asp Ile Ser Arg Thr Asp Gly Gly Arg
            180                 185                 190

Met Leu Val His Ile Gly Arg Thr Lys Thr Leu Val Ser Thr Ala Gly
        195                 200                 205

Val Glu Lys Ala Leu Ser Leu Arg Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Arg Val Arg Arg Asn Gly Val Ala Val Pro Ser Ala Thr Ser Gln Leu
                245                 250                 255

Ser Thr Ser Thr Leu Gln Gly Ile Phe Gly Ala Ala His Arg Leu Ile
            260                 265                 270

Tyr Gly Ala Gln Asp Asp Ser Gly Gln Arg Tyr Leu Thr Trp Ser Gly
        275                 280                 285

His Ser Ala Arg Val Gly Ala Ala Arg Asp Met Ala Arg Ala Gly Val
290                 295                 300

Ser Ile Ala Glu Ile Met Gln Ala Gly Gly Trp Thr Thr Val Glu Ser
305                 310                 315                 320

Val Met Asn Tyr Ile Arg Asn Leu Asp Ser Glu Thr Gly Ala Met Val
                325                 330                 335

Arg Leu Leu Glu Asp Gly Gly
            340
```

<210> SEQ ID NO 7
<211> LENGTH: 34
<212> TYPE: DNA
<213> ORGANISM: Homo sapiens

<400> SEQUENCE: 7
ctcattacat ttaaccaaaa ttatcacaat ataa                        34

-continued

```
<210> SEQ ID NO 8
<211> LENGTH: 34
<212> TYPE: DNA
<213> ORGANISM: Homo sapiens

<400> SEQUENCE: 8
ccatcttttg ttagatttga atatatacat tcta                                    34

<210> SEQ ID NO 9
<211> LENGTH: 34
<212> TYPE: DNA
<213> ORGANISM: Bacteriophage P1

<400> SEQUENCE: 9
ataacttcgt ataatgtatg ctatacgaag ttat                                    34

<210> SEQ ID NO 10
<211> LENGTH: 34
<212> TYPE: DNA
<213> ORGANISM: Homo sapiens

<400> SEQUENCE: 10
atatatacgt atatagacat atatacgtat atat                                    34

<210> SEQ ID NO 11
<211> LENGTH: 34
<212> TYPE: DNA
<213> ORGANISM: Artificial Sequence
<220> FEATURE:
<223> OTHER INFORMATION: LoxM7 target site - artificial variant of LoxP

<400> SEQUENCE: 11
ataactctat ataatgtatg ctatatagag ttat                                    34

<210> SEQ ID NO 12
<211> LENGTH: 34
<212> TYPE: DNA
<213> ORGANISM: Artificial Sequence
<220> FEATURE:
<223> OTHER INFORMATION: LoxM5 target site - artificial variant of LoxP

<400> SEQUENCE: 12
ataacttcgt gcaatgtatg ctgcacgaag ttat                                    34

<210> SEQ ID NO 13
<211> LENGTH: 34
<212> TYPE: DNA
<213> ORGANISM: Human immunodeficiency virus

<400> SEQUENCE: 13
acaacatcct attacaccct atatgccaac atgg                                    34

<210> SEQ ID NO 14
<211> LENGTH: 34
<212> TYPE: DNA
<213> ORGANISM: Human immunodeficiency virus

<400> SEQUENCE: 14
aacccactgc ttaagcctca ataaagcttg cctt                                    34

<210> SEQ ID NO 15
<211> LENGTH: 34
<212> TYPE: DNA
<213> ORGANISM: Artificial Sequence
<220> FEATURE:
```

<223> OTHER INFORMATION: Intermediate target site loxF9-AL

<400> SEQUENCE: 15
ctcattacat ttaaccaaaa ttaaatgtaa tgag                               34

<210> SEQ ID NO 16
<211> LENGTH: 34
<212> TYPE: DNA
<213> ORGANISM: Artificial Sequence
<220> FEATURE:
<223> OTHER INFORMATION: Intermediate target site loxF9-AR

<400> SEQUENCE: 16
ttatattgtg ataaccaaaa ttatcacaat ataa                               34

<210> SEQ ID NO 17
<211> LENGTH: 34
<212> TYPE: DNA
<213> ORGANISM: Artificial Sequence
<220> FEATURE:
<223> OTHER INFORMATION: Intermediate target site loxF9-BLS

<400> SEQUENCE: 17 ccaactttg atagatttga atatcaaaag ttgg                                34

<210> SEQ ID NO 18
<211> LENGTH: 34
<212> TYPE: DNA
<213> ORGANISM: Artificial Sequence
<220> FEATURE:
<223> OTHER INFORMATION: Intermediate target site loxF9-BRS

<400> SEQUENCE: 18
tagactttat atagatttga atatataaag tcta                               34

<210> SEQ ID NO 19
<211> LENGTH: 34
<212> TYPE: DNA
<213> ORGANISM: Artificial Sequence
<220> FEATURE:
<223> OTHER INFORMATION: Intermediate target site loxF9-BL

<400> SEQUENCE: 19
ccatcttttg ttagatttga ataacaaaag atgg                               34

<210> SEQ ID NO 20
<211> LENGTH: 34
<212> TYPE: DNA
<213> ORGANISM: Artificial Sequence
<220> FEATURE:
<223> OTHER INFORMATION: Intermediate target site loxF9-BR

<400> SEQUENCE: 20
ccatcttttg ttagatttga ataacaaaag atgg                               34

<210> SEQ ID NO 21
<211> LENGTH: 7184
<212> TYPE: DNA
<213> ORGANISM: Artificial Sequence
<220> FEATURE:
<223> OTHER INFORMATION: vector pDuoF9 (source)
<220> FEATURE:
<221> NAME/KEY: P1 binding site
<222> LOCATION: (1412)..(1430)
<220> FEATURE:
<221> NAME/KEY: Rec. F9-1 (placeholder)
<222> LOCATION: (1519)..(2550)

```
<220> FEATURE:
<221> NAME/KEY: Ribosome binding site
<222> LOCATION: (2551)..(2633)
<220> FEATURE:
<221> NAME/KEY: Rec. F9-2 (placeholder)
<222> LOCATION: (2634)..(3665)
<220> FEATURE:
<221> NAME/KEY: LoxF9a
<222> LOCATION: (4220)..(4253)
<220> FEATURE:
<221> NAME/KEY: LoxF9b
<222> LOCATION: (4961)..(4994)
<220> FEATURE:
<221> NAME/KEY: P2 binding site
<222> LOCATION: (5012)..(5028)
<220> FEATURE:
<221> NAME/KEY: CmR
<222> LOCATION: (5315)..(5974)
<220> FEATURE:
<221> NAME/KEY: Ori
<222> LOCATION: (6336)..(7184)

<400> SEQUENCE: 21
gctcatgagc cgaagtggc gagcccgatc ttccccatcg gtgatgtcgg cgatataggc      60
gccagcaacc gcacctgtgg cgccggtgat gccggccacg atgcgtccgg cgtagaggat    120
ctgctcatgt ttgacagctt atcatcgatg cataatgtgc ctgtcaaatg gacgaagcag    180
ggattctgca aaccctatgc tactccgtca agccgtcaat tgtctgattc gttaccaatt    240
atgacaactt gacggctaca tcattcactt tttcttcaca accggcacgg aactcgctcg    300
ggctggcccc ggtgcatttt ttaaataccc gcgagaaata gagttgatcg tcaaaaccaa    360
cattgcgacc gacggtggcg ataggcatcc gggtggtgct caaaagcagc ttcgcctggc    420
tgatacgttg gtcctcgcgc cagcttaaga cgctaatccc taactgctgg cggaaaagat    480
gtgacagacg cgacggcgac aagcaaacat gctgtgcgac gctggcgata tcaaaattgc    540
tgtctgccag gtgatcgctg atgtactgac aagcctcgcg tacccgatta tccatcggtg    600
gatggagcga ctcgttaatc gcttccatgc gccgcagtaa caattgctca agcagattta    660
tcgccagcag ctccgaatag cgcccttccc cttgcccggc gttaatgatt tgcccaaaca    720
ggtcgctgaa atgcggctgg tgcgcttcat ccgggcgaaa gaaccccgta ttggcaaata    780
ttgacggcca gttaagccat tcatgccagt aggcgcgcgg acgaaagtaa acccactggt    840
gataccattc gcgagcctcc ggatgacgac cgtagtgatg aatctctcct ggcgggaaca    900
gcaaaatatc acccggtcgg caaacaaatt ctcgtccctg attttcacc accccctgac     960 cgcgaatggt gagattgaga atataacctt tcattcccag cggtcggtcg ataaaaaaat   1020
cgagataacc gttggcctca atcggcgtta aaccgccac cagatgggca ttaaacgagt    1080
atcccggcag caggggatca ttttgcgctt cagccatact tttcatactc ccgccattca   1140
gagaagaaac caattgtcca tattgcatca gacattgccg tcactgcgtc ttttactggc   1200
tcttctcgct aaccaaaccg gtaaccccgc ttattaaaag cattctgtaa caaagcggga   1260
ccaaagccat gacaaaaacg cgtaacaaaa gtgtctataa tcacggcaga aaagtccaca   1320
ttgattattt gcacggcgtc acactttgct atgccatagc attttatcc ataagattag    1380 cggatcctac ctgacgcttt ttatcgcaac tctctactgt ttctccatac ccgtttttt    1440 gggctagcga attcgagctc taaggaggtg ccacaattct cgagccatac ccattctaat   1500
gatcataagg aggtgtacat gtcaatacta ctgaccttgc accaaagttt gtccgcatta   1560
ctggtcgatg caacgagtga tgaggctcgc aagaacctga tggatgtgct cagggatcgc   1620
caggcgttct ccgagcgtac ctggaaagtg ctcctgtccg tttgccggac gtgggcggca   1680
```

```
tggtgcaagt tgaacaaccg gaaatggttt cccgcggaac ctgaagatgt tcgcgattac    1740
cttctacatc ttcaggctcg cggtctggca gtaaacacta tcctgcaaca tttggcccag    1800
ctaaacatgc tccaccgtcg gttcgggctg ccacgaccgg gcgacagcga cgctgtttca    1860
ctggttatgc ggcgaatccg aagggagaac gtcgatgctg tgagcgtac gaagcaggcc     1920 ctagcgttcg agcgcactga cttcgaccag gttcgtgcac tcatggaaaa tagcgaacgg    1980
ggccaggata tacgtactct ggcacttctg ggggttgctt ataacaccct gttacgcgta    2040
tccgaaattg ccaggattcg gattaaagac atctcacgta ctgacggtgg gaggatgcta    2100
atccacatta gcagaacgaa aacgctggtc agcaccgcag gcgtagagaa ggcgcttagc    2160
ctgggggtaa ctaaactggt cgagcgatgg atttccgtct ctggtgtggc tagtgaccca    2220
aacaattacc tgttttgcca ggttagaata aatggtgtgg ccgtgccgtc tgccaccagc    2280
cggctatcaa ccgacgtcct gcgaaagatt tttgaggctg cccaccgcct gatctacggt    2340
gccaaggatg ctctggtca gagatacctg gcctggtctg ggcacagtgc ccgtgtcgga     2400
gccgcgcggg atatggcccg cgctgggggtt tcaatagcgg agattatgca ggctggtggc   2460
tggaccaccg tagagagtgt catgaactat atccgtaacc tggacagtga gacaggggca    2520
atggtgcgtc tgctggaaga tggcgactag tctagaggta ccattccgat cgcggatcgg    2580
ccggaatggg atagacgtcc tatcatccac acctactagt taaggaggtg tacatgtcaa    2640
tactactgac cttgcaccaa agtttgtccg cattactggt cgatgcaacg agtgatgagg    2700
ctcgcaagaa cctgatggat gtgctcaggg atcgccaggc gttctccgag cgtacctgga    2760
aagtgctcct gtccgtttgc cggacgtggg cggcatggtg caagttgaac aaccggaaat    2820
ggtttcccgc ggaacctgaa gatgttcgcg attaccttct acatcttcag gctcgcggtc    2880
tggcagtaaa cactatcctg caacatttgg cccagctaaa catgctccac cgtcggttcg    2940
ggctgccacg accgggcgac agcgacgctg tttcactggt tatgcggcga atccgaaggg    3000
agaacgtcga tgctggtgag cgtacgaagc aggccctagc gttcgagcgc actgacttcg    3060
accaggttcg tgcactcatg gaaaatagc aacggggcca ggatatacgt actctggcac    3120 ttctggggt tgcttataac accctgttac gcgtatccga aattgccagg attcggatta    3180
aagacatctc acgtactgac ggtgggagga tgctaatcca cattagcaga acgaaaacgc    3240
tggtcagcac cgcaggcgta gagaaggcgc ttagcctggg ggtaactaaa ctggtcgagc    3300
gatggatttc cgtctctggt gtggctagtg acccaaacaa ttacctgttt tgccaggtta    3360
gaataaatgg tgtggccgtg ccgtctgcca ccagccggct atcaaccgac gtcctgcgaa    3420
agatttttga ggctgcccac cgcctgatct acggtgccaa ggatggctct ggtcagagat    3480
acctggcctg gtctgggcac agtgcccgtg tcggagccgc gcgggatatg gcccgcgctg    3540 ggtttcaat agcggagatt atgcaggctg gtggctggac caccgtagag agtgtcatga    3600
actatatccg taacctggac agtgagacag ggcaatggt gcgtctgctg aagatggcg     3660 actagtctag acgtacgcct gcaggcaagc ttggctgttt tggcggatga gagaagattt    3720
tcagcctgat acagattaaa tcagaacgca gaagcggtct gataaaacag aatttgcctg    3780
gcggcagtag cgcggtggtc ccacctgacc ccatgccgaa ctcagaagtg aaacgccgta    3840
gcgccgatgg tagtgtgggg tctccccatg cgagagtagg gaactgccag gcatcaaata    3900
aaacgaaagg ctcagtcgaa agactgggcc tttcgtttta tctgttgttt gtcggtgaac    3960
gctctcctga gtaggacaaa tccgccggga gcggatttga acgttgcgaa gcaacggccc    4020
```

```
ggagggtggc gggcaggacg cccgccataa actgccaggc atcaaattaa gcagaaggcc    4080
atcctgacgg atggccttt  tgcgtttcta caaactcttt tgtttatttt tctaaataca    4140
ttcaaatatg tatccgctca tgagacaata accctgataa atgcttcaat aatattgaaa    4200
aaggaagagt atgagatctc tcattacatt taaccaaaat tatcacaata taaaagcttg    4260
catgcctgca gatcgaggct ggcctgtatc ggacgggtca tctcgtttcc ttagctgtgt    4320
gcgccatgta aatggcccgg acgtgatggc gtaaatccac ggctgtagcg cgctacgctt    4380
agatcctcat atggtgcact ctcagtacaa tctgctctga tgccgcatag ttaagccagt    4440
atacactccg ctatcgctac gtgactgggt catggctgcg ccccgacacc cgccaacacc    4500
cgctgacgcg ccctgacggg cttgtctgct cccggcatcc gcttacagac aagctgtgac    4560
cgtctccggg agctgcatgt gtcagaggtt ttcaccgtca tcaccgaaac gcgcgaggca    4620
gctgtggaat gtgtgtcagt tagggtgtgg aaagtcccca ggctccccag caggcagaag    4680
tatgcaaagc atgcatctca attagtcagc aaccaggtgt ggaaagtccc caggctcccc    4740
agcaggcaga agtatgcaaa gcatgcatct caattagtca gcaaccatag tcccgccccc    4800
aactccgccc atcccgcccc taactccgcc cagttccgcc cattctccgc cccatggctg    4860 actaatttt  tttatttatg cagaggccga ggccgcctcg gcctaggaac agtcgacgac    4920
actgcagaga cctacttcac taacaaccgg tacagttcga ccatcttttg ttagatttga    4980
atatatacat tctaagatct caacatttcc gtgtcgccct tattccctt  tttgcggcat    5040 tttgccttcc tgttttgct  cacccagaaa cgctggtgaa agtaaaagat gctgaagatc    5100
agttgggtgc agcaaactat taactggcga actacttact ctagcttccc ggcaacaatt    5160
aatagactgg atggaggcgg ataaagttgc aggaccactt ctgcgctcgg cccggtcgaa    5220
tttgctttcg aatttctgcc attcatccgc ttattatcac ttattcaggc gtagcaccag    5280
gcgtttaagg gcaccaataa ctgccttaaa aaattacgc  cccgccctgc cactcatcgc    5340
agtactgttg taattcatta agcattctgc cgacatggaa gccatcacag acggcatgat    5400
gaacctgaat cgccagcggc atcagcacct tgtcgccttg cgtataatat ttgcccatgg    5460
tgaaaacggg ggcgaagaag ttgtccatat tggccacgtt taaatcaaaa ctggtgaaac    5520
tcacccaggg attggctgag acgaaaaaca tattctcaat aaacccttta gggaaatagg    5580
ccaggttttc accgtaacac gccacatctt gcgaatatat gtgtagaaac tgccggaaat    5640
cgtcgtggta ttcactccag agcgatgaaa acgtttcagt ttgctcatgg aaaacggtgt    5700
aacaagggtg aacactatcc catatcacca gctcaccgtc tttcattgcc atacggaatt    5760
ccggatgagc attcatcagg cgggcaagaa tgtgaataaa ggccggataa aacttgtgct    5820
tatttttctt tacggtcttt aaaaaggccg taatatccag ctgaacgtc  tggttatagg    5880 tacattgagc aactgactga atgcctcaa  atgttctttt acgatgccat gggatatat     5940 caacggtggt atatccagtg atttttttct ccatttttagc ttccttagct cctgaaaatc    6000
tcgataactc aaaaaatacg cccggtagtg atcttatttc attatggtga agttggaac     6060 ctcttacgtg ccgatcaacg tctcatttc  gccaaaagtt ggcccagggc ttcccggtat    6120
caacagggac accaggattt atttattctg cgaagtgatc ttccgtcaca ggtatttatt    6180
cggcgcaaag tgcgtcgggt gatgctgcca acttactgat ttagtgtatg atggtgtttt    6240
tgaggtgctc cagtggcttc tgtttctatc agctgtccct cctgttcagc tactgacggg    6300
gtggtgcgta acggcaaaag caccgccgga catcagcgct agcggagtgt atactggctt    6360
actatgttgg cactgatgag ggtgtcagtg aagtgcttca tgtggcagga gaaaaaaggc    6420
```

-continued

```
tgcaccggtg cgtcagcaga atatgtgata caggatatat tccgcttcct cgctcactga   6480
ctcgctacgc tcggtcgttc gactgcggcg agcggaaatg gcttacgaac ggggcggaga   6540
tttcctggaa gatgccagga agatacttaa cagggaagtg agagggccgc ggcaaagccg   6600
tttttccata ggctccgccc ccctgacaag catcacgaaa tctgacgctc aaatcagtgg   6660
tggcgaaacc cgacaggact ataaagatac caggcgtttc cccctggcgg ctccctcgtg   6720
cgctctcctg ttcctgcctt tcggtttacc ggtgtcattc cgctgttatg gccgcgtttg   6780
tctcattcca cgcctgacac tcagttccgg gtaggcagtt cgctccaagc tggactgtat   6840
gcacgaaccc cccgttcagt ccgaccgctg cgccttatcc ggtaactatc gtcttgagtc   6900
caacccggaa agacatgcaa aagcaccact ggcagcagcc actggtaatt gatttagagg   6960
agttagtctt gaagtcatgc gccggttaag gctaaactga aggacaagt tttggtgact    7020 gcgctcctcc aagccagtta cctcggttca aagagttggt agctcagaga accttcgaaa   7080
aaccgccctg caaggcggtt ttttcgtttt cagagcaaga gattacgcgc agaccaaaac   7140
gatctcaaga agatcatctt attaatcaga taaaatattt ctag                    7184
```

<210> SEQ ID NO 22
<211> LENGTH: 2795
<212> TYPE: DNA
<213> ORGANISM: Artificial Sequence
<220> FEATURE:
<223> OTHER INFORMATION: pDonor vector
<220> FEATURE:
<221> NAME/KEY: AmpR
<222> LOCATION: (121)..(981)
<220> FEATURE:
<221> NAME/KEY: LoxF9a
<222> LOCATION: (1042)..(1075)
<220> FEATURE:
<221> NAME/KEY: KanR
<222> LOCATION: (1172)..(1987)
<220> FEATURE:
<221> NAME/KEY: LoxF9b
<222> LOCATION: (2062)..(2095)
<220> FEATURE:
<221> NAME/KEY: R6K-ori
<222> LOCATION: (2328)..(2719)

<400> SEQUENCE: 22

```
tttcggggaa atgtgcgcgg aacccctatt tgtttatttt tctaaataca ttcaaatatg     60
tatccgctca tgagacaata accctgataa atgcttcaat aatattgaaa aaggaagagt    120
atgagtattc aacatttccg tgtcgccctt attcccttt ttgcggcatt ttgccttcct     180 gttttgctc acccagaaac gctggtgaaa gtaaaagatg ctgaagatca gttgggtgca    240
cgagtgggtt acatcgaact ggatctcaac agcggtaaga tccttgagag ttttcgcccc    300
gaagaacgtt ttccaatgat gagcactttt aaagttctgc tatgtggcgc ggtattatcc    360
cgtgttgacg ccgggcaaga gcaactcggt cgccgcatac actattctca gaatgacttg    420
gttgagtact caccagtcac agaaaagcat cttacggatg gcatgacagt aagagaatta    480
tgcagtgctg ccataaccat gagtgataac actgcggcca acttacttct gacaacgatc    540
ggaggaccga aggagctaac cgcttttttg cacaacatgg gggatcatgt aactcgcctt    600
gatcgttggg aaccggagct gaatgaagcc ataccaaacg acgagcgtga ccacgatg     660 cctgcagcaa tggcaacaac gttgcgcaaa ctattaactg gcgaactact tactctagct    720
tcccggcaac aattaataga ctggatggag gcggataaag ttgcaggacc acttctgcgc    780
tcggcccttc cggctggctg gtttattgct gataaatctg gagccggtga gcgtgggtct    840
```

```
cgcggtatca ttgcagcact ggggccagat ggtaagccct cccgtatcgt agttatctac      900
acgacgggga gtcaggcaac tatggatgaa cgaaatagac agatcgctga gataggtgcc      960
tcactgatta agcattggta acccagcccg cctaatgagc gggctttttt ttgaacaaaa     1020
ggctgcagct ggacttctag actcattaca tttaaccaaa attatcacaa tataaggtct     1080
gacgctcagt ggaacgaaaa ctcacgttaa gggattttgg tcatgaacaa taaaactgtc     1140
tgcttacata aacagtaata caaggggtgt tatgagccat attcaacggg aaacgtcttg     1200
ctctaggccg cgattaaatt ccaacatgga tgctgattta tatgggtata atgggctcg      1260 cgataatgtc gggcaatcag gtgcgacaat ctatcgattg tatgggaagc ccgatgcgcc     1320
agagttgttt ctgaaacatg gcaaaggtag cgttgccaat gatgttacag atgagatggt     1380
cagactaaac tggctgacgg aatttatgcc tcttccgacc atcaagcatt ttatccgtac     1440
tcctgatgat gcatggttac tcaccactgc gatccccggg aaaacagcat tccaggtatt     1500
agaagaatat cctgattcag gtgaaaatat tgttgatgcg ctggcagtgt tcctgcgccg     1560
gttgcattcg attcctgttt gtaattgtcc ttttaacagc gatcgcgtat ttcgtctcgc     1620
tcaggcgcaa tcacgaatga ataacggttt ggttgatgcg agtgattttg atgacgagcg     1680
taatggctgg cctgttgaac aagtctggaa agaaatgcat aaacttttgc cattctcacc     1740
ggattcagtc gtcactcatg gtgatttctc acttgataac cttattttg acgaggggaa      1800 attaataggt tgtattgatg ttggacgagt cggaatcgca gaccgatacc aggatcttgc     1860
catcctatgg aactgcctcg gtgagttttc tccttcatta cagaaacggc ttttttcaaaa    1920 atatggtgtt gataatcctg atatgaataa attgcagttt catttgatgc tcgatgagtt     1980
tttctaagaa ttaattcatg agcggataca tatttgaatg tatttagaaa ataaacaaa      2040 tagggggttcc gcgcacattt cccatctttt gttagatttg aatatataca ttctactcga    2100
gggtgcgaat aagggacatg aagaaggaac acccgctcgc gggtgggcct acttcaccta    2160
tcctgcccgg ctgacgccgt tggatacacc aaggaaagtc tacacgaacc ctttggcaaa    2220
atcctgtata tcgtgcgaaa aaggatggat ataccgaaaa aatcgctata atgaccccga    2280
agcagggtta tgcagcggaa aacggccacg atgcgtccgg cgtagaggat ctgaagatca    2340
gcagttcaac ctgttgatag tacgtactaa gctctcatgt ttcacgtact aagctctcat    2400
gtttaacgta ctaagctctc atgtttaacg aactaaaccc tcatggctaa cgtactaagc    2460
tctcatggct aacgtactaa gctctcatgt ttcacgtact aagctctcat gtttgaacaa    2520
taaaattaat ataatcagc aacttaaata gcctctaagg ttttaagttt tataagaaaa     2580
aaaagaatat ataaggcttt taaagctttt aaggtttaac ggttgtggac aacaagccag    2640
ggatgtaacg cactgagaag cccttagagc ctctcaaagc aatttgagt gacacaggaa      2700 cacttaacgg ctgacatggg aattagcttc acgctgccgc aagcactcag ggcgcaaggg    2760
ctgctaaagg aagcggatag acgtcaggtg gcact                               2795
```

<210> SEQ ID NO 23
<211> LENGTH: 19
<212> TYPE: DNA
<213> ORGANISM: Artificial Sequence
<220> FEATURE:
<223> OTHER INFORMATION: Primer P1 for amplifying the plasmid pDuoF9

<400> SEQUENCE: 23
ctctactgtt tctccatac                                                    19

```
<210> SEQ ID NO 24
<211> LENGTH: 17
<212> TYPE: DNA
<213> ORGANISM: Artificial Sequence
<220> FEATURE:
<223> OTHER INFORMATION: Primer P2 for amplifying the plasmid pDuoF9

<400> SEQUENCE: 24
agggaataag ggcgaca                                                   17

<210> SEQ ID NO 25
<211> LENGTH: 7463
<212> TYPE: DNA
<213> ORGANISM: Artificial Sequence
<220> FEATURE:
<223> OTHER INFORMATION: vector pDuoF9 product
<220> FEATURE:
<221> NAME/KEY: P1 binding site
<222> LOCATION: (1412)..(1430)
<220> FEATURE:
<221> NAME/KEY: Rec. F9-1 (placeholder)
<222> LOCATION: (1519)..(2550)
<220> FEATURE:
<221> NAME/KEY: Ribosome binding site
<222> LOCATION: (2551)..(2633)
<220> FEATURE:
<221> NAME/KEY: Rec. F9-2 (placeholder)
<222> LOCATION: (2634)..(3665)
<220> FEATURE:
<221> NAME/KEY: LoxF9a
<222> LOCATION: (4220)..(4253)
<220> FEATURE:
<221> NAME/KEY: KanR
<222> LOCATION: (4350)..(5165)
<220> FEATURE:
<221> NAME/KEY: LoxF9b
<222> LOCATION: (5240)..(5273)
<220> FEATURE:
<221> NAME/KEY: P2 binding site
<222> LOCATION: (5291)..(5307)
<220> FEATURE:
<221> NAME/KEY: CmR
<222> LOCATION: (5594)..(6253)
<220> FEATURE:
<221> NAME/KEY: Ori
<222> LOCATION: (6615)..(7463)

<400> SEQUENCE: 25
gctcatgagc cgaagtggcg gagcccgatc ttccccatcg gtgatgtcgg cgatataggc      60
gccagcaacc gcacctgtgg cgccggtgat gccggccacg atgcgtccgg cgtagaggat     120
ctgctcatgt ttgacagctt atcatcgatg cataatgtgc ctgtcaaatg gacgaagcag     180
ggattctgca aaccctatgc tactccgtca agccgtcaat tgtctgattc gttaccaatt     240
atgacaactt gacggctaca tcattcactt tttcttcaca accggcacgg aactcgctcg     300
ggctggcccc ggtgcatttt ttaaataccc gcgagaaata gagttgatcg tcaaaaccaa     360
cattgcgacc gacggtggcg ataggcatcc gggtggtgct caaaagcagc ttcgcctggc     420
tgatacgttg gtcctcgcgc cagcttaaga cgctaatccc taactgctgg cggaaaagat     480
gtgacagacg cgacggcgac aagcaaacat gctgtgcgac gctggcgata tcaaaattgc     540
tgtctgccag gtgatcgctg atgtactgac aagcctcgcg tacccgatta tccatcggtg     600
gatggagcga ctcgttaatc gcttccatgc gccgcagtaa caattgctca agcagattta     660
tcgccagcag ctccgaatag cgcccttccc cttgcccggc gttaatgatt tgcccaaaca     720
ggtcgctgaa atgcggctgg tgcgcttcat ccggcgaaaa gaaccccgta ttggcaaata     780
ttgacggcca gttaagccat tcatgccagt aggcgcgcgg acgaaagtaa acccactggt     840
```

```
gataccattc gcgagcctcc ggatgacgac cgtagtgatg aatctctcct ggcgggaaca    900
gcaaaatatc acccggtcgg caaacaaatt ctcgtccctg atttttcacc accccctgac    960
cgcgaatggt gagattgaga atataacctt tcattcccag cggtcggtcg ataaaaaaat   1020
cgagataacc gttggcctca atcggcgtta aacccgccac cagatgggca ttaaacgagt   1080
atcccggcag caggggatca ttttgcgctt cagccatact tttcatactc ccgccattca   1140
gagaagaaac caattgtcca tattgcatca gacattgccg tcactgcgtc ttttactggc   1200
tcttctcgct aaccaaaccg gtaaccccgc ttattaaaag cattctgtaa caaagcggga   1260
ccaaagccat gacaaaaacg cgtaacaaaa gtgtctataa tcacggcaga aaagtccaca   1320
ttgattattt gcacggcgtc acactttgct atgccatagc attttatcc ataagattag    1380
cggatcctac ctgacgcttt ttatcgcaac tctctactgt ttctccatac ccgtttttt    1440
gggctagcga attcgagctc taaggaggtg ccacaattct cgagccatac ccattctaat   1500
gatcataagg aggtgtacat gtcaatacta ctgaccttgc accaaagttt gtccgcatta   1560
ctggtcgatg caacgagtga tgaggctcgc aagaacctga tggatgtgct cagggatcgc   1620
caggcgttct ccgagcgtac ctggaaagtg ctcctgtccg tttgccggac gtgggcggca   1680
tggtgcaagt tgaacaaccg gaaatggttt cccgcggaac ctgaagatgt tcgcgattac   1740
cttctacatc ttcaggctcg cggtctggca gtaaacacta tcctgcaaca tttgcccag    1800
ctaaacatgc tccaccgtcg gttcgggctg ccacgaccgg gcgacagcga cgctgtttca   1860
ctggttatgc ggcgaatccg aagggagaac gtcgatgctg gtgagcgtac caagcaggcc   1920
ctagcgttcg agcgcactga cttcgaccag gttcgtgcac tcatggaaaa tagcgaacgg   1980
ggccaggata tacgtactct ggcacttctg ggggttgctt ataacaccct gttacgcgta   2040
tccgaaattg ccaggattcg gattaaagac atctcacgta ctgacggtgg gaggatgcta   2100
atccacatta gcagaacgaa aacgctggtc agcaccgcag gcgtagagaa ggcgcttagc   2160
ctgggggtaa ctaaactggt cgagcgatgg atttccgtct ctggtgtggc tagtgaccca   2220
aacaattacc tgttttgcca ggttagaata aatggtgtgg ccgtgccgtc tgccaccagc   2280
cggctatcaa ccgacgtcct gcgaaagatt tttgaggctg cccaccgcct gatctacggt   2340
gccaaggatg gctctggtca gagatacctg gcctggtctg ggcacagtgc ccgtgtcgga   2400
gccgcgcggg atatgcccg cgctgggtt tcaatagcgg agattatgca ggctggtggc     2460
tggaccaccg tagagagtgt catgaactat atccgtaacc tggacagtga gacaggggca   2520
atggtgcgtc tgctggaaga tggcgactag tctagaggta ccattccgat cgcggatcgg   2580
ccggaatggg atagacgtcc tatcatccac acctactagt taaggaggtg tacatgtcaa   2640
tactactgac cttgcaccaa agtttgtccg cattactggt cgatgcaacg agtgatgagg   2700
ctcgcaagaa cctgatggat gtgctcaggg atcgccaggc gttctccgag cgtacctgga   2760
aagtgctcct gtccgtttgc cggacgtggg cggcatggtg caagttgaac aaccggaaat   2820
ggtttcccgc ggaacctgaa gatgttcgcg attaccttct acatcttcag gctcgcggtc   2880
tggcagtaaa cactatcctg caacatttgg cccagctaaa catgctccac cgtcggttcg   2940
ggctgccacg accgggcgac agcgacgctg tttcactggt tatgcggcga atccgaaggg   3000
agaacgtcga tgctggtgag cgtaccaagc aggccctagc gttcgagcgc actgacttcg   3060
accaggttcg tgcactcatg gaaaatagc aacgggcca ggatatacgt actctggcac    3120
ttctgggggt tgcttataac accctgttac gcgtatccga aattgccagg attcggatta   3180
```

```
aagacatctc acgtactgac ggtgggagga tgctaatcca cattagcaga acgaaaacgc   3240
tggtcagcac cgcaggcgta gagaaggcgc ttagcctggg ggtaactaaa ctggtcgagc   3300
gatggatttc cgtctctggt gtggctagtg acccaaacaa ttacctgttt tgccaggtta   3360
gaataaatgg tgtggccgtg ccgtctgcca ccagccggct atcaaccgac gtcctgcgaa   3420 agattttga ggctgcccac cgcctgatct acggtgccaa ggatggctct ggtcagagat    3480
acctggcctg gtctgggcac agtgcccgtg tcggagccgc gcgggatatg gcccgcgctg   3540
gggtttcaat agcggagatt atgcaggctg gtggctggac caccgtagag agtgtcatga   3600
actatatccg taacctggac agtgagacag gggcaatggt gcgtctgctg gaagatggcg   3660
actagtctag acgtacgcct gcaggcaagc ttggctgttt tggcggatga gagaagattt   3720
tcagcctgat acagattaaa tcagaacgca gaagcggtct gataaaacag aatttgcctg   3780
gcggcagtag cgcggtggtc ccacctgacc ccatgccgaa ctcagaagtg aaacgccgta   3840
gcgccgatgg tagtgtgggg tctccccatg cgagagtagg gaactgccag gcatcaaata   3900
aaacgaaagg ctcagtcgaa agactgggcc tttcgtttta tctgttgttt gtcggtgaac   3960
gctctcctga gtaggacaaa tccgccggga gcggatttga acgttgcgaa gcaacggccc   4020
ggagggtggc gggcaggacg cccgccataa actgccaggc atcaaattaa gcagaaggcc   4080
atcctgacgg atggcctttt tgcgtttcta caaactcttt tgtttatttt tctaaataca   4140
ttcaaatatg tatccgctca tgagacaata accctgataa atgcttcaat aatattgaaa   4200
aaggaagagt atgagatctc tcattacatt taaccaaaat tatcacaata taaggtctga   4260
cgctcagtgg aacgaaaact cacgttaagg gattttggtc atgaacaata aaactgtctg   4320
cttacataaa cagtaataca aggggtgtta tgagccatat tcaacgggaa acgtcttgct   4380
ctaggccgcg attaaattcc aacatggatg ctgatttata tgggtataaa tgggctcgcg   4440
ataatgtcgg gcaatcaggt gcgacaatct atcgattgta tgggaagccc gatgcgccag   4500
agttgtttct gaaacatggc aaaggtagcg ttgccaatga tgttacagat gagatggtca   4560
gactaaactg gctgacggaa tttatgcctc ttccgaccat caagcatttt atccgtactc   4620
ctgatgatgc atggttactc accactgcga tccccgggaa aacagcattc caggtattag   4680
aagaatatcc tgattcaggt gaaaatattg ttgatgcgct ggcagtgttc ctgcgccggt   4740
tgcattcgat tcctgtttgt aattgtcctt ttaacagcga tcgcgtattt cgtctcgctc   4800
aggcgcaatc acgaatgaat aacggtttgg ttgatgcgag tgattttgat gacgagcgta   4860
atggctggcc tgttgaacaa gtctggaaag aaatgcataa acttttgcca ttctcaccgg   4920
attcagtcgt cactcatggt gatttctcac ttgataacct tattttgac gaggggaaat    4980 taataggttg tattgatgtt ggacgagtcg gaatcgcaga ccgataccag gatcttgcca   5040
tcctatggaa ctgcctcggt gagttttctc cttcattaca gaaacggctt tttcaaaaat   5100
atggtgttga taatcctgat atgaataaat tgcagtttca tttgatgctc gatgagtttt   5160
tctaagaatt aattcatgag cggatacata tttgaatgta tttagaaaaa taaacaaata   5220
ggggttccgc gcacatttcc catcttttgt tagatttgaa tatatacatt ctaagatctc   5280
aacatttccg tgtcgccctt attcccttt tgcggcatt tgccttcct gttttgctc     5340 acccagaaac gctggtgaaa gtaaaagatg ctgaagatca gttgggtgca gcaaactatt   5400
aactggcgaa ctacttactc tagcttcccg gcaacaatta atagactgga tggaggcgga   5460
taaagttgca ggaccacttc tgcgctcggc ccggtcgaat ttgctttcga atttctgcca   5520
ttcatccgct tattatcact tattcaggcg tagcaccagg cgtttaaggg caccaataac   5580
```

```
tgccttaaaa aaattacgcc ccgccctgcc actcatcgca gtactgttgt aattcattaa    5640
gcattctgcc gacatggaag ccatcacaga cggcatgatg aacctgaatc gccagcggca    5700
tcagcacctt gtcgccttgc gtataatatt tgcccatggt gaaaacgggg gcgaagaagt    5760
tgtccatatt ggccacgttt aaatcaaaac tggtgaaact cacccaggga ttggctgaga    5820
cgaaaaacat attctcaata aacccttttag ggaaataggc caggttttca ccgtaacacg    5880
ccacatcttg cgaatatatg tgtagaaact gccggaaatc gtcgtggtat tcactccaga    5940
gcgatgaaaa cgtttcagtt tgctcatgga aaacggtgta acaagggtga acactatccc    6000
atatcaccag ctcaccgtct ttcattgcca tacgaattc cggatgagca ttcatcaggc    6060
gggcaagaat gtgaataaag gccggataaa acttgtgctt attttctttt acggtcttta    6120
aaaaggccgt aatatccagc tgaacggtct ggttataggt acattgagca actgactgaa    6180
atgcctcaaa atgttcttta cgatgccatt gggatatatc aacgtggtta tatccagtga    6240
tttttttctc cattttagct tccttagctc ctgaaaatct cgataactca aaaaatacgc    6300
ccggtagtga tcttatttca ttatggtgaa agttggaacc tcttacgtgc cgatcaacgt    6360 ctcatttttcg ccaaaagttg gcccaggggct tcccggtatc aacagggaca ccaggattta    6420
tttattctgc gaagtgatct tccgtcacag gtatttattc ggcgcaaagt gcgtcgggtg    6480
atgctgccaa cttactgatt tagtgtatga tggtgttttt gaggtgctcc agtggcttct    6540
gtttctatca gctgtccctc ctgttcagct actgacgggg tggtgcgtaa cggcaaaagc    6600
accgccggac atcagcgcta gcggagtgta tactggctta ctatgttggc actgatgagg    6660
gtgtcagtga agtgcttcat gtggcaggag aaaaaaggct gcaccggtgc gtcagcagaa    6720
tatgtgatac aggatatatt ccgcttcctc gctcactgac tcgctacgct cggtcgttcg    6780
actgcggcga gcggaaatgg cttacgaacg gggcggagat ttcctggaag atgccaggaa    6840
gatacttaac agggaagtga gagggccgcg gcaaagccgt ttttccatag gctccgcccc    6900
cctgacaagc atcacgaaat ctgacgctca aatcagtggt ggcgaaaccc gacaggacta    6960
taaagatacc aggcgtttcc ccctggcggc tccctcgtgc gctctcctgt tcctgccttt    7020
cggtttaccg gtgtcattcc gctgttatgg ccgcgtttgt ctcattccac gcctgacact    7080
cagttccggg taggcagttc gctccaagct ggactgtatg cacgaacccc ccgttcagtc    7140
cgaccgctgc gccttatccg gtaactatcg tcttgagtcc aacccggaaa gacatgcaaa    7200
agcaccactg gcagcagcca ctggtaattg atttagagga gttagtcttg aagtcatgcg    7260
ccggttaagg ctaaactgaa aggacaagtt ttggtgactg cgctcctcca gccagttac    7320 ctcggttcaa agagttggta gctcagagaa ccttcgaaaa accgccctgc aaggcggttt    7380
tttcgttttc agagcaagag attacgcgca gaccaaaacg atctcaagaa gatcatctta    7440
ttaatcagat aaaatatttc tag                                           7463
```

<210> SEQ ID NO 26
<211> LENGTH: 800
<212> TYPE: DNA
<213> ORGANISM: Homo sapiens
<220> FEATURE:
<221> NAME/KEY: loxF9a
<222> LOCATION: (1)..(34)
<220> FEATURE:
<221> NAME/KEY: loxF9b
<222> LOCATION: (766)..(800)
<220> FEATURE:
<221> NAME/KEY: Exon 8 of the F9 gene wildtype
<222> LOCATION: (766)..(800)

<400> SEQUENCE: 26

```
ctcattacat ttaaccaaaa ttatcacaat ataagaatga gatctttaac attgccaatt    60
aggtcagtgg tcccaagtag tcacttagaa aatctgtgta tgtgaaatac tgtttgtgac   120
ttaaaatgaa atttattttt aataggtgaa cataatattg aggagacaga acatacagag   180
caaaagcgaa atgtgattcg aattattcct caccacaact acaatgcagc tattaataag   240
tacaaccatg acattgccct tctggaactg gacgaaccct tagtgctaaa cagctacgtt   300
acacctattt gcattgctga caaggaatac acgaacatct tcctcaaatt tggatctggc   360
tatgtaagtg gctggggaag agtcttccac aaagggagat cagctttagt tcttcagtac   420
cttagagttc cacttgttga ccgagccaca tgtcttcgat ctacaaagtt caccatctat   480
aacaacatgt tctgtgctgg cttccatgaa ggaggtagag attcatgtca aggagatagt   540
gggggacccc atgttactga agtggaaggg accagtttct taactggaat tattagctgg   600
ggtgaagagt gtgcaatgaa aggcaaatat ggaatatata ccaaggtatc ccggtatgtc   660
aactggatta aggaaaaaac aaagctcact taatgaaaga tggatttcca aggttaattc   720
attggaattg aaaattaaca gggcctctca ctaactaatc actttcccat cttttgttag   780
atttgaatat atacattcta                                               800
```

<210> SEQ ID NO 27
<211> LENGTH: 800
<212> TYPE: DNA
<213> ORGANISM: Homo sapiens
<220> FEATURE:
<221> NAME/KEY: loxF9a
<222> LOCATION: (1)..(34)
<220> FEATURE:
<221> NAME/KEY: Exon 8 of the F9 gene Arg338Leu (Padua mutation)
<222> LOCATION: (146)..(693)
<220> FEATURE:
<221> NAME/KEY: LoxF9b
<222> LOCATION: (766)..(800)

<400> SEQUENCE: 27

```
ctcattacat ttaaccaaaa ttatcacaat ataagaatga gatctttaac attgccaatt    60
aggtcagtgg tcccaagtag tcacttagaa aatctgtgta tgtgaaatac tgtttgtgac   120
ttaaaatgaa atttattttt aataggtgaa cataatattg aggagacaga acatacagag   180
caaaagcgaa atgtgattcg aattattcct caccacaact acaatgcagc tattaataag   240
tacaaccatg acattgccct tctggaactg gacgaaccct tagtgctaaa cagctacgtt   300
acacctattt gcattgctga caaggaatac acgaacatct tcctcaaatt tggatctggc   360
tatgtaagtg gctggggaag agtcttccac aaagggagat cagctttagt tcttcagtac   420
cttagagttc cacttgttga ccgagccaca tgtcttctgt ctacaaagtt caccatctat   480
aacaacatgt tctgtgctgg cttccatgaa ggaggtagag attcatgtca aggagatagt   540
gggggacccc atgttactga agtggaaggg accagtttct taactggaat tattagctgg   600
ggtgaagagt gtgcaatgaa aggcaaatat ggaatatata ccaaggtatc ccggtatgtc   660
aactggatta aggaaaaaac aaagctcact taatgaaaga tggatttcca aggttaattc   720
attggaattg aaaattaaca gggcctctca ctaactaatc actttcccat cttttgttag   780
atttgaatat atacattcta                                               800
```

<210> SEQ ID NO 28
<211> LENGTH: 343

```
<212> TYPE: PRT
<213> ORGANISM: Artificial Sequence
<220> FEATURE:
<223> OTHER INFORMATION: Recombinase F9-1
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (68)..(69)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (182)..(183)
<223> OTHER INFORMATION: Xaa can be any naturally occurring amino acid
<220> FEATURE:
<221> NAME/KEY: misc_feature
<222> LOCATION: (186)..(186)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (225)..(225)
```

```
<223> OTHER INFORMATION: Xaa can be any naturally occurring amino acid
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (259)..(260)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (284)..(284)
<223> OTHER INFORMATION: Xaa can be any naturally occurring amino acid
<220> FEATURE:
<221> NAME/KEY: misc_feature
<222> LOCATION: (318)..(318)
<223> OTHER INFORMATION: Xaa can be any naturally occurring amino acid
<220> FEATURE:
<221> NAME/KEY: misc_feature
<222> LOCATION: (342)..(342)
<223> OTHER INFORMATION: Xaa can be any naturally occurring amino acid

<400> SEQUENCE: 28

Met Ser Asn Leu Gln Thr Leu His Gln Asn Leu Ser Ala Leu Leu Val
1               5                   10                  15

Xaa Ala Xaa Ser Asp Xaa Ala Arg Lys Asn Leu Met Asp Xaa Phe Arg
            20                  25                  30

Asp Arg Gln Ala Phe Ser Glu His Thr Trp Xaa Val Leu Leu Ser Val
        35                  40                  45

Cys Arg Ser Trp Ala Ala Trp Cys Lys Leu Asn Xaa Arg Lys Trp Phe
    50                  55                  60

Pro Ala Glu Xaa Xaa Asp Val Arg Asp Tyr Leu Leu His Leu Gln Ala
65                  70                  75                  80

Xaa Gly Leu Xaa Val Asn Thr Ile Xaa Gln His Leu Xaa Gln Leu Asn
            85                  90                  95

Met Leu His Arg Arg Ser Gly Leu Pro Arg Pro Gly Asp Ser Asn Ala
            100                 105                 110

Val Ser Leu Val Met Arg Arg Ile Arg Lys Glu Asn Val Asp Ala Gly
            115                 120                 125

Glu Arg Val Lys Gln Ala Leu Ala Phe Glu Arg Xaa Asp Phe Asp Gln
130                 135                 140

Val Arg Ser Leu Met Glu Asn Ser Asp Arg Cys Gln Asp Ile Arg Asn
145                 150                 155                 160

Leu Ala Phe Leu Gly Xaa Ala Tyr Asn Thr Leu Leu Arg Ile Ser Glu
                165                 170                 175

Xaa Ala Arg Ile Arg Xaa Xaa Asp Ile Xaa Arg Thr Asp Gly Gly Arg
            180                 185                 190

Met Leu Ile His Ile Gly Arg Thr Lys Thr Leu Val Ser Xaa Ala Gly
            195                 200                 205
```

Val Glu Lys Ala Leu Ser Leu Arg Val Thr Arg Leu Val Xaa Arg Trp
    210                 215                 220

Xaa Ser Val Ser Gly Val Ala Asp Asp Pro Asn Asn Xaa Leu Xaa Cys
225                 230                 235                 240

Arg Val Arg Arg Asn Gly Val Ala Xaa Pro Ser Ala Thr Ser Gln Leu
                245                 250                 255

Ser Thr Xaa Xaa Leu Gln Gly Xaa Phe Ala Ala His Arg Leu Ile
            260                 265                 270

Tyr Gly Ala Arg Asp Xaa Ser Gly Gln Arg Tyr Xaa Thr Trp Ser Gly
                275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Xaa Glu Ser
305                 310                 315                 320

Val Met Asn Tyr Ile Arg Asn Leu Asp Ser Glu Thr Gly Ala Met Val
                325                 330                 335

Arg Leu Leu Glu Asp Xaa Asp
            340

<210> SEQ ID NO 29
<211> LENGTH: 343
<212> TYPE: PRT
<213> ORGANISM: Artificial Sequence
<220> FEATURE:
<223> OTHER INFORMATION: Recombinase F9-1
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:

```
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (182)..(183)
<223> OTHER INFORMATION: Xaa can be any naturally occurring amino acid
<220> FEATURE:
<221> NAME/KEY: misc_feature
<222> LOCATION: (186)..(186)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (259)..(260)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (276)..(276)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (306)..(306)
<223> OTHER INFORMATION: Xaa can be any naturally occurring amino acid
<220> FEATURE:
<221> NAME/KEY: misc_feature
<222> LOCATION: (325)..(325)
<223> OTHER INFORMATION: Xaa can be any naturally occurring amino acid

<400> SEQUENCE: 29

Met Ser Xaa Leu Xaa Thr Leu Xaa Gln Asn Leu Ser Ala Xaa Leu Xaa
1               5                   10                  15

Asp Xaa Xaa Xaa Xaa Glu Ala Arg Lys Asn Leu Met Asp Val Xaa Arg
            20                  25                  30
```

Asp Arg Gln Ala Phe Ser Xaa His Thr Trp Arg Val Leu Leu Ser Val
            35                  40                  45

Cys Arg Ser Trp Ala Ala Trp Cys Glu Leu Asn Asn Arg Lys Trp Phe
 50                  55                  60

Pro Ala Glu Pro Glu Asp Val Arg Asp Tyr Leu Leu His Leu Gln Xaa
 65                  70                  75                  80

Arg Gly Leu Xaa Val Asn Thr Ile Gln Gln His Leu Xaa Gln Leu Asn
                85                  90                  95

Xaa Leu His Arg Arg Ser Gly Leu Pro Arg Pro Gly Asp Ser Asn Ala
            100                 105                 110

Val Ser Leu Val Met Arg Arg Ile Arg Lys Glu Asn Xaa Asp Ala Gly
            115                 120                 125

Glu Arg Val Xaa Gln Ala Leu Ala Phe Glu Arg Thr Asp Phe Asp Gln
            130                 135                 140

Val Arg Ser Leu Met Glu Asn Ser Asp Arg Cys Gln Asp Ile Arg Asn
145                 150                 155                 160

Leu Ala Phe Leu Gly Val Ala Tyr Asn Thr Leu Leu Arg Ile Ser Glu
                165                 170                 175

Ile Ala Arg Ile Arg Xaa Xaa Asp Ile Xaa Arg Thr Asp Gly Gly Arg
            180                 185                 190

Met Leu Xaa His Ile Gly Arg Thr Lys Thr Leu Val Ser Xaa Ala Gly
            195                 200                 205

Val Glu Lys Ala Leu Ser Leu Xaa Val Thr Lys Leu Val Glu Arg Trp
            210                 215                 220

Ile Ser Val Ser Gly Val Ala Asp Pro Asn Asn Tyr Leu Phe Cys
225                 230                 235                 240

Arg Val Arg Arg Asn Gly Val Ala Xaa Pro Ser Ala Xaa Ser Gln Leu
                245                 250                 255

Ser Thr Xaa Xaa Leu Gln Gly Xaa Phe Xaa Ala Ala His Arg Leu Ile
            260                 265                 270

Xaa Gly Ala Xaa Asp Xaa Ser Gly Gln Arg Tyr Leu Thr Trp Ser Gly
            275                 280                 285

His Ser Ala Arg Val Gly Ala Ala Arg Asp Met Ala Arg Ala Gly Val
            290                 295                 300

Ser Xaa Ala Glu Ile Met Gln Ala Gly Gly Trp Thr Thr Val Glu Ser
305                 310                 315                 320

Val Met Asn Tyr Xaa Arg Asn Leu Asp Ser Glu Thr Gly Ala Met Val
                325                 330                 335

Arg Leu Leu Glu Asp Gly Asp
            340

<210> SEQ ID NO 30
<211> LENGTH: 20
<212> TYPE: DNA
<213> ORGANISM: Artificial Sequence
<220> FEATURE:
<223> OTHER INFORMATION: Primer P1# for amplifying the plasmid pDuoF9

<400> SEQUENCE: 30
cggcgtcaca ctttgctatg                                                 20

<210> SEQ ID NO 31
<211> LENGTH: 20
<212> TYPE: DNA
<213> ORGANISM: Artificial Sequence
<220> FEATURE:

-continued

<223> OTHER INFORMATION: Primer P2# for amplifying the plasmid pDuoF9

<400> SEQUENCE: 31
cccttaaacg cctggtgcta                                        20

<210> SEQ ID NO 32
<211> LENGTH: 20
<212> TYPE: DNA
<213> ORGANISM: Artificial Sequence
<220> FEATURE:
<223> OTHER INFORMATION: Primer P3 for amplifying the recombinase
      library

<400> SEQUENCE: 32
aagattagcg gatcctacct                                        20

<210> SEQ ID NO 33
<211> LENGTH: 20
<212> TYPE: DNA
<213> ORGANISM: Artificial Sequence
<220> FEATURE:
<223> OTHER INFORMATION: Primer P4 for amplifying the recombinase
      library

<400> SEQUENCE: 33
gtgattagtt agtgagaggc                                        20

<210> SEQ ID NO 34
<211> LENGTH: 343
<212> TYPE: PRT
<213> ORGANISM: Artificial Sequence
<220> FEATURE:
<223> OTHER INFORMATION: Recombinase R#1

<400> SEQUENCE: 34

Met Ser Lys Leu Gln Thr Ile His Gln Asn Leu Ser Ala Leu Leu Val
1               5                   10                  15

Asp Ala Thr Ser Asp Glu Ala Arg Lys Asn Leu Met Asp Val Leu Arg
            20                  25                  30

Asp Arg Gln Ala Phe Ser Lys His Thr Trp Arg Val Leu Leu Ser Val
        35                  40                  45

Cys Arg Ser Trp Ala Ala Trp Cys Glu Leu Asn Asn Arg Lys Trp Phe
    50                  55                  60

Pro Ala Glu Pro Glu Asp Val Arg Asp Tyr Leu Leu His Leu Gln Thr
65                  70                  75                  80

Arg Gly Leu Thr Val Asn Thr Ile Gln Gln His Leu Cys Gln Leu Asn
                85                  90                  95

Leu Leu His Arg Arg Ser Gly Leu Pro Arg Pro Gly Asp Ser Asn Ala
            100                 105                 110

Val Ser Leu Val Met Arg Arg Ile Arg Lys Glu Asn Ile Asp Ala Gly
        115                 120                 125

Glu Arg Val Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Thr Arg Thr Asp Gly Gly Arg
            180                 185                 190

Met Leu Ile His Ile Gly Arg Thr Lys Thr Leu Val Ser Ala Ala Gly

```
                195                 200                 205
Val Glu Lys Ala Leu Ser Leu Gly Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Arg Val Arg Arg Asn Gly Val Ala Ala Pro Ser Ala Ile Ser Gln Leu
                245                 250                 255

Ser Thr Pro Ala Leu Gln Gly Val Phe Ala Ala His Arg Leu Ile
                260                 265                 270

His Gly Ala Lys Asp Ala Ser Gly Gln Arg Tyr Leu Thr Trp Ser Gly
                275                 280                 285

His Ser Ala Arg Val Gly Ala Ala Arg Asp Met Ala Arg Ala Gly Val
                290                 295                 300

Ser Val Ala Glu Ile Met Gln Ala Gly Gly Trp Thr Thr Val Glu Ser
305                 310                 315                 320

Val Met Asn Tyr Leu Arg Asn Leu Asp Ser Glu Thr Gly Ala Met Val
                325                 330                 335

Arg Leu Leu Glu Asp Gly Asp
                340

<210> SEQ ID NO 35
<211> LENGTH: 343
<212> TYPE: PRT
<213> ORGANISM: Artificial Sequence
<220> FEATURE:
<223> OTHER INFORMATION: Recombinase R#7-B5

<400> SEQUENCE: 35

Met Ser Lys Leu Gln Thr Ile His Gln Asp Leu Ser Ala Leu Leu Val
1               5                   10                  15

Asp Val Thr Ser Asp Glu Ala Arg Lys Asn Leu Met Asp Val Leu Arg
                20                  25                  30

Asp Arg Gln Ala Phe Ser Lys His Thr Trp Arg Val Leu Leu Ser Val
                35                  40                  45

Cys Arg Ser Trp Ala Ala Trp Cys Glu Leu Asn Asn Arg Lys Trp Phe
50                  55                  60

Pro Ala Glu Pro Glu Asp Val Arg Asp Tyr Leu Leu His Leu Gln Thr
65                  70                  75                  80

Arg Gly Leu Thr Val Asn Thr Ile Gln Gln His Leu Cys Gln Leu Asn
                85                  90                  95

Leu Leu His Arg Arg Ser Gly Leu Pro Arg Pro Gly Asp Ser Asn Ala
                100                 105                 110

Val Ser Leu Val Met Arg Arg Ile Arg Lys Glu Asn Ile Asp Ala Gly
                115                 120                 125

Glu Arg Val Lys Gln Ala Leu Ala Phe Glu Arg Thr Asp Phe Asp Gln
130                 135                 140

Val Arg Ser Leu Met Glu Asn Ser Asp Arg Cys Gln Asp Ile Arg Asn
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Thr Arg Thr Asp Gly Gly Arg
                180                 185                 190

Met Leu Ile His Ile Gly Arg Thr Lys Thr Leu Val Ser Ala Ala Gly
                195                 200                 205

Val Glu Lys Ala Leu Ser Leu Gly Val Thr Lys Leu Val Glu Arg Trp
```

```
            210                 215                 220
Ile Ser Val Ser Gly Val Ala Asp Asp Pro Asn Asn His Leu Phe Cys
225                 230                 235                 240

Arg Val Arg Arg Asn Gly Val Ala Ala Pro Ser Ala Ile Ser Gln Leu
                245                 250                 255

Ser Thr Pro Ala Leu Gln Gly Val Phe Ala Ala His Arg Leu Ile
                260                 265                 270

His Gly Ala Lys Asp Ala Ser Gly Gln Arg Tyr Leu Thr Trp Ser Gly
                275                 280                 285

His Ser Ala Arg Val Gly Ala Ala Arg Asp Met Ala Arg Ala Gly Val
                290                 295                 300

Ser Val Ala Glu Ile Met Gln Ala Gly Gly Trp Thr Thr Val Glu Ser
305                 310                 315                 320

Val Met Asn Tyr Leu Arg Asn Leu Asp Ser Glu Thr Gly Ala Met Val
                325                 330                 335

Arg Leu Leu Glu Asp Gly Asp
                340

<210> SEQ ID NO 36
<211> LENGTH: 343
<212> TYPE: PRT
<213> ORGANISM: Artificial Sequence
<220> FEATURE:
<223> OTHER INFORMATION: Recombinase F9-3

<400> SEQUENCE: 36

Met Pro Lys Leu Gln Thr Ile His Gln Asp Leu Ser Ala Leu Leu Val
1               5                   10                  15

Asp Val Thr Ser Asp Glu Ala Arg Lys Asn Leu Met Asp Val Leu Arg
                20                  25                  30

Asp Arg Gln Ala Phe Ser Arg His Thr Trp Arg Val Leu Leu Ser Val
                35                  40                  45

Cys Arg Ser Trp Ala Ala Trp Cys Glu Leu Asn Asn Arg Lys Trp Phe
            50                  55                  60

Pro Ala Glu Pro Glu Asp Val Arg Asp Tyr Leu Leu Gln Leu Gln Thr
65              70                  75                  80

Arg Gly Leu Thr Val Asn Thr Ile Gln Gln His Leu Cys Gln Leu Asn
                85                  90                  95

Leu Leu His Arg Arg Ser Gly Leu Pro Arg Pro Gly Asp Ser Asn Ala
                100                 105                 110

Val Ser Leu Val Met Arg Arg Ile Arg Lys Glu Asn Ile Asp Ala Gly
            115                 120                 125

Glu Arg Val Lys Gln Ala Leu Ala Phe Glu Arg Thr Asp Phe Asp Gln
            130                 135                 140

Val Arg Ser Leu Met Glu Asn Ser Asp Arg Cys Gln Asp Ile Arg Asn
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Thr Arg Thr Asp Gly Gly Arg
                180                 185                 190

Met Leu Ile His Ile Gly Ile Thr Lys Thr Leu Val Ser Ala Ala Gly
                195                 200                 205

Val Glu Lys Ala Leu Ser Leu Gly Val Thr Lys Leu Val Glu Arg Trp
            210                 215                 220

Ile Ser Val Ser Gly Val Ala Asp Asp Pro Asn Asn His Leu Phe Cys
```

```
        225                 230                 235                 240
Arg Val Arg Arg Asn Gly Val Ala Ala Pro Ser Ala Ile Ser Gln Leu
                245                 250                 255

Ser Thr Pro Ala Leu Gln Gly Val Phe Ala Ala His Arg Leu Ile
            260                 265                 270

His Gly Ala Lys Asp Asp Ser Gly Gln Arg Tyr Leu Thr Trp Ser Gly
                275                 280                 285

His Ser Ala Arg Val Gly Ala Ala Arg Asp Met Ala Arg Ala Gly Val
            290                 295                 300

Pro Val Ala Glu Ile Met Gln Ala Gly Gly Trp Thr Thr Val Glu Ser
305                 310                 315                 320

Val Met Ser Tyr Leu Arg Asn Leu Asp Ser Glu Thr Gly Ala Met Val
                325                 330                 335

Arg Leu Leu Glu Asp Gly Asp
            340

<210> SEQ ID NO 37
<211> LENGTH: 4930
<212> TYPE: DNA
<213> ORGANISM: Artificial Sequence
<220> FEATURE:
<223> OTHER INFORMATION: Plasmid pDonor-ex8
<220> FEATURE:
<221> NAME/KEY: Origin of replication
<222> LOCATION: (167)..(786)
<220> FEATURE:
<221> NAME/KEY: AmpR
<222> LOCATION: (941)..(1801)
<220> FEATURE:
<221> NAME/KEY: KanR
<222> LOCATION: (1822)..(2610)
<220> FEATURE:
<221> NAME/KEY: part of human F9 gene including exon 8
<222> LOCATION: (3638)..(4636)
<220> FEATURE:
<221> NAME/KEY: LoxF9a
<222> LOCATION: (3713)..(3746)
<220> FEATURE:
<221> NAME/KEY: LoxF9b
<222> LOCATION: (4479)..(4512)
<220> FEATURE:
<221> NAME/KEY: P4 binding site
<222> LOCATION: (4479)..(4512)

<400> SEQUENCE: 37
cttccgcttc ctcgctcact gactcgctgc gctcggtcgt tcggctgcgg cgagcggtat      60
cagctcactc aaaggcggta atacggttat ccacagaatc aggggataac gcaggaaaga    120
acatgtgagc aaaaggccag caaaaggcca ggaaccgtaa aaaggccgcg ttgctggcgt    180
ttttccatag gctccgcccc cctgacgagc atcacaaaaa tcgacgctca agtcagaggt    240
ggcgaaaccc gacaggacta taaagatacc aggcgtttcc ccctggaagc tccctcgtgc    300
gctctcctgt tccgaccctg ccgcttaccg gatacctgtc cgcctttctc ccttcgggaa    360
gcgtggcgct ttctcatagc tcacgctgta ggtatctcag ttcggtgtag gtcgttcgct    420
ccaagctggg ctgtgtgcac gaaccccccg ttcagcccga ccgctgcgcc ttatccggta    480
actatcgtct tgagtccaac ccggtaagac acgacttatc gccactggca gcagccactg    540
gtaacaggat tagcagagcg aggtatgtag gcggtgctac agagttcttg aagtggtggc    600
ctaactacgg ctacactaga agaacagtat ttggtatctg cgctctgctg aagccagtta    660
ccttcggaaa aagagttggt agctcttgat ccggcaaaca aaccaccgct ggtagcggtg    720
gtttttttgt ttgcaagcag cagattacgc gcagaaaaaa aggatctcaa gaagatcctt    780
```

```
tgatcttttc tacggggtct gacgctcagt ggaacgaaaa ctcacgttaa gggattttgg      840
tcatgagatt atcaaaaagg atcttcacct agatccttt aaattaaaaa tgaagtttta      900
aatcaatcta agtatatat gagtaaactt ggtctgacag ttaccaatgc ttaatcagtg      960
aggcacctat ctcagcgatc tgtctatttc gttcatccat agttgcctga ctccccgtcg     1020
tgtagataac tacgatacgg gagggcttac catctggccc cagtgctgca atgataccgc     1080
gagacccacg ctcaccggct ccagatttat cagcaataaa ccagccagcc ggaagggccg     1140
agcgcagaag tggtcctgca actttatccg cctccatcca gtctattaat tgttgccggg     1200
aagctagagt aagtagttcg ccagttaata gtttgcgcaa cgttgttgcc attgctacag     1260
gcatcgtggt gtcacgctcg tcgtttggta tggcttcatt cagctccggt tcccaacgat     1320
caaggcgagt tacatgatcc cccatgttgt gcaaaaaagc ggttagctcc ttcggtcctc     1380
cgatcgttgt cagaagtaag ttggccgcag tgttatcact catggttatg gcagcactgc     1440
ataattctct tactgtcatg ccatccgtaa gatgcttttc tgtgactggt gagtactcaa     1500
ccaagtcatt ctgagaatag tgtatgcggc gaccgagttg ctcttgcccg gcgtcaatac     1560
gggataatac cgcgccacat agcagaactt taaaagtgct catcattgga aaacgttctt     1620
cggggcgaaa actctcaagg atcttaccgc tgttgagatc cagttcgatg taacccactc     1680
gtgcacccaa ctgatcttca gcatctttta ctttcaccag cgtttctggg tgagcaaaaa     1740
caggaaggca aaatgccgca aaaaagggaa taagggcgac acggaaatgt tgaatactca     1800
tactcttcct ttttcaattc agaagaactc gtcaagaagg cgatagaagg cgatgcgctg     1860
cgaatcggga gcggcgatac cgtaaagcac gaggaagcgg tcagcccatt cgccgccaag     1920
ctcttcagca atatcacggg tagccaacgc tatgtcctga tagcggtccg ccacacccag     1980
ccggccacag tcgatgaatc cagaaaagcg gccattttcc accatgatat tcggcaagca     2040
ggcatcgcca tgggtcacga cgagatcctc gccgtcgggc atgcgcgcct tgagcctggc     2100
gaacagttcg gctggcgcga gcccctgatg ctcttcgtcc agatcatcct gatcgacaag     2160
accggcttcc atccgagtac gtgctcgctc gatgcgatgt ttcgcttggt ggtcgaatgg     2220
gcaggtagcc ggatcaagcg tatgcagccg ccgcattgca tcagccatga tggatacttt     2280
ctcggcagga gcaaggtggg atgacaggag atcctgcccc ggcacttcgc ccaatagcag     2340
ccagtccctt cccgcttcag tgacaacgtc gagcacagct gcgcaaggaa cgcccgtcgt     2400
ggccagccac gatagccgcg ctgcctcgtc ctgcagttca ttcagggcac cggacaggtc     2460
ggtcttgaca aaaagaaccg ggcgcccctg cgctgacagc cggaacacgg cggcatcaga     2520
gcagccgatt gtctgttgtg cccagtcata gccgaatagc ctctccaccc aagcggccgg     2580
agaacctgcg tgcaatccat cttgttcaat catgcgaaac gatcctcatc ctgtctcttg     2640
atcagatctt gatcccctgc gccatcagat ccttggcggc aagaaagcca tccagtttac     2700
tttgcagggc ttcccaacct taccagaggg cgccccagct ggcaattccg gttcgcttgc     2760
tgtccataaa accgcccagt ctagctatcg ccatgtaagc ccactgcaag ctacctgctt     2820
tctctttgcg cttgcgtttt cccttgtcca gatagcccag tagctgacat tcatccgggg     2880
tcagcaccgt ttctgcggac tggctttcta cgtgttccgc ttcctttagc agcccttgcg     2940
ccctgaattt tgttaaaatt cgcgttaaat ttttgttaaa tcagctcatt ttttaaccaa     3000
taggccgaaa tcggcaaaat cccttataaa tcaaaagaat agaccgagat agggttgagt     3060
gttgttccag tttggaacaa gagtccacta ttaaagaacg tggactccaa cgtcaaaggg     3120
```

```
cgaaaaaccg tctatcaggg cgatggccca ctacgtgaac catcacccta atcaagtttt    3180
ttggggtcga ggtgccgtaa agcactaaat cggaaccccta aagggagccc ccgatttaga    3240
gcttgacggg gaaagccggc gaacgtggcg agaaaggaag ggaagaaagc gaaaggagcg    3300
ggcgctaggg cgctggcaag tgtagcggtc acgctgcgcg taaccaccac acccgccgcg    3360
cttaatgcgc cgctacaggg cgcgtccatt cgccattcag gctgcgcaac tgttgggaag    3420
ggcgatcggt gcgggcctct tcgctattac gccagctggc gaaaggggga tgtgctgcaa    3480
ggcgattaag ttgggtaacg ccagggtttt cccagtcacg acgttgtaaa acgacggcca    3540
gtgaattgta atacgactca ctatagggcg aattgggccc tctagatgca tgctcgagcg    3600
gccgccagtg tgatggatat ctgcagaatt cgccctttaa cagcatgagt gaacagaacc    3660
atctctatga tagtcctgaa tggctttttg gtctgaaaaa tatgcattgg ctctcattac    3720
atttaaccaa aattatcaca atataagaat gagatcttta acattgccaa ttaggtcagt    3780
ggtcccaagt agtcacttag aaaatctgtg tatgtgaaat actgttttgtg acttaaaatg    3840 aaatttattt ttaataggtg aacataatat tgaggagaca gaacatacag agcaaaagcg    3900
aaatgtgatt cgaattattc ctcaccacaa ctacaatgca gctattaata agtacaacca    3960
tgacattgcc cttctggaac tggacgaacc cttagtgcta aacagctacg ttacacctat    4020
ttgcattgct gacaaggaat acacgaacat cttcctcaaa tttggatctg gctatgtaag    4080
tggctgggga agagtcttcc acaaagggag atcagcttta gttcttcagt accttagagt    4140
tccacttgtt gaccgagcca catgtcttcg atctacaaag ttcaccatct ataacaacat    4200
gttctgtgct ggcttccatg aaggaggtag agattcatgt caaggagata gtggggacc     4260 ccatgttact gaagtggaag ggaccagttt cttaactgga attattagct ggggtgaaga    4320
gtgtgcaatg aaaggcaaat atggaatata taccaaggta tcccggtatg tcaactggat    4380
taaggaaaaa acaaagctca cttaatgaaa gatggatttc caaggttaat tcattggaat    4440
tgaaaattaa cagggcctct cactaactaa tcactttccc atctttttgt agatttgaat    4500
atatacattc tatgatcatt gctttttctc tttacagggg agaatttcat attttacctg    4560
agcaaattga ttagaaaatg gaaccactag aggaatataa tgtgttagga aattacagtc    4620
atttctaagg gcccagaagg gcgaattcca gcacactggc ggccgttact agtggatccg    4680
agctcggtac caagcttggc gtaatcatgg tcatagctgt ttcctgtgtg aaattgttat    4740
ccgctcacaa ttccacacaa catacgagcc ggaagcataa agtgtaaagc ctggggtgcc    4800
taatgagtga gctaactcac attaattgcg ttgcgctcac tgcccgcttt ccagtcggga    4860
aacctgtcgt gccagctgca ttaatgaatc ggccaacgcg cggggagagg cggtttgcgt    4920
attgggcgct                                                          4930

<210> SEQ ID NO 38
<211> LENGTH: 6996
<212> TYPE: DNA
<213> ORGANISM: Artificial Sequence
<220> FEATURE:
<223> OTHER INFORMATION: Plasmid pDuoF9-ex8 (outcome)
<220> FEATURE:
<221> NAME/KEY: P3 binding site
<222> LOCATION: (1373)..(1392)
<220> FEATURE:
<221> NAME/KEY: Recombinase R1 (placeholder)
<222> LOCATION: (1519)..(2550)
<220> FEATURE:
<221> NAME/KEY: Recombinase R#7-B5 (placeholder)
<222> LOCATION: (1519)..(2550)
<220> FEATURE:
```

```
<221> NAME/KEY: Ribosome binding site
<222> LOCATION: (2551)..(2633)
<220> FEATURE:
<221> NAME/KEY: LoxF9a
<222> LOCATION: (4220)..(4253)
<220> FEATURE:
<221> NAME/KEY: exchanged part of human F9 gene including exon 8
<222> LOCATION: (4220)..(4253)
<220> FEATURE:
<221> NAME/KEY: LoxF9b
<222> LOCATION: (4962)..(5019)
<220> FEATURE:
<221> NAME/KEY: P4 binding site
<222> LOCATION: (4962)..(4981)
<220> FEATURE:
<221> NAME/KEY: CmR
<222> LOCATION: (5127)..(5786)
<220> FEATURE:
<221> NAME/KEY: Origin of replication
<222> LOCATION: (6148)..(6996)

<400> SEQUENCE: 38
```

| | | |
|---|---|---|
| gctcatgagc cgaagtggc gagcccgatc ttccccatcg gtgatgtcgg cgatataggc | 60 |
| gccagcaacc gcacctgtgg cgccggtgat gccggccacg atgcgtccgg cgtagaggat | 120 |
| ctgctcatgt ttgacagctt atcatcgatg cataatgtgc ctgtcaaatg gacgaagcag | 180 |
| ggattctgca aaccctatgc tactccgtca agccgtcaat tgtctgattc gttaccaatt | 240 |
| atgacaactt gacggctaca tcattcactt tttcttcaca accggcacgg aactcgctcg | 300 |
| ggctggcccc ggtgcatttt ttaaatacc gcgagaaata gagttgatcg tcaaaaccaa | 360 |
| cattgcgacc gacggtggcg ataggcatcc gggtggtgct caaaagcagc ttcgcctggc | 420 |
| tgatacgttg gtcctcgcgc cagcttaaga cgctaatccc taactgctgg cggaaaagat | 480 |
| gtgacagacg cgacggcgac aagcaaacat gctgtgcgac gctggcgata tcaaaattgc | 540 |
| tgtctgccag gtgatcgctg atgtactgac aagcctcgcg tacccgatta ccatcggtg | 600 |
| gatggagcga ctcgttaatc gcttccatgc gccgcagtaa caattgctca agcagattta | 660 |
| tcgccagcag ctccgaatag cgcccttccc cttgcccggc gttaatgatt tgcccaaaca | 720 |
| ggtcgctgaa atgcggctgg tgcgcttcat ccgggcgaaa gaaccccgta ttggcaaata | 780 |
| ttgacggcca gttaagccat tcatgccagt aggcgcgcgg acgaaagtaa acccactggt | 840 |
| gataccattc gcgagcctcc ggatgacgac cgtagtgatg aatctctcct ggcgggaaca | 900 |
| gcaaaatatc acccggtcgg caaacaaatt ctcgtccctg attttcacc cccctgac | 960 |
| cgcgaatggt gagattgaga atataacctt tcattcccag cggtcggtcg ataaaaaaat | 1020 |
| cgagataacc gttggcctca atcggcgtta aacccgccac cagatgggca ttaaacgagt | 1080 |
| atcccggcag caggggatca ttttgcgctt cagccatact tttcatactc ccgccattca | 1140 |
| gagaagaaac caattgtcca tattgcatca gacattgccg tcactgcgtc ttttactggc | 1200 |
| tcttctcgct aaccaaaccg gtaacccgc ttattaaaag cattctgtaa caaagcggga | 1260 |
| ccaaagccat gacaaaaacg cgtaacaaaa gtgtctataa tcacggcaga aaagtccaca | 1320 |
| ttgattattt gcacggcgtc acactttgct atgccatagc atttttatcc ataagattag | 1380 |
| cggatcctac ctgacgcttt ttatcgcaac tctctactgt ttctccatac ccgttttttt | 1440 |
| gggctagcga attcgagctc taaggaggtg ccacaattct cgagccatac ccattctaat | 1500 |
| gatcataagg aggtgtacat gtcaatacta ctgaccttgc accaaagttt gtccgcatta | 1560 |
| ctggtcgatg caacgagtga tgaggctcgc aagaacctga tggatgtgct cagggatcgc | 1620 |
| caggcgttct ccgagcgtac ctggaaagtg ctcctgtccg tttgccggac gtgggcggca | 1680 |

-continued

```
tggtgcaagt tgaacaaccg gaaatggttt cccgcggaac ctgaagatgt tcgcgattac    1740
cttctacatc ttcaggctcg cggtctggca gtaaacacta tcctgcaaca tttggcccag    1800
ctaaacatgc tccaccgtcg gttcgggctg ccacgaccgg gcgacagcga cgctgtttca    1860
ctggttatgc ggcgaatccg aagggagaac gtcgatgctg gtgagcgtac caagcaggcc    1920
ctagcgttcg agcgcactga cttcgaccag gttcgtgcac tcatggaaaa tagcgaacgg    1980
ggccaggata tacgtactct ggcacttctg ggggttgctt ataacaccct gttacgcgta    2040
tccgaaattg ccaggattcg gattaaagac atctcacgta ctgacggtgg gaggatgcta    2100
atccacatta gcagaacgaa aacgctggtc agcaccgcag gcgtagagaa ggcgcttagc    2160
ctgggggtaa ctaaactggt cgagcgatgg atttccgtct ctggtgtggc tagtgaccca    2220
aacaattacc tgttttgcca ggttagaata aatggtgtgg ccgtgccgtc tgccaccagc    2280
cggctatcaa ccgacgtcct gcgaaagatt tttgaggctg cccaccgcct gatctacggt    2340
gccaaggatg ctctggtca  gagatacctg gcctggtctg gcacagtgc  ccgtgtcgga    2400
gccgcgcggg atatggcccg cgctgggggtt tcaatagcgg agattatgca ggctggtggc    2460
tggaccaccg tagagagtgt catgaactat atccgtaacc tggacagtga cacaggggca    2520
atggtgcgtc tgctggaaga tggcgactag tctagaggta ccattccgat cgcggatcgg    2580
ccggaatggg atagacgtcc tatcatccac acctactagt taaggaggtg tacatgtcaa    2640
tactactgac cttgcaccaa agtttgtccg cattactggt cgatgcaacg agtgatgagg    2700
ctcgcaagaa cctgatggat gtgctcaggg atcgccaggc gttctccgag cgtacctgga    2760
aagtgctcct gtccgtttgc cggacgtggg cggcatggtg caagttgaac aaccggaaat    2820
ggtttcccgc ggaacctgaa gatgttcgcg attaccttct acatcttcag gctcgcggtc    2880
tggcagtaaa cactatcctg caacatttgg cccagctaaa catgctccac cgtcggttcg    2940
ggctgccacg accgggcgac agcgacgctg tttcactggt tatgcggcga atccgaaggg    3000
agaacgtcga tgctggtgag cgtaccaagc aggcccctagc gttcgagcgc actgacttcg    3060
accaggttcg tgcactcatg gaaaatagcg aacggggcca ggatatacgt actctggcac    3120
ttctgggggt tgcttataac accctgttac gcgtatccga aattgccagg attcggatta    3180
aagacatctc acgtactgac ggtgggagga tgctaatcca cattagcaga acgaaaacgc    3240
tggtcagcac cgcaggcgta gagaaggcgc ttagcctggg ggtaactaaa ctggtcgagc    3300
gatggatttc cgtctctggt gtggctagtg acccaaacaa ttacctgttt tgccaggtta    3360
gaataaatgg tgtggccgtg ccgtctgcca ccagccggct atcaaccgac gtcctgcgaa    3420
agatttttga ggctgcccac cgcctgatct acggtgccaa ggatggctct ggtcagagat    3480
acctggcctg gtctgggcac agtgcccgtg tcggagccgc gcgggatatg gcccgcgctg    3540
ggggtttcaat agcggagatt atgcaggctg gtggctggac caccgtagag agtgtcatga    3600
actatatccg taacctggac agtgagacag gggcaatggt gcgtctgctg aagatggcg     3660
actagtctag acgtacgcct gcaggcaagc ttggctgttt tggcggatga gaagagattt    3720
tcagcctgat acagattaaa tcagaacgca gaagcggtct gataaaacag aatttgcctg    3780
gcggcagtag cgcggtggtc ccacctgacc ccatgccgaa ctcagaagtg aaacgccgta    3840
gcgccgatgg tagtgtgggg tctccccatg cgagagtagg gaactgccag gcatcaaata    3900
aaacgaaagg ctcagtcgaa agactggggc tttcgtttta tctgttgttt gtcggtgaac    3960
gctctcctga gtaggacaaa tccgccggga gcggatttga acgttgcgaa gcaacggccc    4020
ggagggtggc gggcaggacg cccgccataa actgccaggc atcaaattaa gcagaaggcc    4080
```

```
atcctgacgg atggcctttt tgcgtttcta caaactcttt tgtttatttt tctaaataca    4140
ttcaaatatg tatccgctca tgagacaata accctgataa atgcttcaat aatattgaaa    4200
aaggaagagt atgagatctc tcattacatt taaccaaaat tatcacaata taagaatgag    4260
atctttaaca ttgccaatta ggtcagtggt cccaagtagt cacttagaaa atctgtgtat    4320
gtgaaatact gtttgtgact taaaatgaaa tttatttta ataggtgaac ataatattga     4380
ggagacagaa catacagagc aaaagcgaaa tgtgattcga attattcctc accacaacta    4440
caatgcagct attaataagt acaaccatga cattgccctt ctggaactgg acgaaccctt    4500
agtgctaaac agctacgtta cacctatttg cattgctgac aaggaataca cgaacatctt    4560
cctcaaattt ggatctggct atgtaagtgg ctggggaaga gtcttccaca aagggagatc    4620
agctttagtt cttcagtacc ttagagttcc acttgttgac cgagccacat gtcttcgatc    4680
tacaaagttc accatctata acaacatgtt ctgtgctggc ttccatgaag gaggtagaga    4740
ttcatgtcaa ggagatagtg ggggaccccca tgttactgaa gtggaaggga ccagtttctt    4800
aactggaatt attagctggg gtgaagagtg tgcaatgaaa ggcaaatatg gaatatatac    4860
caaggtatcc cggtatgtca actggattaa ggaaaaaaca aagctcactt aatgaaaagat    4920 ggatttccaa ggttaattca ttggaattga aaattaacag ggcctctcac taactaatca    4980
ctttcccatc ttttgttaga tttgaatata tacattctaa gatctggtcg aatttgcttt    5040
cgaatttctg ccattcatcc gcttattatc acttattcag gcgtagcacc aggcgtttaa    5100
gggcaccaat aactgcctta aaaaaattac gccccgccct gccactcatc gcagtactgt    5160
tgtaattcat taagcattct gccgacatgg aagccatcac agacggcatg atgaacctga    5220
atcgccagcg gcatcagcac cttgtcgcct tgcgtataat atttgcccat ggtgaaaacg    5280
ggggcgaaga agttgtccat attggccacg tttaaatcaa aactggtgaa actcacccag    5340
ggattggctg agacgaaaaa catattctca ataaaccctt tagggaaata ggccaggttt    5400
tcaccgtaac acgccacatc ttgcgaatat atgtgtagaa actgccggaa atcgtcgtgg    5460
tattcactcc agagcgatga aaacgtttca gtttgctcat ggaaaacggt gtaacaaggg    5520
tgaacactat cccatatcac cagctcaccg tctttcattg ccatacgaa ttccggatga     5580 gcattcatca ggcgggcaag aatgtgaata aaggccggat aaaacttgtg cttatttttc    5640
tttacggtct ttaaaaaggc cgtaatatcc agctgaacgg tctggttata ggtacattga    5700
gcaactgact gaaatgcctc aaaatgttct ttacgatgcc attgggatat atcaacggtg    5760
gtatatccag tgatttttt ctccatttta gcttccttag ctcctgaaaa tctcgataac     5820
tcaaaaaata cgcccggtag tgatcttatt tcattatggt gaagttggaa acctcttacg    5880
tgccgatcaa cgtctcattt tcgccaaaag ttggcccagg gcttcccggt atcaacaggg    5940
acaccaggat ttatttattc tgcgaagtga tcttccgtca caggtattta ttcggcgcaa    6000
agtgcgtcgg gtgatgctgc caacttactg atttagtgta tgatggtgtt tttgaggtgc    6060
tccagtggct tctgtttcta tcagctgtcc ctcctgttca gctactgacg ggtggtgcg    6120 taacggcaaa agcaccgccg gacatcagcg ctagcggagt gtatactggc ttactatgtt    6180
ggcactgatg agggtgtcag tgaagtgctt catgtggcag agaaaaaag gctgcaccgg     6240 tgcgtcagca gaatatgtga tacaggatat attccgcttc ctcgctcact gactcgctac    6300
gctcggtcgt tcgactgcgg cgagcggaaa tggcttacga acgggcggga gatttcctgg    6360
aagatgccag gaagatactt aacagggaag tgagagggcc gcggcaaagc cgttttttcca    6420
```

-continued

```
taggctccgc cccctgaca agcatcacga aatctgacgc tcaaatcagt ggtggcgaaa     6480
cccgacagga ctataaagat accaggcgtt tccccctggc ggctccctcg tgcgctctcc     6540
tgttcctgcc tttcggttta ccggtgtcat tccgctgtta tggccgcgtt tgtctcattc     6600
cacgcctgac actcagttcc gggtaggcag ttcgctccaa gctggactgt atgcacgaac     6660 ccccgttca gtccgaccgc tgcgcctat ccggtaacta tcgtcttgag tccaacccgg      6720
aaagacatgc aaaagcacca ctggcagcag ccactggtaa ttgatttaga ggagttagtc    6780
ttgaagtcat gcgccggtta aggctaaact gaaaggacaa gttttggtga ctgcgctcct    6840
ccaagccagt tacctcggtt caaagagttg gtagctcaga gaaccttcga aaaccgccc    6900 tgcaaggcgg ttttttcgtt ttcagagcaa gagattacgc gcagaccaaa acgatctcaa    6960
gaagatcatc ttattaatca gataaaatat ttctag                             6996
```

<210> SEQ ID NO 39
<211> LENGTH: 343
<212> TYPE: PRT
<213> ORGANISM: Bacteriophage P1

<400> SEQUENCE: 39

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270
```

```
Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

```
<210> SEQ ID NO 40
<211> LENGTH: 34
<212> TYPE: DNA
<213> ORGANISM: Homo sapiens

<400> SEQUENCE: 40
tacacagtgt atattgattt ttatcaaatg cctt                               34

<210> SEQ ID NO 41
<211> LENGTH: 34
<212> TYPE: DNA
<213> ORGANISM: Homo sapiens

<400> SEQUENCE: 41
tacacaatgt atattgattt ttatcaaatg cctt                               34

<210> SEQ ID NO 42
<211> LENGTH: 34
<212> TYPE: DNA
<213> ORGANISM: Artificial Sequence
<220> FEATURE:
<223> OTHER INFORMATION: Intermediate target site HexL

<400> SEQUENCE: 42
tacacagtgt atattgattt ttatacattg tgta                               34

<210> SEQ ID NO 43
<211> LENGTH: 34
<212> TYPE: DNA
<213> ORGANISM: Artificial Sequence
<220> FEATURE:
<223> OTHER INFORMATION: Intermediate target site HexR

<400> SEQUENCE: 43
aaggcatttg atattgattt ttatcaaatg cctt                               34

<210> SEQ ID NO 44
<211> LENGTH: 34
<212> TYPE: DNA
<213> ORGANISM: Artificial Sequence
<220> FEATURE:
<223> OTHER INFORMATION: Intermediate target site HexR1

<400> SEQUENCE: 44
aagacatttt atattgattt ttataaaatg tctt                               34

<210> SEQ ID NO 45
<211> LENGTH: 34
<212> TYPE: DNA
<213> ORGANISM: Artificial Sequence
<220> FEATURE:
<223> OTHER INFORMATION: Intermediate target site HexR2
```

```
<400> SEQUENCE: 45
aacgcattgg atattgattt ttatccaatg cgtt                              34

<210> SEQ ID NO 46
<211> LENGTH: 343
<212> TYPE: PRT
<213> ORGANISM: Artificial Sequence
<220> FEATURE:
<223> OTHER INFORMATION: Recombinase Hex-R-#7

<400> SEQUENCE: 46
```

| Met | Ser | Asn | Leu | Gln | Thr | Leu | His | Gln | Asn | Leu | Ser | Ala | Leu | Leu | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Ala | Thr | Ser | Asp | Glu | Ala | Arg | Lys | Asn | Leu | Thr | Asp | Val | Leu | Arg |
|     |     |     | 20  |     |     |     |     | 25  |     |     |     |     | 30  |     |     |

| Asp | Ser | Gln | Ala | Phe | Ser | Glu | His | Thr | Trp | Arg | Val | Leu | Leu | Ser | Val |
|     |     |     | 35  |     |     |     |     | 40  |     |     |     |     | 45  |     |     |

| Cys | Arg | Ser | Trp | Ala | Ala | Trp | Cys | Glu | Leu | Asn | Asn | Arg | Lys | Trp | Phe |
|     | 50  |     |     |     |     | 55  |     |     |     |     | 60  |     |     |     |     |

| Pro | Ala | Glu | Pro | Glu | Asp | Val | Arg | Asp | Tyr | Leu | Leu | His | Leu | Gln | Ala |
| 65  |     |     |     |     | 70  |     |     |     |     | 75  |     |     |     |     | 80  |

| Arg | Gly | Leu | Thr | Val | Asn | Thr | Ile | Gln | Gln | His | Leu | Cys | Gln | Leu | Asn |
|     |     |     |     | 85  |     |     |     |     | 90  |     |     |     |     | 95  |     |

| Met | Leu | His | Arg | Arg | Ser | Gly | Leu | Pro | Pro | Pro | Gly | Asp | Ser | Asn | Ala |
|     |     |     |     | 100 |     |     |     |     | 105 |     |     |     |     | 110 |     |

| Ala | Ser | Leu | Val | Met | Arg | Arg | Ile | Arg | Lys | Glu | Asn | Val | Asp | Ala | Gly |
|     |     |     | 115 |     |     |     |     | 120 |     |     |     |     | 125 |     |     |

| Glu | Arg | Val | Lys | Gln | Ala | Leu | Ala | Phe | Glu | Arg | Thr | Asp | Leu | Asp | Gln |
|     | 130 |     |     |     |     | 135 |     |     |     |     | 140 |     |     |     |     |

| Val | Cys | Ala | Leu | Met | Glu | Asn | Ser | Asn | Arg | Cys | Gln | Asp | Ile | Arg | Asn |
| 145 |     |     |     |     | 150 |     |     |     |     | 155 |     |     |     |     | 160 |

| Leu | Ala | Phe | Leu | Gly | Val | Ala | Tyr | Asn | Thr | Leu | Leu | Arg | Ile | Ser | Glu |
|     |     |     |     | 165 |     |     |     |     | 170 |     |     |     |     | 175 |     |

| Val | Ala | Arg | Ile | Arg | Val | Arg | Asp | Ile | Thr | Arg | Thr | Asp | Gly | Gly | Arg |
|     |     |     | 180 |     |     |     |     | 185 |     |     |     |     | 190 |     |     |

| Met | Leu | Ile | His | Ile | Gly | Arg | Thr | Lys | Thr | Leu | Val | Ser | Thr | Ala | Gly |
|     |     |     | 195 |     |     |     |     | 200 |     |     |     |     | 205 |     |     |

| Val | Glu | Lys | Ala | Leu | Ser | Leu | Arg | Val | Thr | Lys | Leu | Val | Glu | Arg | Trp |
|     | 210 |     |     |     |     | 215 |     |     |     |     | 220 |     |     |     |     |

| Ile | Ser | Val | Ser | Gly | Val | Ala | Asp | Asp | Pro | Asn | Asn | Phe | Leu | Phe | Cys |
| 225 |     |     |     |     | 230 |     |     |     |     | 235 |     |     |     |     | 240 |

| Arg | Val | Gly | Arg | Asn | Gly | Val | Ala | Val | Ser | Ser | Ala | Thr | Ser | Gln | Leu |
|     |     |     |     | 245 |     |     |     |     | 250 |     |     |     |     | 255 |     |

| Ser | Thr | Pro | Ala | Leu | Gln | Gly | Ile | Phe | Ala | Ser | Ala | His | Arg | Leu | Ile |
|     |     |     | 260 |     |     |     |     | 265 |     |     |     |     | 270 |     |     |

| Tyr | Gly | Ala | Arg | Asp | Asp | Pro | Gly | Gln | Arg | Tyr | Leu | Thr | Trp | Ser | Gly |
|     |     |     | 275 |     |     |     |     | 280 |     |     |     |     | 285 |     |     |

| His | Ser | Ala | Arg | Val | Gly | Ala | Ala | Arg | Asp | Met | Ala | Arg | Ala | Gly | Val |
|     | 290 |     |     |     |     | 295 |     |     |     |     | 300 |     |     |     |     |

| Pro | Ile | Ala | Glu | Ile | Met | Gln | Ala | Gly | Gly | Trp | Thr | Thr | Ile | Glu | Ser |
| 305 |     |     |     |     | 310 |     |     |     |     | 315 |     |     |     |     | 320 |

| Val | Met | Asn | Tyr | Leu | Arg | Asn | Leu | Asp | Ser | Glu | Thr | Gly | Ala | Met | Val |
|     |     |     |     | 325 |     |     |     |     | 330 |     |     |     |     | 335 |     |

| Arg | Leu | Leu | Glu | Gly | Asp | Asp |
|     |     |     | 340 |     |     |     |

```
<210> SEQ ID NO 47
<211> LENGTH: 343
<212> TYPE: PRT
<213> ORGANISM: Artificial Sequence
<220> FEATURE:
<223> OTHER INFORMATION: Recombinase Hex-L-#7

<400> SEQUENCE: 47
```

Met Ser Asn Leu Gln Thr Leu His Gln Asn Leu Ser Ala Leu Leu Val
1               5                   10                  15

Asp Val Thr Ser Asp Glu Ala Arg Lys Ser Leu Met Asp Met Leu Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Glu Ser Asn Asn Arg Lys Trp Phe
50                  55                  60

Pro Ala Glu Pro Glu Asp Val Arg Asp Tyr Leu Leu His Leu Gln Ala
65                  70                  75                  80

Arg Gly Leu Ala Val Arg Thr Ile Gln Gln His Leu Cys Gln Leu Asn
                85                  90                  95

Met Leu His Arg Arg Ser Gly Leu Pro Arg Pro Gly Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
130                 135                 140

Val Arg Ser Leu Met Glu Asp Ser Asp Arg Cys Gln Asp Ile Arg Asn
145                 150                 155                 160

Leu Ala Phe Leu Gly Ile Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Gly Arg Thr Lys Thr Leu Ile Ser Thr Ala Gly
        195                 200                 205

Val Glu Lys Ala Leu Ser Leu Gly Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Arg Val Arg Lys His Gly Val Ala Ala Pro Ser Ala Thr Ser Gln Leu
                245                 250                 255

Ser Thr Asn Ala Leu Gln Arg Ile Phe Glu Ala Ala His Cys Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
290                 295                 300

Ser Ile Pro Glu Ile Met Gln Ala Gly Gly Trp Thr Thr Val Asn Ser
305                 310                 315                 320

Val Met Asn Tyr Ile Arg Asn Leu Asp Ser Glu Thr Gly Ala Met Val
                325                 330                 335

Arg Leu Leu Glu Glu Gly Asp
            340

```
<210> SEQ ID NO 48
```

<211> LENGTH: 343
<212> TYPE: PRT
<213> ORGANISM: Artificial Sequence
<220> FEATURE:
<223> OTHER INFORMATION: Recombinase Hex-R-#30

<400> SEQUENCE: 48

Met Ser Tyr Leu His Thr Leu His Gln Ser Leu Ser Ala Leu Leu Val
1               5                   10                  15
Asn Ala Thr Ser Asp Glu Ala Arg Lys Asn Leu Met Asp Val Phe Arg
            20                  25                  30
Asp Cys Gln Ala Phe Ser Glu His Thr Trp Arg Val Leu Leu Ser Val
        35                  40                  45
Cys Arg Ser Trp Val Thr Trp Cys Lys Leu Asn Asn Arg Lys Trp Phe
    50                  55                  60
Pro Ala Glu Pro Glu Asp Val Arg Asp Tyr Leu Leu His Leu Gln Ala
65                  70                  75                  80
Arg Gly Leu Thr Val Asn Thr Ile Gln Gln His Leu Cys Gln Leu Asn
                85                  90                  95
Met Leu His Arg Arg Ser Gly Leu Pro Arg Pro Gly Asp Ser Asn Ala
            100                 105                 110
Val Thr Leu Val Met Arg Arg Ile Arg Lys Glu Asn Val Asp Ala Gly
        115                 120                 125
Glu Arg Thr Lys Gln Ala Leu Ala Phe Glu Arg Thr Asp Phe Gly Gln
    130                 135                 140
Val Arg Ser Leu Met Glu Asn Ser Asp Arg Cys Arg Asp Ile Arg Asn
145                 150                 155                 160
Leu Ala Phe Leu Gly Val Ala Tyr Asn Thr Leu Leu Arg Ile Ser Glu
                165                 170                 175
Ile Ala Arg Ile Arg Val Arg Asp Ile Ser Arg Thr Asp Gly Gly Arg
            180                 185                 190
Met Leu Ile His Ile Gly Arg Thr Lys Thr Leu Val Ser Thr Ala Gly
        195                 200                 205
Ala Glu Lys Ala Leu Ser Gln Gly Val Thr Lys Leu Val Glu Arg Trp
    210                 215                 220
Ile Ser Val Ser Gly Val Ala Asp Asp Pro Asn Asn Tyr Leu Phe Cys
225                 230                 235                 240
Arg Val Arg Arg Asn Gly Val Ala Ala Pro Ser Ala Thr Gly Gln Leu
                245                 250                 255
Ser Thr Pro Ala Leu Gln Gly Ile Phe Val Ser Ala His Arg Leu Val
            260                 265                 270
Tyr Gly Ala Arg Asp Ala Ser Gly Gln Arg Tyr Leu Thr Trp Ser Gly
        275                 280                 285
His Ser Ala Arg Val Gly Thr Ala Arg Asp Met Ala Arg Ala Gly Val
    290                 295                 300
Pro Ile Ala Glu Ile Met Gln Ala Gly Gly Trp Thr Thr Ile Glu Ser
305                 310                 315                 320
Val Met Asn Tyr Leu Arg Asn Leu Asp Ser Glu Thr Gly Ala Met Val
                325                 330                 335
Arg Leu Leu Glu Asp Asp Asp
            340

<210> SEQ ID NO 49
<211> LENGTH: 343
<212> TYPE: PRT
<213> ORGANISM: Artificial Sequence

```
<220> FEATURE:
<223> OTHER INFORMATION: Recombinase Hex-L-#30

<400> SEQUENCE: 49

Met Ser Asn Leu Gln Thr Leu His Gln Asn Leu Ser Ala Leu Leu Val
1               5                   10                  15

Asp Ala Thr Cys Asp Glu Ala Arg Glu Asn Leu Leu Asn Met Phe Arg
            20                  25                  30

Asp Arg Gln Ala Phe Ser Glu His Thr Trp Lys Met Leu Leu Ser Val
            35                  40                  45

Cys Arg Ser Trp Ala Ala Trp Cys Glu Leu Asn Asn Arg Lys Trp Phe
            50                  55                  60

Pro Ala Glu Pro Glu Asp Val Arg Asp Tyr Leu Leu His Leu Gln Ala
65                  70                  75                  80

Arg Gly Leu Ala Val Lys Thr Ile Gln Gln His Leu Ala Gln Leu Asn
                85                  90                  95

Met Leu His Arg Arg Ser Gly Leu Pro Arg Pro Gly Asp Ser Asn Ala
                100                 105                 110

Val Ser Leu Val Val Arg Arg Ile Arg Lys Glu Asn Val Asp Ala Gly
            115                 120                 125

Glu Arg Ala Lys Gln Ala Leu Ala Phe Glu Arg Thr Asp Phe Asp Gln
            130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ser Glu
                165                 170                 175

Ile Ala Arg Ile Arg Val Lys Asp Ile Ser Arg Thr Asp Gly Gly Arg
                180                 185                 190

Met Leu Ile His Ile Gly Arg Thr Lys Thr Leu Val Ser Thr Ala Gly
                195                 200                 205

Val Glu Lys Ala Leu Ser Leu Gly Val Thr Lys Leu Val Glu Arg Trp
            210                 215                 220

Ile Ser Val Ser Gly Val Ala Asp Asp Pro Asn Asn Tyr Leu Phe Cys
225                 230                 235                 240

Arg Val Ser Lys Tyr Gly Val Ala Ala Pro Ser Ala Thr Ser Gln Leu
                245                 250                 255

Ser Thr His Ala Leu Gln Arg Ile Phe Glu Ala Ala His Arg Leu Ile
                260                 265                 270

Tyr Gly Ala Lys Asp Asp Ser Gly Arg Arg Tyr Leu Ala Trp Ser Gly
            275                 280                 285

His Ser Ala Arg Val Gly Ala Ala Arg Asp Met Ala Arg Ala Gly Val
            290                 295                 300

Ser Ile Pro Glu Ile Met Gln Ala Gly Gly Trp Ala Thr Val Asn Ser
305                 310                 315                 320

Val Met Asn Tyr Ser Arg Asn Leu Asp Ser Glu Ala Gly Ala Met Val
                325                 330                 335

Arg Leu Leu Glu Asp Gly Asp
                340
```

METHODS AND MEANS FOR GENETIC ALTERATION OF GENOMES UTILIZING DESIGNER DNA RECOMBINING ENZYMES

SEQUENCE LISTING

The instant application contains a Sequence Listing which has been submitted in ASCII format via EFS-Web and is hereby incorporated by reference in its entirety. Said ASCII copy, created on Dec. 15, 2019, is named 96158_302_2_ST25.txt and is Size: 111,443 bytes in size.

CROSS-REFERENCE TO RELATED APPLICATIONS

This is the U.S. National Stage of International Patent Application No. PCT/EP2018/065881 filed on Jun. 14, 2018, which was published in English under PCT Article 21(2), which in turn claims priority to European Patent Application No. 17175895.6 filed on Jun. 14, 2017.

The invention provides methods and means for specifically altering the DNA sequence in a genome. Provided are vectors and methods to generate designer DNA recombining enzymes. The invention is useful for medicine, in particular to repair a mutation in a genome or to delete predefined genetic material from cells or tissue and to cure diseases. Further, the invention is useful for biological and biomedical research (e. g. to create animal models).

Many genetic mutations that cause human diseases have been identified over the last decades. Recent breakthroughs in the field of genome editing now provide a genuine opportunity to establish innovative approaches to repair DNA lesions to replace, engineer or regenerate malfunctioning cells in vitro, or in the body.

However, most of the recently developed genome editing technologies such as zinc finger nucleases (e. g. US20150093802 A1), TALENs (e. g. WO2014134412 A1) and CRISPR/Cas9 (e. g. U.S. Pat. No. 8,697,359 B1) introduce double stranded DNA breaks at a target locus as the first step to gene correction. These breaks are subsequently repaired by one of the cell intrinsic DNA repair mechanisms, typically inducing an abundance of random insertions and deletions (indels) at the target locus. Ideally, therapeutic genome editing should, however, be efficient and specific, without the introduction of indels.

DNA recombining enzymes, in particular site-specific recombinase (SSR) systems, allow precise manipulation of DNA without triggering endogenous DNA repair pathways and possess the unique ability to fulfill both cleavage and immediate resealing of the processed DNA in vivo. Furthermore, SSR systems, such as Cre/loxP (EP 0 2200 009 B1) have found widespread use in model organisms, demonstrating that they can be safe, even when expressed lifelong in animals. SSRs work as tetramers on their target sites and depending on the orientation of these sites, recombination can lead to a variety of outcomes. It is known that the amino acid sequence of Cre can be modified in order to obtain novel site-specific recombinases (Buchholz F and Stewart A F 2001).

Other SSR systems know in the art include the Flp/FRT system (WO 1999025841 A1 and U.S. Pat. No. 6,774,279 B2), the Dre/rox system (U.S. Pat. No. 7,422,889 B2 and U.S. Pat. No. 7,915,037 B2), the VCre/VloxP system and the sCre/SloxP system (WO 2010/143606 A1), as well as the Vika/vox, the Nigri/nox and the Panto/pox systems (WO 2014/016248 A1).

Naturally occurring DNA recombining enzymes, in particular site-specific recombinase (SSR) systems (such tyrosine-type SSRs), generally consist of four identical monomers. In general they recognize two identical and symmetric, palindromic target sites, which consist each of two 13 nucleotide long half sites separated by an asymmetric frequently 8 nucleotide long spacer. Depending on the number and relative orientation of the target sites the DNA recombining enzyme either causes a deletion, an insertion, an inversion or a replacement of genetic content.

A bottleneck for using DNA recombining enzymes in therapeutic genome editing has been the limited number of sequences they can recombine.

In WO2008083931A1 this limitation was addressed to some extend by the directed molecular evolution of tailored recombinases (Tre 1.0) that uses sequences in the long terminal repeat (LTR) of HIV as recognition sites (loxLTR Tre 1.0). Further developments of this approach using asymmetric target sites were described in WO2011147590 A2 (Tre 3.0) and WO2016034553 A1 (Tre 3.1 and uTre/Brec1) as well as the publication Karpinski J et al 2016 (Brec1). However, in all cases this approach has limited utility, because the exact recognition site with a length of 34 base pairs has to be present twice in the genome (such as in the LTR of an integrated HI provirus) for the system to work.

WO2009007982A1 describes nucleic acid sequences located in the LTR of HIV-1 as potential target sites for DNA recombining enzymes.

US2009/0217400 A1 describes an enzyme and a method for recombination at asymmetric loxP-M7 target sites. Further, Zhang, C et al. (2015) and US 20170058297 A1 describe an obligate heterotetramer complex of two Cre mutants that recognize asymmetric loxP-M7 target sites. However, these recognition sites have to be introduced artificially into the genome.

US 20040003435 A1 describes a method for targeted insertion of a sequence of interest into a plant said method comprising introducing a transfer cassette comprising said nucleotide sequence of interest flanked by or comprising non-identical recognition sites, which are modified FRT sites that can still be recognized by the wild-type FLP recombinase.

Taken together the application of the recombinase systems known in the state of the art is limited by either the fact that two recognition sites have to be introduced artificially into the genome or that the sequence of interest in the genome has to be flanked by two identical sequences with a length of 34 base pairs.

Therefore, currently straightforward genome editing approaches rely on programmable nucleases, such as RNA-guided nucleases like CRISPR/Cas9 (e. g. U.S. Pat. No. 8,657,359 B1) as the specificity of these enzymes for a target site is defined by the guide RNA, which can be versatility adapted to a sequence of interest.

However, as the nucleases systems need the cell intrinsic DNA repair mechanisms they typically induce an abundance of random insertions and deletions (indels) at the target locus.

The ideal genome editing or gene therapy will replace the defective gene with a normal allele or delete a defective gene at its natural location without further modification of the genome. Thus, the ideal genome editing should be efficient and specific, without the introduction of indels.

An objective of the invention is therefore to provide a method to alter a nucleotide sequence in a genome that overcomes the disadvantages of the nuclease genome editing approaches and which is at the same time versatile adaptable to a sequence of interest.

The invention is based on the finding that two identical sequences with a length of 34 base pairs (the length of a usual target site of a DNA recombining enzyme) are rarely found in a genome.

The invention starts with the realization of the inventors that the only restriction to achieve excision recombination for Designer DNA-recombining enzymes is the conservation of the spacer sequence, normally 8 bp long (see FIG. 17 for an example). Because this sequence has to be identical for recombination to occur, it sets a constraint for sequences that can be recombined. However, a bioinformatics analysis of different genomes revealed that direct repeats of 8 bp length are frequently occurring in viral, prokaryotic and eukaryotic genomes, including the human genome (see FIG. 18, 19 for an example).).

Based on this finding the inventors realized that through a combination of different monomers of DNA-recombining enzymes evolved to target different target sites in the genome, precise genome editing becomes possible without engaging cellular repair pathways. Thus, a combination of monomers of DNA-recombining enzymes generated via directed evolution, rational design, or a combination thereof can be generated to virtually recombine any sequence of interest in a genome. In case the recombination shall result in a deletion of a sequence two identical sequences with a length of approximately 8 base pairs are needed as spacer sequence in the genome. However, in case the recombination shall result in a replacement of a sequence the spacer sequences are preferably not identical in the genome—the identical spacer sequence are in this case provided with the desired sequence (donor DNA) that shall replace the sequence of interest on an artificial sequence.

By combining monomers of different DNA-recombining enzymes the invention overcomes the limitation of known DNA-recombining enzymes in respect of the target sites they can recombine and provides designer DNA recombining enzymes that are useful for genome editing that can recognize target sequences occurring naturally in a genome.

In a first aspect of the invention the invention provides designer DNA-recombining enzymes that are capable to induce a site-specific DNA recombination to alter a nucleotide sequence in a genome by recombining two non-identical target sequences (preferably naturally) occurring in the genome and a method for preparing the designer DNA-recombining enzymes.

The designer DNA-recombining enzymes according to the invention advantageously does not need target sites that are artificially introduced in the genome and further does not require identical sequences with a length over 8 nucleotides (in particular not 34 nucleotides) to be present, like long terminal repeats (LTRs).

Non-identical target sequences mean in the context of this invention that the target sites differ in at least two nucleotides. Advantageously the target sites may differ even more, in particular in at least three nucleotides. In embodiments of the invention the target sites differ in at least four nucleotides or even eight nucleotides. Advantageously at least 20% or even more preferred 30% of the nucleotides and up to 70% or even up to 90% of the nucleotides in the target sites can differ, which means that the target site may have a sequence identity of only 10 to 80%, preferably 30 to 90%. Each target site comprises a first half site (preferably 10 to 20 nucleotides) and a second half site (preferably 10 to 20 nucleotides) separated by a spacer sequence (preferably 5 to 12 nucleotides). Advantageously one or even both target sites may be asymmetric, meaning that the half sites of the target site are not reverse-complementary to each other. Advantageously at least 20% or even more preferred 30% of the nucleotides and up to 70% or even up to 90% of the nucleotides in the half sites can differ, which means that all the half sites may have a sequence identity of only 10 to 80%, preferably 30 to 90%. In one embodiment, the differences in the target sites lie only in the half sites and the spacer sequences are identical to induce deletion of the sequence of interest. In another embodiment the two spacer sequences are also different to enable replacement of the sequence of interest by providing a synthetic sequence comprising two sequences that are identical to the target sites occurring in the genome surrounding a donor sequence that shall replace the sequence of interest.

In a preferred embodiment the designer DNA-recombining enzymes according to the invention comprises one or two or up to four different monomers. In one embodiment the designer DNA-recombining enzyme comprises four different monomers and each monomer recognizes a different half site: However, it is also possible that the designer DNA-recombining enzyme comprises two or three different monomers whereas one or two monomers recognize an asymmetric target site. It is even possible that the designer DNA-recombining enzyme comprises four identical monomers whereas the designer DNA-recombining enzyme recognize two different asymmetric target sites. Different monomers according to the invention means that the monomers differ in at least 2%, in particular at least 4%, preferably at least 8% of the amino acid residues. Advantageously up to 10% or even up to 30% of the amino acid residues may differ, which means that the monomers may have a sequence identity of only 70 to 98%, preferably 90 to 96% or up to 92%.

Thus the DNA-recombining enzyme according to the invention is either a homotetramer or a heterotetramer comprising two or up to four different monomers.

In a preferred embodiment of the heterotetramer the monomer-monomer interfaces are genetically modified in such a way that only distinct monomers can form tetramers (e. g. as described in the publication Zhang et al. 2015 and in and US 20170058297 A1). By this modification an obligate heterotetramer is formed excluding tetramers comprising only one monomer.

The sequence of interest is a nucleotide sequence to be altered. It is preferably a sequence comprising mutation. According to the invention the term mutation includes all kind of genetic or chromosomal aberrations, in particular point mutations, frame shift mutations, translocations, duplications, deletions or insertions.

Alternatively, the sequence of interest is a sequence that shall be inactivated, in particular a sequence of a pathogen (a microorganism like a bacteria, a virus or a parasite) or an oncogene or another gene, whereas the activity causes a disease or the inhibition of gene activity is known to reduce symptoms. One example is the gene encoding PCSK9 (Proprotein convertase subtilisin/kexin type 9), where it is known that inhibition reduces cholesterol levels and blood concentration of low density lipoprotein particles (LDL).

In case the sequence of interest is an insertion, a duplication or a sequence that shall be inactivated (e. g. a viral sequence), the recombination induced by the DNA-recombining enzyme according to the invention preferably results in a deletion of the inserted sequence or the sequence that shall be inactivated. This deletion—further also referred to as Designer DNA Recombining enzyme induced Gene Deletion (DRiGD)—is achieved by two identical spacer sequences in the two target sites (s. also FIG. 2 for an illustrative example).

Alternatively, the recombination induced by the DNA-recombining enzyme according to the invention results in a replacement of the sequence of interest by a desired sequence. This replacement—further also referred to as Designer DNA Recombining enzyme induced Gene Replacement (DRiGR)—is achieved by providing a synthetic donor sequence comprising the first target site and the second target site, whereas the first and second target site surround the desired sequence. By replacing the sequence of interested by the desired sequence, it is in principle possible to cure any mutation including point mutations, nonsense mutations, frame shift mutations, duplications, and even deletions and insertions (s. also FIG. 1 for an illustrative example).

Advantageously, the DNA recombining enzymes according to the invention allow precise genome editing without triggering endogenous DNA repair pathways and possess the unique ability to fulfill both cleavage and immediate resealing of the processed DNA in vivo.

The term DNA recombining enzyme comprises every enzyme that is capable to induce a site-specific DNA recombination event, preferably a recombinase or integrase, in particular selected from enzymes that carry out a topoisomerase-like reaction, such as serine or tyrosine recombinase families. In one embodiment the known DNA-recombining enzymes whose target sequences are used in step a) and upon which molecular directed evolution is applied in steps (b) are selected from Cre, Dre, VCre, sCre, FLP, Tre (including Tre 1.0 to Tre 3.1 and Bred), Vika, Nigri and Panto.

The term "designer" DNA recombining enzyme refers to the facts that by the invention DNA recombining enzymes are generated to a given target site and that the DNA recombining enzymes do not occur in nature.

In one aspect the invention relates to a method for identifying sequences that are potential target sites for DNA-recombining enzymes that are capable to induce a site-specific DNA recombination of a sequence of interest in a genome, including the steps of:
  i. Screening the genome or a part thereof comprising the sequence of interest for two sequences that are potential spacer sequences. These potential spacer sequences have a length of at least 5 bp, preferably at least 7 bp, more preferably 8 bp and preferably up to 12 more preferably up to 10 bp. One of the potential spacer sequence lies upstream of the sequence of interest and the other potential spacer sequence lies downstream of the sequence of interest. The two sequences have preferably a maximum distance of 100 kb, more preferably 10 kb and even more preferably 2 kb and preferably a minimum distance of 150 bp.
  ii. Identifying (Defining) potential target sites: The potential spacer sequences (obtained in step i.) as well as the sequences surrounding it form the potential target sites. For each potential spacer sequence (obtained in step i.) the neighboring nucleotides, preferably 10 to 20 nucleotides, more preferably 12 to 15 nucleotides, most preferably 13 nucleotides, on one side thereof form the potential first half site and the neighboring nucleotides, preferably 10 to 20 nucleotides, more preferably 12 to 15 nucleotides, on the other side form the potential second half site. Thus, both potential half sites and the spacer sequence in between form a potential target site.
  iii. The potential target sites identified in step ii. are preferably further screened to select for potential target sequences that do not occur (elsewhere) in the genome of the host to insure a sequence specific recombination, in particular a deletion.

This method is in particular suitable to screen for identifying sequences that are potential target sites for DNA-recombining enzymes that induce a deletion (DRiGD) of a sequence of interest in a genome. In this case, the genome is screened in step i. for two identical sequences that are potential spacer sequences. This method is also illustrated by the example in FIG. 18.

In one embodiment the sequence of interest to be deleted is a sequence in the genome of the host, e. g. an oncogene or another gene that shall be inactivated. Thus the genome screened in step i. is the genome of the host itself (or a part thereof comprising the sequence of interest), e. g. the human genome or part of a human chromosome. In this case in step iii. the potential target sequences are preferably screened not to occur elsewhere (thus only around the sequence of interest) in the genome of the host to insure a sequence specific deletion.

In another embodiment the sequence of interest to be deleted is a sequence in the genome of a pathogen, e. g. a virus. Here, step i. is performed on the genome of the pathogen and step iii. on the genome of the host, which is infected by the pathogen. In this case in step iii. the potential target sequences are preferably screened to occur not in the genome of the host (thus only in the genome of the pathogen) to insure a sequence specific deletion.

In a further preferred step iv. target sequences are selected from the list of potential target sequences obtained in step ii or iii. that comprise half sites that have each a homology to a half site of a known target site of a DNA-recombining enzyme. Homology means that a certain number of nucleotide positions bears identical bases. Preferably each half site has at least 10%, preferably at least 20%, preferably at least 30% identical nucleotide positions to a half site of a known target sites of a DNA-recombining enzyme. Further, the half sites preferably a have a homology between each other. Preferably, each half site has at least 10%, preferably at least 20%, preferably at least 30% identical nucleotide positions to the other half site of the same target sites and/or the half sites of the other target site. The homology between target half-sites increases the chance that a monomer can be generated that is active on both half-sites and therefore the number of monomers necessary for recombination is reduced.

The selection of step iii. to insure a sequence specific deletion can be performed either before or after step iv.

Preferably during or before step i. the coordinates of the sequence of interest to be inactivated (preferably a gene or an exon) is determined in the genome. Search windows of 150 bp to 10 kb kB fragments covering the sequence of interest and surrounding sequences are generated. Fragments overlapping with other genes are removed. For all other fragments, potential identical spacer sequences—thus spacer sequences that are repeated at least once are identified.

In one embodiment spacer sequences are selected before step ii. that surround the sequence of interest (e. g. an exon of the gene to be inactivated or at least overlap with the sequence of interest (e. g. the exon). Alternatively, potential target sites are identified as described in step ii and subsequently pairs of target sites are selected that surround the sequence of interest (e. g. an exon of the gene to be inactivated) or at least overlap with the sequence of interest (e. g. the exon).

In another embodiment the method is used for identifying sequences that are potential target sites for DNA-recombining enzymes that induce a replacement (DRiGR) of a sequence of interest in a genome. In this case, the genome is screened in step i. for two sequences that are potential spacer sequences and are not identical. In this case, the potential spacer sequences differ in at least 30% to 100% preferably at least 50% of the nucleotides Thus, in this case the potential spacer sequences preferably have a sequence identity of 0% to 50% or at least below 70%.

In a further preferred embodiment sequences that are potential target sites for DNA-recombining enzymes that induce a replacement (DRiGR) of a sequence of interest in a genome are identified by a method including the steps of:

i. Screening the genome or a part thereof comprising the sequence of interest for two sequences that are potential target sites. These potential target sites comprise a first half site and a second half site with each 10 to 20 nucleotides, more preferably 12 to 15 nucleotides, separated by a spacer sequence with a length of at least 5 bp, preferably at least 7 bp, more preferably 8 bp and preferably up to 12 more preferably up to 10 bp. One of the potential target site lies upstream of the sequence of interest and the other potential target site lies downstream of the sequence of interest. The two sequences have preferably a maximum distance of 100 kb, more preferably 10 kb and even more preferably 2 kb and preferably a minimum distance of 150 bp. To enable a replacement the spacer sequences are chosen to be not identical. The spacer sequences differ in at least 30% to 100% preferably at least 50% of the nucleotides Thus, the spacer sequences preferably have a sequence identity of 0% to 50% or at least below 70%.

ii. The potential target sites identified in step i. are preferably further screened to select for potential target sequences that do not occur (elsewhere) in the genome of the host to insure a sequence specific replacement (with a donor sequence, see below).

In a further preferred step iii. target sequences are selected from the list of potential target sequences obtained in step i or ii. that comprise half sites that have each a homology to a half site of a known target site of a DNA-recombining enzyme. Homology means that a certain number of nucleotide positions bears identical bases. Preferably each half site has at least 10%, preferably at least 20%, preferably at least 30% identical nucleotide positions to a half site of a known target sites of a DNA-recombining enzyme.

The selection of step ii. to insure a sequence specific replacement can be performed either before or after step iii.

Preferably during or before step i. the coordinates of the sequence of the sequence of interest (preferably a gene or exon) to be replaced is determined in the genome. Search windows of 150 bp to 10 kb kB fragments covering the sequence of interest and surrounding sequences are generated. Fragments overlapping with other genes are removed. For all other fragments, potential target sites are identified.

In one embodiment spacer sequences are selected that surround the sequence of interest (e. g. an exon of the gene to be replaced) or at least overlap with the sequence of interest (e. g. the exon).

The method for preparing the designer DNA-recombining enzymes according to the invention enzymes that are capable to induce a site-specific DNA recombination to alter a nucleotide sequence in a genome by recombining two target sequences naturally occurring in the genome (Designer Recombinase-induced Gene Replacement or Deletion), comprises the following steps:

a) Selecting a nucleotide sequence (preferably with a length of 30 to 40 base pairs) up stream of the nucleotide sequence to be altered (site of interest) as first target site and a nucleotide sequence (preferably with a length of 30 to 40 base pairs) downstream of the nucleotide sequence to be altered as second target site, whereas the sequences of the target sites are not identical. The term not identical or non-identical target sequences is defined as above. Advantageously, one or both target sites are asymmetric, as symmetric sites are hardly found in the genome. The target sites each comprise a first half site and a second half site (as defined above, preferably 10 to 20 nucleotides) separated by a spacer sequence (as defined above, preferably 5 to 12 nucleotides). The target sequences are preferably selected to comprise half sites that have each a homology to a half site of a known target site of a DNA-recombining enzyme. Homology means that a certain number of nucleotide positions bears identical bases. Preferably each half site has at least 10%, preferably at least 20%, preferably at least 30% identical nucleotide positions to a half site of a known target sites of a DNA-recombining enzyme. Further, as explained above the half sites preferably a have a homology between each other. Preferably, each half site has at least 10%, preferably at least 20%, preferably at least 30% identical nucleotide positions to the other half site of the same target sites and/or the half sites of the other target site.

b) Applying molecular directed evolution on at least one library, preferably at least two and preferably up to four libraries, of DNA-recombining enzymes using a nucleic acid comprising the first target site and the second target site as selected in a) as substrate, until at least one designer DNA-recombining enzyme is obtained (by molecular directed evolution or a combination of molecular directed evolution and rational design) that is active on the first target site and the second target site as selected in a1).

The designer DNA-recombining enzyme may be selected to target any pair of target sequences and consequently any sequence of interested flanked by these target sites. The target sequences are naturally occurring sequences within a genome of a host (e. g. a cell or organism) or in the genome of a pathogen, like a virus. "Naturally occurring sequences within a genome" means in the context of the invention that the target sequences are not artificially introduced and that both non-identical sequences occur natively (naturally) in the same genome.

Genome is defined as all the genetic material of an organism or pathogen. It generally consists of DNA (or RNA in RNA viruses). The genome includes the genes (the coding regions ore exons), the noncoding DNA (like introns and regulatory sequences) and the genetic material of the mitochondria and chloroplasts.

Preferred target sequences include those that are unique in the target genome of a host cell or organism. As some organism have multiple copies of chromosomes, unique means in this context that they occur only once per set of chromosome.

The inventors have surprisingly found (see example F9-3, which can recombine both loxF9a and loxF9b) that one DNA-recombining enzyme can be used to recombine two different target sites in case all the half sites differ between each other in 7 to 9 of 13 positions.

In general, if all the half sites differ between each other in not more than 7 positions, preferably not more than 5 positions, more preferably not more than 4 positions, one library of DNA-recombining enzymes can be used to evolve an enzyme that can recombine both target sites, in particular in a DRiGR reaction (see FIGS. 15 and 16 and Table on page 63 for an example).

In another case the half sites show a pairwise difference of a maximum of 7, preferably 5, more preferably 4 mismatches—thus both target sites show a maximum of 7, preferably 5 or more preferably 4 mismatches between the half sites. In this case 2 libraries of DNA-recombining enzymes are used to evolve an enzyme that can recombine both target sites.

In a further case only one target site shows a pair of half sites with a maximum of 7, preferably 5, more preferably 4 mismatches—thus the other target site differs in more than 7, preferably 5, more preferably 4 mismatches and also the half sites of the other target site show more than 7, preferably 5, more preferably 4 mismatches compared to each other. In this case 3 or 4 libraries of DNA-recombining enzymes are used to evolve an enzyme that can recombine both target sites.

The library or libraries of DNA-recombining enzymes used in step b) are evolved to obtain one monomer of DNA-recombining enzymes or co-evolved to obtain at least two monomers of DNA-recombining enzymes that work together on the pair of target sites. In case two or more libraries of DNA-recombining enzymes used in step b) they are preferably operationally linked, preferably on one expression vector. In case two or more libraries of DNA-recombining enzymes are used, the libraries are preferably expressed under the control of the same regulatory elements, preferably the same promoter.

Preferably, one or two to four libraries of DNA-recombining enzymes are used in step b) for coevolution. In particular preferred embodiments two or four libraries of DNA-recombining enzymes are used in step b).

In case more than one library is used then the different libraries of DNA-recombining enzymes used differ in respect of the target site specificity.

In case two libraries of DNA-recombining enzymes are used the DNA-recombining enzymes in each library advantageously recognize different asymmetric target sites—target sites composed of two different half sites.

In case four libraries of DNA-recombining enzymes are used the DNA-recombining enzymes in each library preferably recognizes each a different half site of an asymmetric target site. Thus, they only recombine the target site, when co-expressed as heterotetramer.

In a preferred embodiment, the coevolution in step b) is performed using an expression vector that encodes for the library of DNA-recombining enzymes or the at least two different libraries of DNA-recombining enzymes and comprising the first and second target site. In particular, preferred embodiments the expression vector encodes for two or four libraries of DNA-recombining enzymes.

In a preferred embodiment of the vector a negative selection marker lies in between the first and second target site. Thus, the first and second target site, preferably surround a negative selection marker. Thus, in case a recombination occurs the sequence with the negative selection marker is cleaved out and no negative selection occurs. However, if no recombination occurs the negative selection marker is active.

The negative selection marker is in a preferred embodiment a recognition site for a restriction enzyme. Preferably a unique recognition site—meaning a recognition site for a restriction enzyme that occurs only once in the vector. By the incubation with the restriction enzyme expression vectors that have not undergone recombination are linearized. The linearized expression vectors are negative selected, e. g. by choosing a primer pair for a PCR that only amplifies the non-linearized plasmid (as exemplified in FIGS. 4 to 7) and/or by digesting the linearized DNA by an exonuclease.

In a preferred embodiment the negative selection comprises more than one recognition site for a restriction enzyme, preferably two or three (or even up to five) recognition sites for the same or in particular for two to three (or even up to five) different restriction enzymes.

This significantly enhance the efficiency of linearization of the expression vectors that have not undergone recombination. To further enhance the selection for enzymes that result in a replacement an exonuclease is preferably added to digest the linearized DNA.

The substrate nucleic acid comprising the first target site and the second target site (preferably surrounding a negative selection marker) is preferably situated on the same vector as the DNA encoding the library of DNA-recombining enzymes or the at least two different libraries of DNA-recombining enzymes (as exemplified in FIGS. 4 and 7).

In an embodiment, the method comprises also the transduction of a cell with the expression vector as defined above and expression of the DNA-recombining enzyme. Alternatively, a cell-free expression system is used.

In case the DNA-recombining enzyme according to the invention shall result in a deletion (DRiGD), preferably no further DNA substrates or vectors are used for one recombination reaction. A successful recombination cleaves out the negative selection marker and the plasmid is amplified—preferably by PCR (as exemplified in FIGS. 6 and 7—pDuoSLiDE-DRiGD, pQuSLiDE-DRiGD). As described above in this case the first and second target sequences comprises identical spacer sequences (s. also FIG. 2).

The method for identifying sequences that are potential target sites for DNA-recombining enzymes described above is preferably performed when or before selecting the target sites in step a) of the method for preparing designer DNA-recombining enzymes for deletion or replacement.

In case the DNA-recombining enzyme according to the invention shall result in a replacement (DRiGR) a synthetic sequence comprising the first target site and the second target site is used in addition to the substrate. As described above in this case the first and second target sequences comprise different spacer sequences to avoid a deletion to occur. Consequently, the recombination is shifted versus replacement by recombining the identical target sequences on the substrate (on the vector encoding the libraries) and the synthetic sequence. Here the negative selection marker is replaced by recombining with the synthetic sequence.

In a preferred embodiment the synthetic sequence is a replication deficient plasmid (s. also FIGS. 4 and 5 for examples). However, in an alternative embodiment a linear DNA strand is used. In another preferred embodiment the synthetic sequences are on a high-copy number plasmid (s. FIG. 14 for an example).

To further select for DNA-recombining enzyme that result in a replacement the synthetic sequence preferably comprises a positive selection marker between the first and second target. In case a recombination occurs the sequence with the positive selection marker will be inserted into the expression vector and expression vectors bearing the positive selection marker can be positively selected. In one embodiment the positive selection marker is an antibiotic-resistance gene. Thus, after transduction of the vector into cells the cells comprising vectors with the positive selection marker can be easily selected.

In one embodiment (for DRiGR) the vector bears a negative selection marker between the first and second target site and the synthetic sequence additionally comprises a positive selection marker between the first and second target site.

Other negative and positive selection markers are known to a person skilled in the art. Further applicable negative selection markers include gene encoding enzymes that encode a gene encoding a toxin or genes that convert a prodrug into a toxic drug, like URA3 (converting 5-fluoroorotic acid into the toxic compound 5-fluorouracil) or viral thymidine kinases (making the host sensitive to ganciclovir selection). Further applicable positive selection markers are genes encoding for enzymes that can complement an auxotrophy.

One step of molecular evolution preferably comprises at least one selection step and at least one step of mutagenesis. In order that the selected molecules "evolve" between selection steps, the selected candidates are preferably mutagenized so as to introduce mutations into the sequence for testing in the next round of selection. Suitable methods of mutagenesis are known to those of skill in the art and include in particular error-prone PCR, chemical mutagenesis, the use of specific mutator host strains, recursive ensemble mutagenesis, combinatorial cassette mutagenesis and DNA shuffling as well as a combination of these methods.

One or more, preferably, five to fifty, preferably eight to thirty, cycles of co-evolution are preferably be carried out, until DNA-recombining enzymes are evolved that are active on the target sites.

In some embodiments of the invention, the co-evolution step b) can be directly performed on existing libraries of DNA-recombining enzymes.

In a preferred embodiment, the method of the invention comprises the following further steps to obtain the two libraries of DNA-recombining enzymes used in step b). Here step a) is further referred to as step a1)

a2) Identifying four sequences that are half sites of known target sites of DNA-recombining enzymes, whereas the first sequence is homologous to the first half site of the first target site (selected according to a1)), the second sequence is homologous to the second half site of the first target site (selected according to a1)), the third sequence is homologous to the first half site of the second target site (selected according to a1)), the fourth sequence is homologous to the second half site of the second target site (selected according to a1)), Selecting a1) and Identifying a2) are preferably performed simultaneously in one step a), e. g. by a computer program, like the SeLOX algorithm (Surendranath, V. et al. (2010). Preferably the sequences up- and down-stream of the site of interest are compared with known target sites of DNA-recombining enzymes and a target sequence wherein each half site has a certain homology to a half site of a known target site of a DNA-recombining enzyme is selected as described in a1). The half sites of the known target sites identified in this way are the ones mentioned in a2). The degree of homology is preferably as mentioned in a1).

Step a3):

In this step preferably intermediate target sites are generated that are a mix between the half sites identified in step a2) and the target sites as selected in step a1).

The intermediate target sites are preferably generated by determining the nucleotides within the first to fourth sequences (as defined in a2)) that differ from the target sites selected in a1) and replacing one or more, preferably up to three nucleotides that differ by the nucleotides that occur in the corresponding half sites of the target site.

In one embodiment for separated molecular directed evolution of DNA-recombining enzymes on each intermediate target site the intermediate target sites are symmetric, thus they comprise identical or reverse complementary half sites. In this embodiment preferably a set of four intermediate target sites is generated—one intermediate target site for each half site of the target sites selected in a1).

In another embodiment for coevolution of DNA-recombining enzymes a set of preferably two asymmetric intermediate target sites are generated. The first intermediate first target site comprises one sequence that corresponds to the first sequence (as defined in a2)) in which nucleotides are replaced by nucleotides occurring in the first half site of the first target site (as selected in step a1)) and a sequence that corresponds to the second sequence (as defined in a2)) in which nucleotides are replaced by nucleotides occurring in the second half site of the first target site (as selected in a1)). The second intermediate target site that comprises a sequence that corresponds to the third sequence (as defined in a2)) in which nucleotides are replaced by nucleotides occurring in the first half site of the second target site (as selected in step a1)) and a sequence that corresponds to the fourth sequence (as defined in a2)) in which nucleotides are replaced by nucleotides occurring in the second half site of the second target site (as selected in step a1)).

Step a4):

Applying molecular directed evolution on DNA-recombining enzymes recognizing the sequences defined in step a2) using a nucleic acid comprising the intermediate first target site and/or the intermediate second target site as substrate.

In one embodiment the nucleic acid comprises both the intermediate first target site and the intermediate second target and a direct evolution of DNA-recombining enzymes is performed on both intermediate target sites (direct coevolution). The coevolution is preferably performed as described above for step b).

In a preferred embodiment the first rounds of molecular directed evolution are performed as a separated molecular directed evolution of DNA-recombining enzymes (separate evolution) for each intermediate target site (e g. as depicted in FIG. 8). In further embodiment these are followed by one or more coevolution steps.

The step of molecular directed evolution preferably comprises positively selecting for recombination on the intermediate target sites and/or negatively selecting against recombination on other target sites.

In order that the selected molecules "evolve" between selection steps, the selected candidates are preferably mutagenized so as to introduce mutations into the sequence for testing in the next round of selection. Suitable methods of mutagenesis are known to those of skill in the art and include in particular error-prone PCR, chemical mutagenesis, the use of specific mutator host strains, recursive ensemble mutagenesis, combinatorial cassette mutagenesis and DNA shuffling as well as a combination of these methods.

One or more, preferably, eight to forty, preferably fifteen cycles of molecular directed evolution are preferably be carried out, until DNA-recombining enzymes are evolved that are active on the intermediate target sites.

The molecular directed evolution employed is preferably a substrate-linked protein evolution, in particular as described in WO 2002044409 A2. However other directed evolution strategies, such as continuous evolution (WO2012088381 A2) are also applicable.

Then preferably a further set of intermediate target sites is created by further adapting the sequences to the half sites of the target sites (selected in a1)), preferably by replacing one or more, preferably up to three nucleotides that differ by the nucleotides that occur in the corresponding half sites of the target site.

The sub steps of molecular directed evolution, shuffling and creating further sets of intermediate target sites is preferably performed until the intermediate target sites only differ in one to three, preferably one or two, nucleotides per half site from the half sites of the target sites (selected in a1)).

In one preferred embodiment to obtain DNA recombining enzymes that induce a replacement (DRiGR) step b) is carried out in three sub-steps of molecular evolution.

In the first step the library or libraries are evolved as described before for DRiGD without an artificial sequence (thus without a donor vector) to select for recombinases that show at least some activity on the target site, thus DNA recombining enzymes that show at least excision activity. This first step is preferably performed as described before firstly on a first set of intermediate target sites and then optionally on a second set of intermediate target sites and finally on the final target sites.

In a second step the library or libraries of DNA recombining enzymes obtained as result of step i) are evolved using an artificial sequence with a positive selection marker, like an antibiotic resistance gene. The artificial sequence is preferably a replication deficient donor vector. Thus, a plasmid or linear sequence that does not carry an origin of replication that is active in the host cells is used (as exemplified in FIG. 9). The second step is preferably performed on the final target sites. In the second step DNA recombining enzymes are selected that are capable to replace a sequence by DRiGR (which is a more complex reaction than a pure excision). Preferably 5 to 20 cycles, more preferably 8 to 15 cycles, of substrate linked molecular evolution are performed until enzymes are obtained that are active on the final target sites. The use of a replication deficient donor vector in combination with an antibiotic selection marker makes it possible to separate the first recombination reaction (integration) on the first target site, from the second recombination reaction (excision) on the second target site, necessary for a successful DRiGR reaction.

In a third step, molecular evolution is performed with the library or libraries of DNA recombining enzymes obtained as result of step ii) with an artificial sequence without a positive selection marker. The artificial sequence is preferably a donor vector that carries a functional origin of replication that is active in the host cells used (as exemplified in FIG. 14). The third step is preferably performed on the final target sites. Preferably 5 to 20 cycles, more preferably 8 to 15 cycles, of substrate linked molecular evolution are performed until enzymes are obtained that are active on the final target sites. In this third step, DNA recombining enzymes are selected that show a high replacement activity without the need of a positive selection marker and with similar recombination kinetics on target site 1 and target site 2. This is an important point as for many uses (in particular a medical use or also when generating multi cellular organism with a modified sequence) the presence of a positive selection marker (e. g. antibiotic resistance gene) is not a favorable option.

This three-step method has been shown to be very efficient to select for enzymes that induce a replacement (DRiGR) in particular when combined with a vector that comprises one or several recognition sites for the same or in particular for two to three (or even up to five) different restriction enzymes between the target sites.

In general, and throughout this specification, the term "vector" refers to a nucleic acid molecule capable of transporting a nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses—AAV). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

Moreover, certain vectors are capable of directing the expression of genes to which they are operatively-linked. Such vectors are referred to herein as "expression vectors." Common expression vectors of utility in recombinant DNA techniques are often in the form of plasmids.

The expression vector is preferably a plasmid, a virus or an artificial chromosome.

Another object of the invention are the vectors or vector as used in the method.

Preferred expression vectors comprise:
i) One, two, three or four genes each encoding a (different) library of DNA-recombining enzymes, whereas the genes encoding the libraries are under the control of the same promoter,
ii) a substrate nucleic acid comprising the first target site and the second target site that surround a negative selection marker, which is preferably a recognition site of a restriction enzyme, that does only occur once in the expression vector (an unique recognition site).

To select for DNA recombining enzymes that induce a deletion (DRiGD) of the site of interest, no further substrate DNA is needed, as the recombination will solely take place between the intermediate first and intermediate second target site on the expression vector.

To select for DNA recombining enzymes that induce a replacement (DRiGR) of the site of interest by a desired sequence preferably a synthetic nucleic acid (preferably a replication deficient plasmid) comprising the intermediate first target site and/or the intermediate second target site is used as an additional (donor) vector. Preferably, a positive selection marker lies in between the first and second intermediate target site. Thus, the first and second intermediate target site preferably surround a positive selection marker, like an antibiotic resistance gene).

The method according to the invention for preparing DNA-recombining enzymes may comprise the further step of:
c) isolating the nucleic acid of the least one DNA-recombining enzyme obtained in step b) from the library; and preferably
d) cloning the nucleic acid obtained in step c) into a suitable delivery vector.

The invention comprises also the designer DNA-recombining enzymes obtained by the method according to the invention.

With the presented invention the inventors provide a solution for recombination-based genome editing that allows flexible and flawless alteration of genetic information. The methods allow in particular for the generation of DNA-recombining enzymes to replace genetic mutations causing human diseases, or to delete predefined genetic material from cells. Thus, the DNA-recombining enzymes according to the invention are used to alter a nucleotide sequence, in particular to repair a mutation or to delete a sequence from the genome or a sequence introduced by a virus. The mutations that can be repaired according to the invention in particular comprise point mutations, frame shift mutations, deletions and insertions.

Advantageously the DNA recombining enzyme can use target sequences naturally occurring in a genome, including the genome of a host cell, a host organ or a host organism or even the genome of a pathogen, like a virus. An advantage of the invention is that it allows precise site directed altering of DNA without engaging host DNA repair pathways and thereby works without inducing random insertions and deletions (indels).

Thus, the invention comprises also a method to modify the genome by inducing site-specific recombination on naturally occurring target sites that are not identical. The method comprises delivery of a DNA recombining enzyme according to the invention into the host, by either delivery of the protein itself, or introducing and expression of a nucleotide sequence encoding it, either from an mRNA or from a DNA template.

As defined above "naturally occurring" means that the target sites are not artificially introduced—there are natively present in the same genome.

Suitable host cells are in particular eukaryotic cells, including stem cells like hematopoietic stem cells, neuronal stem cells, adipose tissue derived stem cells, fetal stem cells, umbilical cord stem cells, induced pluripotent stem cells and embryonic stem cells. In case of human embryonic stem there are preferably not derived from the destruction of embryos. Further the modification of the human germline and human gametes as host cells are preferably excluded.

Suitable host organs for delivery of a DNA recombining enzyme according to the invention comprise any cell in the body, including bone marrow, the skin, muscles, the liver, the lungs, lymph node and the spleen.

The method according to the invention can be performed in vitro (outside of a living organism) or in vivo. In vitro includes the manipulation of isolated cells and/or organs.

In one aspect, the invention provides a method of replacing or deleting a sequence of interest in a genome as described above.

In one aspect the invention relates to the (preferably non-therapeutic) use of a DNA recombining enzyme according to the invention to create an cell or a (preferably non human) multicellular organism with a knock-out of sequence of interest (e. g. a gene or exon) or carrying a modified sequence (e.g. a transgene).

In the method the DNA recombining enzyme according to the invention or the genes encoding the enzyme according to the invention (one gene per monomer) are introduced into a cell or organism by a delivery method.

The designer DNA-recombining enzyme according to the invention induces a site-specific recombination in a genome on two non-identical target sites that surround a sequence of interest.

To modify the genome by inducing site-specific recombination for deletion (DRiGD) of a sequence of interest (e. g. an insertion or a viral sequence) no additional DNA or RNA is necessary.

To modify the genome by inducing site-specific recombination for replacement (DRiGR) of a sequence of interest (e.g. a point mutation) the DNA recombining enzyme according to the invention a synthetic sequence comprising a desired sequence (Donor DNA) is additionally introduced into the host. The synthetic sequence comprises the desired sequence (Donor DNA) that replaces the sequence of interest, whereas desired sequence is flanked by the first target site and the second target site that are recognized by the DNA recombining enzyme according to the invention.

In another aspect, the invention provides a method of generating a model eukaryotic cell comprising a mutated or altered disease associated-gene or polynucleotide or a mutated or altered sequences, selected from signaling biochemical pathway-associated genes and polynucleotides. Examples of these genes and polynucleotides are listed below in table A to C.

Another application of the invention is to specifically alter a sequence of interest in a genome, in particular by introducing a mutation or introducing or replacing a nucleotide sequence, e. g. to create a model eukaryotic cell or an animal model, which has preferably a particular mutation that corresponds to a human disease and/or which bears a humanized sequence. Advantageously the method allows the targeted generation of animal models without inducing random insertions and deletions (indels) or other unwanted uncontrolled modification of genetic material. In some embodiments, the introduced mutation is associated with an increase in the risk of having or developing a disease.

In a preferred embodiment the method according to the invention is used to create animal models, which are useful for biomedical research, e. g. as models for human diseases. In case the invention is carried out in an animal it is preferably carried out for non-therapeutic use of the animal.

Suitable host organisms include invertebrates and vertebrates, particularly Bovidae, Drosophila melanogaster, Caenorhabditis elegans, Xenopus laevis, medaka, zebrafish, Mus musculus, ratus norvegicus or embryos of these organisms.

However, also plants and fungi as well as their cells can be used as hosts.

In some embodiments, one or more vectors described herein are used to produce a non-human transgenic animal or transgenic plant. In some embodiments, the transgenic animal is a mammal, such as a mouse, rat, or rabbit. In certain embodiments, the organism or subject is a plant. In certain embodiments, the organism or subject or plant is algae. Methods for producing transgenic plants and animals are known in the art, and generally begin with a method of cell transfection. Transgenic animals are also provided, as are transgenic plants, especially crops and algae. The transgenic animal or plant may be useful in applications outside of providing a disease model. These may include food or feed production through expression of, for instance, higher protein, carbohydrate, nutrient or vitamins levels than would normally be seen in the wildtype. In this regard, transgenic plants, especially pulses and tubers, and animals, especially mammals such as livestock (cows, sheep, goats and pigs), but also poultry and edible insects, are preferred.

For introducing and expression of the DNA recombining enzyme into a host a delivery vector can be used or other delivery methods, such as DNA, mRNA or protein packaged in liposomes or nanoparticles (e.g. as described by Wang M et al. (2016)), or electroporation ex vivo, or cell squeeze are also applicable.

The delivery method used depends on the host, host cell or target tissue in the host wherein the sequence of interest shall be altered.

Also, the choice of a delivery vector used depends on the host, host cell or target tissue in the host wherein the sequence of interest shall be altered. Suitable delivery vector are known by the person skilled in the art and include plasmids, artificial chromosomes, retroviral vectors, lentiviral vectors, spumavirus vectors and adenoviral vectors but also agrobacteria harboring shuttle vectors. Advantageous delivery vectors include lentiviruses and adeno-associated viruses, and types of such vectors (in particular adeno associated viral vectors) can also be selected for targeting particular types of cells or tissue The delivery vector preferably comprises a regulatory element. The term "regulatory element" is intended to include promoters, enhancers, internal ribosomal entry sites (IRES), and other expression control elements (e.g. transcription termination signals, such as polyadenylation signals and poly-U sequences). In some embodiments the regulatory element is a cellular, bacterial, a viral or a hybrid promoter, wherein said promoter is preferably a constitutive or inducible promoter. Also the promoter is preferably selected depending on the host, host cell or target tissue in the host. Suitable promotors are also known by the person skilled in the art. Preferred constitutive promoters are selected from the promoters of cytomegalovirus, Rous sarcoma virus, murine leukemia virus-related retroviruses, phosphoglycerokinase gene, murine spleen focus-forming virus or human elongation factor 1 alpha.

For replacement of a sequence of interest (DRiGR) the delivery vector preferably contains also the donor sequence that comprises the two non-identical target sites recognized by the designer DNA-recombining enzyme according to the invention and whereas the target sites surround a desired sequence (Donor DNA) that replaces the sequence of interest, whereas desired sequence is flanked by the first target site and the second target site.

Alternatively, the donor sequence is provided on a separate nucleic acid molecule or vector (e. g. a replication deficient plasmid)

The invention comprises also nucleic acids or vectors encoding for a designer DNA-recombining enzyme according to the invention. In a preferred embodiment the nucleic acids encoding for the monomers of a designer DNA-recombining enzyme according to the invention are one nucleic acid molecule or in one vector. Preferably the monomers of the designer DNA-recombining enzymes are expressed under control of one promotor or other regulatory element.

The invention also comprises a method for transduction of a cell with 1. an expression vector or delivery vector as described above encoding a designer DNA-recombining enzyme according to the invention, whereas the designer DNA-recombining enzyme according to the invention induces a site specific recombination in a genome on two non-identical target sites that surround a sequence of interest
2. a nucleotide sequence as donor sequence that comprises the same two non-identical target sites that surround a desired sequence (Donor DNA) that replaces the sequence of interest, whereas desired sequence is flanked by the first target site and the second target site, and expression of the DNA-recombining enzyme.

The donor sequence can be located on the expression or delivery vector or is provided as separate nucleic acid, preferably a replication deficient plasmid. Preferably, the donor sequence is provided at multiple copies per cell to increase the likelihood of replacement of the target sequence (see also FIG. 3).

In a further aspect the invention relates a set or kit comprising:
i) a designer DNA-recombining enzyme according to the invention or a nucleic acid or vector encoding for a designer DNA-recombining enzyme according to the invention, whereas the designer DNA-recombining enzyme according to the invention induces a site specific recombination in a genome on two non-identical target sites that surround a sequence of interest;
ii) a nucleotide sequence as donor sequence that comprises the same two non-identical target sites that surround a desired sequence (Donor DNA) that replaces the sequence of interest, whereas desired sequence is flanked by the first target site and the second target site. Preferably, the donor sequence is provided at multiple copies per cell to increase the likelihood of replacement of the target sequence (see also FIG. 3).

Again, the donor sequence is either located on the same vector (encoding for the designer DNA-recombining enzyme according to the invention) or is provided as separate nucleic acid, preferably a replication deficient plasmid.

Generally, for a replacement according to the invention (DRiGR) the desired sequence on the donor sequence is preferably a sequence that corresponds to the sequence of interest, but wherein the mutation is replaced by the wild type sequence (a gene or part thereof like an exon) or a functional variant thereof (e. g. a silent mutation or a mutation that increase the activity).

A further important part of the invention is the medical application of the DNA recombining enzymes according to the invention, the nucleic acids or vectors according to the invention or the set/kit according to the invention.

For a medical application the sequence of interest is a "disease-associated" gene or polynucleotide, that is altered to cure the disease, or at least reduce the symptoms or to prolong life.

In one aspect the invention relates to an in vitro method. In this method the invention is applied to isolated cells or organs as described above.

In another aspect the invention relates to a method of the treatment of subject, preferably a human or animal, comprising the step of applying a DNA recombining enzyme according to the invention, a nucleic acid or vector encoding for a designer DNA-recombining enzyme according to the invention or the set according to the invention.

Delivery methods and vectors are preferably selected as described above.

In one embodiment the subject to be treated carries a mutation in a nucleotide sequence (sequence of interest) that causes the subject to suffer from a disease, in particular a mutation that causes a reduced function or loss of function of the gene-product, e. g. a mutation in the factor 9 gene that causes hemophilia. By delivery of the DNA recombining enzyme according to the invention, a nucleic acid or vector encoding it and a donor sequence carrying a desired sequence, a wild type or other functional variant of the gene (or a part thereof—like an exon) the mutant part of the gene is replaced by the desired (functional) sequence. To enable site-specific recombination the desired sequences in the donor sequence is flanked by the target sites for the DNA recombining enzyme.

In another embodiment the subject to be treated carries a nucleotide sequence (sequence of interest) that causes a disease or the inhibition reduces the symptoms thereof. Here the sequence of interest is deleted by applying the method according to the invention and delivery of the DNA recombining enzyme according to the invention, a nucleic acid or vector encoding it. Here, the sequence of interest is in particular a sequence of a pathogen (a microorganism like a bacteria, a virus or a parasite) or an oncogene or another gene, whereas the activity causes a disease or the inhibition of gene activity is known to reduce symptoms (like for example the gene encoding PCSK9).

Further the invention comprises a pharmaceutical composition comprising a DNA recombining enzyme according to the invention, a nucleic acid or vector encoding for a designer DNA-recombining enzyme according to the invention or the set according to the invention as well as suitable carriers.

The sequence of interested targeted by a DNA recombining enzyme according to the invention can be any polynucleotide endogenous or exogenous to the eukaryotic cell. For example, the sequence of interested can be a polynucleotide residing in the nucleus or mitochondria of the eukaryotic cell or a virus integrated into the genome of the host cell or not. The sequence of interested can be a sequence coding a gene product (e.g., a protein) or a non-coding sequence (e.g., an intron or a regulatory polynucleotide).

The sequence of interested targeted by a DNA recombining enzymes according to the invention may include a number of disease-associated genes and polynucleotides as well as signaling biochemical pathway-associated genes and polynucleotides.

A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that is expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown and may be at a normal or abnormal level. Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

The sequence of interested targeted by a DNA recombining enzymes according to the invention may include a number of disease-associated genes and polynucleotides as well as signaling biochemical pathway-associated genes and polynucleotides as listed in the US patent U.S. Pat. No. 8,697,359 B1, the contents of which is herein incorporated by reference in its entirety.

Examples of disease-associated genes and polynucleotides are listed in Tables A and B. Disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Examples of signaling biochemical pathway-associated genes and polynucleotides are listed in Table C.

Mutations in these genes and pathways can result in production of improper proteins or proteins in improper amounts which affect function. Further examples of genes, diseases and proteins are hereby incorporated by reference from U.S. Provisional application. Such genes, proteins and pathways may be the sequence of interest targeted by a DNA recombining enzymes according to the invention.

TABLE A

| DISEASE/ DISORDER | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Aber; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn 1 (DRPLA Dx); CBP (Creb-BP-global instability); VLDLR (Alzheimer's); Atxn7; Atxn10 |

TABLE A-continued

| DISEASE/DISORDER | GENE(S) |
|---|---|
| Fragile X Syndrome | FMR2; FXR1; FXR2; mGLUR5 |
| Secretase Related. Disorders | APH-1 (alpha and beta); Presenilin (Psen1); nicastrin (Ncstn); PEN-2 |
| Other Prion-related disorders | Nos1; Parp1; Nat1; Nat2, Prp |
| ALS | SOD1; ALS2; STEX; FUS; TARDBP; VEGF (VEGF-a; VEGF-b; V EGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vld1r; Uba1; Uba3; CHIP28 (Aqp1, Aquaporin 1); Uchl1; Uchl3; APP |
| Inflammation | 1L-10; IL-1 (1L-1a; IL-1b); 1L-13; IL-17 (IL-17a, CTLA8); IL-17b; IL-17c; IL-17d; IL-17f); Il-23; Cx3er1; ptpn22; TNFa; NOD2/CARD15 for IBD; IL-6; 1L-12 (1L-12a; 1L-12b); CTLA4; Cx3cl1 |
| Parkinson's Disease | x-Synuclein; DJ-1; LRRK2; Parkin; PINK1 |

TABLE B

| DISEASE/DISORDER | GENE(S) |
|---|---|
| Cell dysregulation and oncology diseases and disorders | B-cell non-Hodgkin lymphoma (BCL7A, BCL7); Leukemia (TAL1 TCL5, SCL, TAL2, FLT3, NBS1, NBS, ZNFN1A1, IK1, LYF1, HOXD4, OX4B, BCR, CML, PHL, ALL, ARNT, KRAS2, RASK2, GMPS, AF10, ARH-GEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, NF145, PLZF, PML, MYL, STAT5B, AF10, CALM, CLTH, ARL11, ARLTS1, P2RX7, P2X7, BCR,CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immuno-deficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immuno-deficiencies (CD3E, CD3G, AICDA, AID, HIGM2,TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1 a, IL-1b), IL-13, IL-17 (IL-17a CTLA8)), IL-17b, IL-17c, IL-17d, IL-17f, ll-23, Cx3cr1, ptpn22, TNFa, OD2/CARD15 for IBD, IL-6, IL-12 (IL-12a, IL-12b), CTLA4, Cx3cl1); Severe combined immunodeficiencies (SCIDs) (JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facio-scapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |

TABLE B-continued

| DISEASE/DISORDER | GENE(S) |
|---|---|
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado- Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Occular diseases and disorders | Age-related macular degeneration (Aber, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX,, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |
| Epilepsy, myoclonic, Lafora type, 254780 | EPM2A, MELF, EPM2, NHLRC1, EPM2A, EPM2B |
| Duchenne muscular dystrophy, 310200 | DMD, BMD |
| AIDS, delayed/rapid progression to | KIR3DL1, NKAT3, NKB1, AMB11, KIR3DS1 |
| AIDS, rapid progression to, 609423 | IFNG |
| AIDS, resistance to | CXCL12, SDF1 |
| Alpha 1-Antitrypsin Deficiency | SERPINA1 [serpin peptidase inhibitor, clade A (alpha-1 antiproteinase, antitrypsin), member 1]; SERPINA2 [serpin peptidase inhibitor, clade A (alpha-1 antiproteinase, antitrypsin), member 2]; SERPINA3 [serpin peptidase inhibitor, clade A (alpha-1 antiproteinase, antitrypsin), member 3]; SERPINA5 [serpin peptidase inhibitor, clade A (alpha-1 antiproteinase, antitrypsin), member 5]; SERPINA6 [serpin peptidase inhibitor, clade A (alpha-1 antiproteinase, antitrypsin), member 6]; SERPINA7 [serpin peptidase inhibitor, clade A (alpha-1 antiproteinase, antitrypsin), member 7];" AND "SERPLNA6 (serpin peptidase inhibitor, clade A (alpha-1 antiproteinase, antitrypsin), member 6) |

TABLE C

| CELLULAR FUNCTION | GENES |
|---|---|
| PI3K/AKT Signaling | PRKCE; ITGAM; ITGA5; IRAKI; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1.; IKBKG; RELB; DYRK1A; CDKN1A; ITGB1; MAP2K2; JAK1; AKT1; JAK2; PIK3R1; CHUK; PDPK1; PPP2R5C; CTNNB1.; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAKI; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |

TABLE C-continued

| CELLULAR FUNCTION | GENES |
| --- | --- |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAPK1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKC1; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4, AKT1; JAK2; STAT3; ADAM 10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1.; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAKI; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; P1K3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; RIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |

TABLE C-continued

| CELLULAR FUNCTION | GENES |
|---|---|
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3;GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling Wnt & Beta catenin Signaling | ERBB4; PRKCE; ITGAM; ITGA5; PTEN; PRKCZ; ELK1; MAPK1; TPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2: MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKC1; PTK2; FOS; PIK3CB; PIK3C3; MAPK8; 1GF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKC1; FOS; PIK3CB; P1K3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic, Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon Rl Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |

TABLE C-continued

| CELLULAR FUNCTION | GENES |
|---|---|
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA, PIK3C2A; BTK; LCK; RAF1; IKBKG; RELB, FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A: LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKC1; GNAQ; PPP2R1A; IGF1R; PRKID1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKC1; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKC1; GNAQ; CAMK2A; PRKD1; MAPK3; KRAS; PRKCD; PPP1CC; RAF1; CREBBP; MAP2K2; MAPK1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE21; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1, MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling (Cardiovascular System) | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |

TABLE C-continued

| CELLULAR FUNCTION | GENES |
|---|---|
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |

TABLE C-continued

| CELLULAR FUNCTION | GENES |
| --- | --- |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1, TRPM7; TRPC5; TRPC6; TRPC1; Cnr1; cnr2; Grk2; Trpa1; Pomc; |
| Pain | Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2, BMP-4; Chordin (Chrd); Noggin (Nog); |
| Developmental Neurology | WNT, (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln |

Embodiments of the invention also relate to methods and compositions related to knocking out genes, amplifying genes and repairing particular mutations, including point mutations, frame shift mutations, deletions or insertions.

In yet another aspect of the invention, the invention may be used to correct ocular defects that arise from several genetic mutations.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease. Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

In some embodiments, the condition may be neoplasia. In some embodiments, where the condition is neoplasia, the genes to be targeted are any of those listed in Table A (in this case PTEN asn so forth). In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion-related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

Examples of proteins associated with Parkinson's disease include but are not limited to α-synuclein, DJ-1, LRRK2, PINK1, Parkin, UCHL1, Synphilin-1, and NURR1.

Examples of addiction-related proteins may include ABAT for example.

Examples of inflammation-related proteins may include the monocyte chemoattractant protein-1 (MCP1) encoded by the Ccr2 gene, the C-C chemokine receptor type 5 (CCR5) encoded by the Ccr5 gene, the IgG receptor IIB (FCGR2b, also termed CD32) encoded by the Fcgr2b gene, or the Fc epsilon R1 g (FCER1g) protein encoded by the Fcer1g gene, for example.

Examples of cardiovascular diseases associated proteins may include IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), or CTSK (cathepsin K), for example.

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

Examples of proteins associated Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, for example.

Examples of proteins associated Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C-C motif) Ligand 2 protein (CCL2) encoded by the CCL2 gene, for example.

Examples of proteins associated Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch 1, Notch2, Notch 3, or Notch 4, for example.

Examples of proteins associated with a secretase disorder may include PSENEN (presenilin enhancer 2 homolog (C. elegans)), CTSB (cathepsin B), PSEN1 (presenilin 1), APP (amyloid beta (A4) precursor protein), APH1B (anterior pharynx defective 1 homolog B (C. elegans)), PSEN2 (presenilin 2 (Alzheimer disease 4)), or BACE1 (beta-site APP-cleaving enzyme 1), for example.

Examples of proteins associated with Amyotrophic Lateral Sclerosis may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins associated with prion diseases may include SODI (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins related to neurodegenerative conditions in prion disorders may include A2M (Alpha-2-Macroglobulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRA1D (Alpha-1D adrenergic receptor for Alpha-1D adrenoreceptor), for example.

Examples of proteins associated with Immunodeficiency may include A2M [alpha-2-macroglobulin]; AANAT [arylalkylamine N-acetyltransferase]; ABCA1 [ATP-binding cassette, sub-family A (ABC1), member 1]; ABCA2 [ATP-binding cassette, sub-family A (ABC1), member 2]; or ABCA3 [ATP-binding cassette, sub-family A (ABC1), member 3]; for example.

Examples of proteins associated with Trinucleotide Repeat Disorders include AR (androgen receptor), FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydroxytryptamine (serotonin) receptor 2C), for example.

Examples of neurodevelopmental-associated sequences include A2BP1 [ataxin 2-binding protein 1], AADAT [aminoadipate aminotransferase], AANAT [arylalkylamine N-acetyltransferase], ABAT [4-aminobutyrate aminotransferase], ABCA1 [ATP-binding cassette, sub-family A (ABC1), member 1], or ABCA13 [ATP-binding cassette, sub-family A (ABC1), member 13], for example.

Further examples of preferred conditions treatable with the present invention include may be selected from: Aicardi-Goutières Syndrome; Alexander Disease; Allan-Herndon-Dudley Syndrome; POLG-Related Disorders; Alpha-Mannosidosis (Type II and III); Alström Syndrome; Angelman; Syndrome; Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 [COFS1]; Cerebrotendinous Xanthomatosis; Cornelia de Lange Syndrome; MAPT-Related Disorders; Genetic Prion Diseases; Dravet Syndrome; Early-Onset Familial Alzheimer Disease; Friedreich Ataxia [FRDA]; Fryns Syndrome; Fucosidosis; Fukuyama Congenital Muscular Dystrophy; Galactosialidosis; Gaucher Disease; Organic Acidemias; Hemophagocytic Lymphohistiocytosis; Hutchinson-Gilford Progeria Syndrome; Mucolipidosis II; Infantile Free Sialic Acid Storage Disease; PLA2G6-Associated Neurodegeneration; Jervell and Lange-Nielsen Syndrome; Junctional Epidermolysis Bullosa; Huntington Disease; Krabbe Disease (Infantile); Mitochondrial DNA-Associated Leigh Syndrome and NARP; Lesch-Nyhan Syndrome; LIS1-Associated Lissencephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARX-Related Disorders; Urea Cycle Disorders; COL1A 1/2-Related Osteogenesis Imperfecta; Mitochondrial DNA Deletion Syndromes; PLP1-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodysplasia Punctata Type 1; Roberts Syndrome; Sandhoff Disease; Schindler Disease—Type 1; Adenosine Deaminase Deficiency; Smith-Lemli-Opitz Syndrome; Spinal Muscular Atrophy, Infantile-Onset Spinocerebellar Ataxia; Hexosaminidase A Deficiency; Thanatophoric Dysplasia Type 1; Collagen Type VI-Related Disorders; Usher Syndrome Type I; Congenital Muscular Dystrophy; Wolf-Hirschhorn Syndrome; Lysosomal Acid Lipase Deficiency; and Xeroderma Pigmentosum.

As will be apparent, it is envisaged that the present system can be used to target any polynucleotide sequence of interest. Some examples of conditions or diseases that might be usefully treated using the present system are listed above and examples of genes currently associated with those conditions are also provided there. However, the genes exemplified are not exhaustive.

Example F-9:

In a preferred embodiment for DRiGR the designer DNA-recombining enzyme according to the invention replaces a mutation in exon 8 of the F9 gene that is responsible for hemophilia B. Exon 8 is frequently mutated in severe forms of hemophilia B and mutations that occur in the population are known (www.factorix.org).

In one embodiment, the F9 designer DNA-recombining enzyme is a heterotetramer comprising two different monomers: a monomer with the sequence according to SEQ ID NO. 1 (Rec F9-1) or a sequence with a least 90% sequence identity, more preferably 95% sequence identity to SEQ ID NO. 1 and a monomer with the sequence according to SEQ ID NO. 2 (Rec F9-2) or a sequence with a least 80% sequence identity, preferably 90% sequence identity, more preferably 95% or even 98% sequence identity to SEQ ID NO. 2.

An object of the invention are also designer DNA-recombining enzyme comprising the sequence according to SEQ ID NO. 1 (Rec F9-1) or SEQ ID NO. 2 (Rec F9-2) or a sequence with a least 80% sequence identity, preferably 90% sequence identity, more preferably 95% or even 98% sequence identity to SEQ ID NO. 1 or 2.

```
                                              SEQ ID ID NO. 1 (Rec F9-1):
MSNLQTLHQN LSALLVXAXS DXARKNLMDX FRDRQAFSEH TWXVLLSVCR SWAAWCKLNX    60

RKWFPAEXXD VRDYLLHLQA XGLXVNTIXQ HLXQLNMLHR RSGLPRPGDS NAVSLVMRRI   120

RKENVDAGER VKQALAFERX DFDQVRSLME NSDRCQDIRN LAFLGXAYNT LLRISEXARI   180

RXXDIXRTDG GRMLIHIGRT KTLVSXAGVE KALSLRVTRL VXRWXSVSGV ADDPNNXLXC   240

RVRRNGVAXP SATSQLSTXX LQGXFAAAHR LIYGARDXSG QRYXTWSGHS ARVGAARDMA   300

RAGVSIAEIM QAGGWTTXES VMNYIRNLDS ETGAMVRLLE DXD                    343
```

In the monomer with the sequence according to SEQ ID NO. 1 (Rec F9-1) preferably the following positions bear the following amino acids residues:

X17 is any amino acid, preferably D or G
X19 is any amino acid, preferably T or A
X22 is any amino acid, preferably G or E
X30 is a small unpolar amino acid, preferably selected from V, L, I, A or G, more preferably V or A
X43 is positively charged amino acid, preferably K or R,
X60 is any amino acid, preferably N or D
X68 is any amino acid, preferably P or S
X69 is a positively or negatively charged amino acid, preferably selected form D, E, K or R, more preferably E or K,
X81 is a polar amino acid, preferably selected form S, T, C, K or R, more preferably C or R,
X84 is any amino acid, preferably A or T
X89 is any amino acid, preferably L or Q
X93 is a small amino acid, preferably selected form C, S and A, more preferably C or A,
X140 is any amino acid, preferably I or T
X166 is an unpolar amino acid, preferably selected from I, L or V, more preferably I or V,
X177 is an unpolar amino acid, preferably selected from I, L or V, more preferably I or V,
X182 is an unpolar amino acid, preferably selected from I, L or V, more preferably I or V,
X183 is positively charged amino acid, preferably K or R,
X186 is a polar amino acid, preferably S or T
X206 is any amino acid, preferably A or T
X222 is any amino acid, preferably V or E
X225 is an unpolar amino acid, preferably selected from I, L or V, more preferably I or V,
X237 is a polar amino acid, preferably selected from S, T, C or Y, more preferably Y or C
X239 is an unpolar amino acid, preferably selected from I, L, V or F, more preferably F or I
X249 is a small unpolar amino acid, preferably selected from V, L, I, A or G, more preferably V or A
X259 is any amino acid, preferably F or P
X260 is any amino acid, preferably T or A
X264 is any amino acid, preferably A or D
X278 is any amino acid, preferably L or Q
X284 is an unpolar amino acid, preferably selected from I, L or V, more preferably I or V,
X318 is an unpolar amino acid, preferably selected from I, L or V, more preferably I or L,
X342 is any amino acid, preferably G or D The capital letters stand for the single letter code according to the IUPAC nomenclature.

Preferred sequences according SEQ ID No 1 are selected from sequences according to SEQ ID No 28, SEQ ID No 3 and SEQ ID No 5 and sequences with a least 80% sequence identity, preferably 90% sequence identity, more preferably 95% or even 98% sequence identity to SEQ ID No. 28, SEQ ID No 3 or SEQ ID No 5.

```
                                              SEQ ID ID NO. 2 (Rec F9-2):
MSXLXTLXQN LSAXLXDXXX XEARKNLMDV XRDRQAFSXH TWRVLLSVCR SWAAWCELNN    60

RKWFPAEPED VRDYLLHLQX RGLXVNTIQQ HLXQLNXLHR RSGLPRPGDS NAVSLVMRRI   120

RKENXDAGER VXQALAFERT DFDQVRSLME NSDRCQDIRN LAFLGVAYNT LLRISEIARI   180

RXXDIXRTDG GRMLXHIGRT KTLVSXAGVE KALSLXVTKL VERWISVSGV ADDPNNYLFC   240

RVRRNGVAXP SAXSQLSTXX LQGXFXAAHR LIXGAXDXSG QRYLTWSGHS ARVGAARDMA   300

RAGVSXAEIM QAGGWTTVES VMNYXRNLDS ETGAMVRLLE DGD                    343
```

In the monomer with the sequence according to SEQ ID NO. 2 (Rec F9-2) preferably the following positions bear the following amino acids residues:

X3 is any amino acid, preferably K or N
X5 is any amino acid, preferably P or Q
X8 is any amino acid, preferably H or T
X14 is an unpolar amino acid, preferably selected from I, L or V, more preferably I or L,
X16 is a small unpolar amino acid, preferably selected from V, L, I, A or G, more preferably V or A
X18 is small amino acid, preferably A or G
X19 is any amino acid, preferably T or A
X20 is a polar amino acid, preferably selected from S, T, N or Q, more preferably S or N
X21 is any amino acid, preferably D or G
X31 is an unpolar amino acid, preferably selected form I, L, V and F, more preferably L or F
X39 is a positively or negatively charged amino acid, preferably selected form D, E, K or R, more preferably K or E,
X80 is any amino acid, preferably T or A
X84 is any amino acid, preferably T or A
X93 is any amino acid, preferably C or A
X97 is an unpolar amino acid, preferably selected form I, L, V and M, more preferably L or M X125 is an unpolar amino acid, preferably selected form I, L and V, more preferably I or V X132 is positively charged amino acid, preferably K or R X182 is an unpolar amino acid, preferably selected form I, L and V, more preferably I or V X183 is positively charged amino acid, preferably K or R X186 is a polar amino acid, preferably T or S, X195 is an unpolar amino acid, preferably selected form I, L and V, more preferably I or V X206 is any amino acid, preferably A or T X216 is any amino acid, preferably G or R X249 is a small unpolar amino acid, preferably selected from V, L, I, A or G, more preferably V or A X253 is any amino acid, preferably I or T X259 is any amino acid, preferably P or S X260 is any amino acid, preferably A or T X264 is an unpolar amino acid, preferably selected form I, L and V, more preferably V or I (or L)

X266 is small amino acid, preferably A or G

X273 is an aromatic or heteroaromatic amino acid, preferably H or Y

X276 is any amino acid, preferably K or Q

X278 is any amino acid, preferably A or D

X306 is an unpolar amino acid, preferably selected form I, L and V, more preferably L or I X325 is an unpolar amino acid, preferably selected form I, L and V, more preferably L or I Again the capital letters stand for the single letter code according to the IUPAC nomenclature.

Preferred sequences according SEQ ID No 2 are selected from sequences according to SEQ ID no. 29, SEQ ID No 4 and SEQ ID No 6 and sequences with a least 85% sequence identity, preferably 90% sequence identity, more preferably 95% or even 98% sequence identity to SEQ ID No. 29, SEQ ID No 4 or SEQ ID No 6.

Preferred pairs of monomers to form the F9 designer DNA-recombining enzyme according to the invention bear the amino acids sequences according to SEQ 28 and 29, and in particular SEQ 3 and 4 as well as SEQ 5 and 6.

In another embodiment, the F9 designer DNA-recombining enzyme comprises a sequence according to SEQ ID No. 36 (Rec F9-3) or a sequence with a least 90% sequence identity, preferably 95%, more preferably 98% sequence identity to SEQ ID NO. 36. In this case, the F9 designer DNA-recombining enzyme is preferably a homotetramer.

The F9 designer DNA-recombining enzyme according to the invention has been obtained using the method according to the invention described herein and recognizes the asymmetric loxF9-A and loxF9-A target sites according SEQ ID No 7 and SEQ ID No 8:

| Name | Sequence | SEQ ID No. |
|---|---|---|
| loxF9a | CTCATTACATTTA ACCAAAAT TATCACAATATAA | 7 |
| loxF9b | CCATCTTTTGTTA GATTTGAA TATATACATTCTA | 8 |

These sequences are present in the human genome and flank exon 8 of the F9 gene. The invention comprises a nucleic acid selected from SEQ ID NO. 7 (loxF9a) and SEQ ID NO. 8 (loxF9b) or a sequence with a least 90% sequence identity, preferably a least 95% sequence identity, more preferably at least 99% sequence identity, to SEQ ID NO. 7 or SEQ ID NO. 8 or a nucleic acid sequence reverse complementary to one of these sequences and their use as target site for a DNA recombining enzyme, preferably a F9 designer DNA recombining enzyme according to the invention. In one embodiment these nucleic acids according to the invention have a length of 30 to 40 nucleotides, preferably 32 to 36, more preferably 34 nucleotides.

The invention also comprises nucleic acids and vectors encoding for the F9 designer DNA-recombining enzyme according to the invention.

The invention also comprises a method for transduction of a cell with:
1. a delivery vector comprising a nucleic acid encoding for the F9 designer DNA-recombining enzyme according to the invention,
2. a donor sequence that comprises the loxF9a and LoxF9b sites surrounding a sequence encoding for the exon 8 of the F9 gene or a functional mutant thereof, and expression of the DNA-recombining enzyme.

The donor sequence can be located on the expression or delivery vector or is provided as separate nucleic acid, preferably a replication deficient plasmid. Preferably, the donor sequence is provided at multiple copies per cell to increase the likelihood of replacement of the target sequence (see also FIG. 3 and exemplified in FIG. 11).

The invention further comprises a method for replacing a (non- or malfunctional) mutant exon 8 of the F9 gene in a cell, by introducing into a cell:
a F9 designer DNA-recombining enzyme according to the invention or a nucleic acid or vector encoding and expressing it,
a donor sequence comprising a sequence encoding for the exon 8 of the F9 gene or a functional mutant thereof flanked by the loxF9a and loxF9b target sites,
whereas the F9 designer DNA-recombining enzyme replaces a sequence comprising the mutant exon 8 by the donor sequence by site specific recombination.

The invention also comprises a kit comprising
a F9 designer DNA-recombining enzyme according to the invention or a nucleic acid or vector encoding it,
a donor sequence comprising a sequence encoding for the exon 8 of the F9 gene or a functional mutant thereof flanked by the loxF9a and loxF9b target sites.

In a preferred embodiment, the defective F9 exon 8 sequence is replaced by a donor sequence carrying the hyperactive Padua mutation (R338L) (PMID: 23197580).

Particular preferred donor sequences for the above mentioned methods and the kit are selected from SEQ ID No. 26 (wild type exon 8) and SEQ ID No. 27 (exon 8 with Padua mutation).

The donor sequence can be located on the vector encoding for the F9 designer DNA-recombing enzyme (s. FIG. 11 for an example) or is provided as separate nucleic acid, preferably a replication deficient plasmid.

Preferably, the donor sequence is provided in the above-mentioned methods and the kit at multiple copies per cell (e.g. on an AAV vector) to increase the likelihood of replacement of the target sequence (see also FIG. 11 for an example)).

Example Hex:

In a preferred embodiment for DRiGD the designer DNA-recombining enzyme according to the invention deletes a sequence on the human chromosome 7. This designer DNA-recombining enzyme is further referred to as Hex designer DNA-recombining enzyme and recognizes the asymmetric Hex1 and Hex2 target sites according SEQ ID No 40 and SEQ ID No 41:

| Name | Sequence | SEQ ID No. |
|---|---|---|
| Hex1 | TACACAGTGTATATTGA TTTTTATCAAATGCCTT | 40 |
| Hex2 | TACACAATGTATATTGA TTTTTATCAAATGCCTT | 41 |

In one embodiment, the designer DNA-recombining enzyme is a heterotetramer comprising two different monomers: a monomer with the sequence according to SEQ ID NO. 46 (Hex-R-#7) or a sequence with a least 90% sequence identity, more preferably 95% sequence identity to SEQ ID NO. 46 and a monomer with the sequence according to SEQ ID NO. 47 (Hex-L-#7) or a sequence with a least 80% sequence identity, preferably 90% sequence identity, more preferably 95% or even 98% sequence identity to SEQ ID NO. 47.

In another embodiment, the designer DNA-recombining enzyme is a heterotetramer comprising two different monomers: a monomer with the sequence according to SEQ ID NO. 48 (Hex-R-#30) or a sequence with a least 90% sequence identity, more preferably 95% sequence identity to SEQ ID NO. 48 and a monomer with the sequence according to SEQ ID NO. 49 (Hex-L-#30) or a sequence with a least 80% sequence identity, preferably 90% sequence identity, more preferably 95% or even 98% sequence identity to SEQ ID NO. 49.

The invention also comprises nucleic acids and vectors encoding for the Hex designer DNA-recombining enzyme according to the invention.

In a further aspect the invention includes the DNA recombining enzymes according to the invention, the nucleic acids or vectors according to the invention or the set/kit according to the invention for use in medicine, in particular for the treatment of a disease or condition associated with one of the above-mentioned disease-associated genes or polynucleotides or the above mentioned signaling biochemical pathway-associated genes and polynucleotides.

In a similar aspect the invention includes the preparation of a medicament for the treatment of a disease or condition associated with one of the above-mentioned disease genes or polynucleotides or the above mentioned signaling biochemical pathway-associated genes and polynucleotides comprising the DNA recombining enzymes according to the invention, the nucleic acids or vectors according to the invention or the set/kit according to the invention or using a method according the invention.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

Further the embodiments described in the invention may be combined with each other.

The invention is illustrated by the following figures and non-limiting examples:

FIG. 1 shows a general scheme of a preferred Designer DNA Recombining enzyme induced Gene Replacement (DRiGR) according to the invention. Different monomers R1-4 of DNA recombining enzymes and their respective DNA binding sequences loxR1-loxR4 (half sites of target sites) are shown. The site of interest in the genome (frowny face) is replaced by a desired sequence (smiley).

FIG. 2 shows a general scheme of a Designer DNA Recombining enzyme induced Gene Deletion (DRiGD). Again, different monomers R1-4 of DNA recombining enzymes binding at their respective DNA binding sequences loxR1-loxR4 are shown in the upper scheme. Here the target sites bear each identical 8 bp spacers. The site of interest in the genome (frowny face) is here cut out.

FIG. 3 illustrates that if the donor vector is in excess to the genomic DNA, Gene Replacement induced by the DNA recombining enzyme is driven towards the replacement of the genomic DNA with the donor vector DNA. Preferably, the donor vector is present in multiple copies in the nucleus of the target cell, such as in AAV vectors, which results in efficient repair of cellular mutations.

FIG. 4 demonstrates a general method to obtain a DNA Recombining enzyme for DRiGR by applying a novel directed evolution strategy (Duo-SLiDE DRiGR) that delivers a pair of monomers of DNA recombining enzymes that work in conjunction to recombine two different target sites (white triangle lox 1 and black triangle lox 2) present in the genome starting with a source vector with two libraries of DNA recombining enzymes. Expression of single recombinases in this system is also feasible (s. FIG. 15). R1, R2 and R3 stand for three different restriction enzymes or the respective restriction sites. P1 and P2 stand for two different PCR primers or the respective primer binding sites.

When these monomers of DNA recombining enzymes are expressed in conjunction with a DNA template also carrying the two target sites (here the pDonor plasmid), recombination at both target sites leads to the exchange of the DNA fragments. Because the incoming DNA fragment removes a restriction site from the pDuoSLiDE vector, effective recombinases that promoted the replacement can be amplified by PCR after digestion of the DNA with the restriction enzyme. Cycling through this system in combination with random mutagenesis and DNA shuffling uncovers the most efficient recombinases promoting the reaction. By using an origin of replication (R6K-ori) on pDonor that is inactive in the host, the process of integration through one target site (e.g. lox1) and excision through the other target site (e.g. lox2) can be uncoupled. Furthermore, integration can be identified through antibiotic selection on kanamycin containing plates.

FIG. 5 demonstrates a similar method to obtain a DNA Recombining enzyme for DRiGR by applying a novel directed evolution strategy (QuSLiDE DRiGR) that delivers two pairs of monomers of DNA recombining enzymes that work in conjunction to recombine two different target sites. Here each monomer is directed to one half site of one target site (white triangle lox 1 and black triangle lox 2) present in the genome starting with a source vector with four libraries of DNA recombining enzymes. (R1, R2 and R3 as well as P1 and P2 have the meaning as in FIG. 4.)

If the DNA on the donor vector contains the wild-type allele and the genome contains a disease causing mutation, the gene defect is repaired in cells (s. FIG. 1).

FIG. 6 demonstrates a general method to obtain a DNA Recombining enzyme for DRiGD by applying a novel directed evolution strategy (Duo-SLiDE DRiGD) that delivers a pair of monomers of DNA recombining enzymes that work in conjunction to recombine two different target sites (white triangle lox 1 and black triangle lox 2) present in the genome starting with a source vector with two libraries of DNA recombining enzymes. (R1, R2 and R3 as well as P1 and P2 have the meaning as in FIG. 4.)

When these monomers of DNA recombining enzymes are expressed, recombination between two copies of the pDuo-oSLiDE vector removes a restriction site from the pDuo-oSLiDE vector, effective recombinases that promoted the deletion can be amplified by PCR after digestion of the DNA with the restriction enzyme. Cycling through this system in combination with random mutagenesis and DNA shuffling uncovers the most efficient recombinases promoting the reaction.

FIG. 7 demonstrates a similar method to obtain a DNA Recombining enzyme for DRiGD by applying a novel directed evolution strategy (QuSLiDE DRiGD)) that delivers two pairs of monomers of DNA recombining enzymes that work in conjunction to recombine two different target sites. Here each monomer is directed to one half site of one target site (white triangle lox 1 and black triangle lox 2) present in the genome starting with a source vector with four libraries of DNA recombining enzymes. (R1, R2 and R3 as well as P1 and P2 have the meaning as in FIG. 4.)

This set of monomers allows deleting a site of interest in a Genome (s. FIG. 2).

FIG. 8 shows a method know in the state of the art to obtain a tailored recombinase that works one target sites by substrate-linked protein evolution (SLiPE) (Buchholz F and Stewart A F, 2001). Here the vector only contains one library and two identical target sites (dashed triangles).

FIG. 9 shows the application of the invention to replace a mutation in the exon 8 of the F9 gene by Duo-SLiDE DRiGR. FIG. 9A shows the schematic presentation of exon 8 and flanking sequence of the F9 gene. The two selected target sequences (loxF9a—SEQ ID No. 3 and loxF9b—SEQ ID No. 4) are indicated by triangles (black and white) and the nucleotide sequence and the chromosomal positions are shown. FIG. 9B illustrates the method to obtain the two recombinase monomers F9-1 (SEQ ID No. 1, 3, 5 and 28) and F9-2 (SEQ ID No. 2, 4, 6 and 29) and the replacement reaction. Confirmation that the recombination reactions have happened as predicted was confirmed by DNA sequencing. FIG. 9C shows an agarose gel demonstrating the restriction pattern for pDuoF9 (source) (lane 1) and pDuoF9 (product) (lane 2) after digestion with NdeI and SacI. M=molecular marker.

FIG. 10 shows an exemplary evolution process of adapting the libraries of DNA recombining enzymes to a given target site—here applied to the loxF9a and loxF9b target sites. Here DNA recombining enzymes that are active on the loxF9a site (F9A) were obtained by designing two symmetric intermediate sites AL and AR and performing 20 or 17 cycles of SLiPE (s. FIG. 8). After combining and shuffling the libraries of DNA recombining enzymes obtained 108 cycles of SLiPE were performed on the asymmetric loxF9a site (F9A). Agarose gels of indicated generation cycles are shown, with the line with two triangles indicating the non-recombined band and the line with one triangle showing the size of the recombined band. The grey triangle below the gel pictures indicates the reduced amount of L-arabinose added to the growth medium. To obtain DNA recombining enzymes that are active on the loxF9b site (F9B) a first set of two symmetric intermediate sites BLS and BRS were designed and 9 cycles of SLiPE (s. FIG. 8) were performed. After shuffling the libraries of DNA recombining enzymes again SLiPE was performed on a second set of symmetric intermediate sites BL (30 cycles) and BR (22 cycles) was performed. Finally, after combing and shuffling the libraries of DNA recombining enzymes obtained 17 cycles of SLIPE were performed on the asymmetric loxF9b site (F9B). Finally (not shown) the two libraries of DNA recombining enzymes obtained on the loxF9a site and the loxF9b site were cloned into pDuoF9 (source)—s. FIG. 9.

FIG. 11 illustrates the use the F9 designer DNA recombining enzymes in a therapeutic setting, both F9-1 and F9-2 coding sequences are cloned into a delivery vector (such as an adeno-associated viral vector) together with the donor sequence that contains loxF9a and loxF9b flanking the wild-type, or Padua mutation (R338L) of exon 8 of the F9 gene. Delivery of such a vector into target cells in multiple copies replaces the inactivating mutation in the genome.

FIG. 12 shows the result of a screen of the human PCSK9 Gene on Chromosome 1 for 8 bp repeats. The exons of the PCSK9 Gene are indicated by bold boxes. The 8 bp repeats are separated by at least 150 bp and no more than 2 kb apart and lie in potential target sites (indicated by vertical lines) with a length of 34 bp, that were screened not occurring elsewhere in the genome. The sequences of interests between the potential target sites are indicated by horizontal lines.

FIG. 13 shows the result of a similar screen of the genome of the human papilloma virus 16 (HPV16) for 8 bp repeats that are separated by at least 150 bp and no more than 2 kb apart and lie in potential target sites of 34 bp, that were screened not to occur in the human genome. The sequences encoding for the viral proteins are indicated in bold boxes with arrows (greater-than signs).

FIG. 14 demonstrates a different general method to obtain a DNA Recombining enzyme for DRiGR used in example 3 step 3 by applying a novel directed evolution strategy (SLiDE DRiGR 2.0) that delivers a library of DNA recombining enzymes that recombines two different target sites (white triangle lox 1 and black triangle lox 2) present in the genome starting. R1, R2, R3, R4 and R5 stand for five different restriction enzymes or the respective restriction sites. P3 and P4 stand for two different PCR primers or the respective primer binding sites. When this library of DNA recombining enzymes is expressed in the presence of a DNA template also carrying the two target sites (here the pDonor-ex8 plasmid), recombination at both target sites leads to the exchange of the DNA fragments. Because the incoming DNA fragment removes restriction sites from the pF9 vector, effective recombinases that promoted the replacement can be amplified by PCR after digestion of the DNA with the restriction enzymes R1-3 and RecBCD. Cycling through this system in combination with random mutagenesis and DNA shuffling uncovers the most efficient recombinases promoting the DRIGR reaction.

FIG. 15 highlights the steps of the novel directed evolution strategy (SLiDE DRiGR) used in example 3 step 3. In a sub step 1, pF9 (source) and pDonor are transformed into bacteria. Only if the expression of the recombinases is induced, growth of colonies resistant to the antibiotic can be observed. In sub step 2, the plasmid DNA of the obtained colonies is digested using restriction enzymes R1-3. This will enrich for clones which have undergone successful DRIGR and result in a pure preparation of pF9 (product). The purity of the plasmid preparation is verified with a restriction digest using the enzymes XhoI and XmaI, which shows the unique restriction pattern of pDuoF9 (product). Additionally, DNA sequencing reveals the correct sequence of pF9 (product).

FIG. 16 demonstrates a different general method to obtain a DNA Recombining enzyme for DRiGR by applying a novel directed evolution strategy (Duo-SLiDE DRiGR 2.0) that delivers one or a pair of monomers of DNA recombining enzymes that work in conjunction to recombine two different target sites (white triangle lox 1 and black triangle lox 2) present in the genome starting with a source vector with one or two libraries of DNA recombining enzymes. R1, R2, R3, R4 and R5 stand for five different restriction enzymes or the respective restriction sites. P3 and P4 stand for two different PCR primers or the respective primer binding sites. When these monomers of DNA recombining enzymes are expressed in conjunction with a DNA template also carrying the two target sites (here the high-copy number plasmid pDonor-ex8), recombination at both target sites leads to the exchange of the DNA fragments. Because the incoming DNA fragment removes a restriction site from the pDuoSLiDE vector, effective recombinases that promoted the replacement can be amplified by PCR after digestion of the DNA with the restriction enzyme. Importantly, no antibiotic selection marker is used in this assay. Cycling through this system in combination with random mutagenesis and DNA shuffling uncovers the most efficient recombinases promoting the reaction.

FIG. 17 shows alignment between Cre (state of the art), a recombinase obtained after step 1 of example 3 (R#1), a recombinase obtained after step 2 of example (3R#7-B5), and a recombinase obtained after step 3 of example 3 (F9-3). The alignment shows how additional mutations have arisen during later stages of evolution.

FIG. 19 and FIG. 20 show a more detailed scheme of the method of the invention, exemplified by the DRiGD method and applied to the human genome.

Figures 21A, 21B:
Figure 21C:
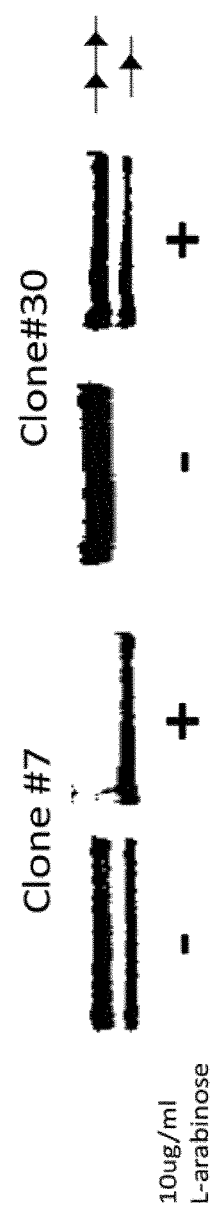

FIG. 21 illustrates the DRIGD method of the invention of applied to a target site on the human chromosome 7—further described in example 5. A. shows the target sites: Hex 1 and Hex 2 are the target sites used for excision—HexL, HexR, HexR1 and HexR2 are intermediate target sites. B. shows the evolution of specific recombinases for the Hex1 and Hex2 target sites. C. shows recombination efficiency of two clones (Clone #7 and Clone #30) obtained.

FIG. 22 shows the precise excision of target sites Hex1 (SEQ ID NO: 40) and Hex2 (SEQ ID NO: 41) from a plasmid substrate using the recombinases obtained in example 5.

EXAMPLE 1

Figure 12:
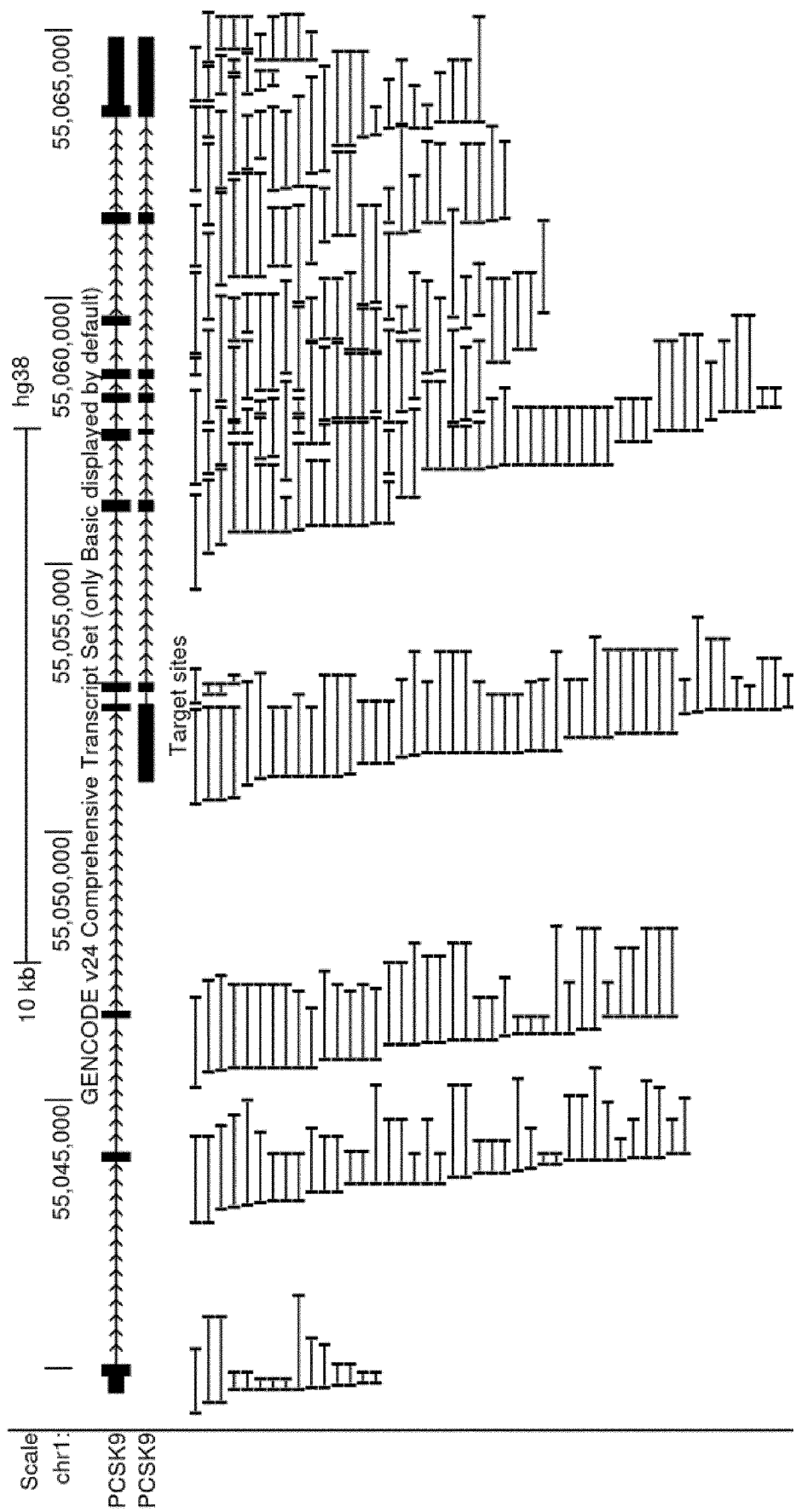
Figure 13:
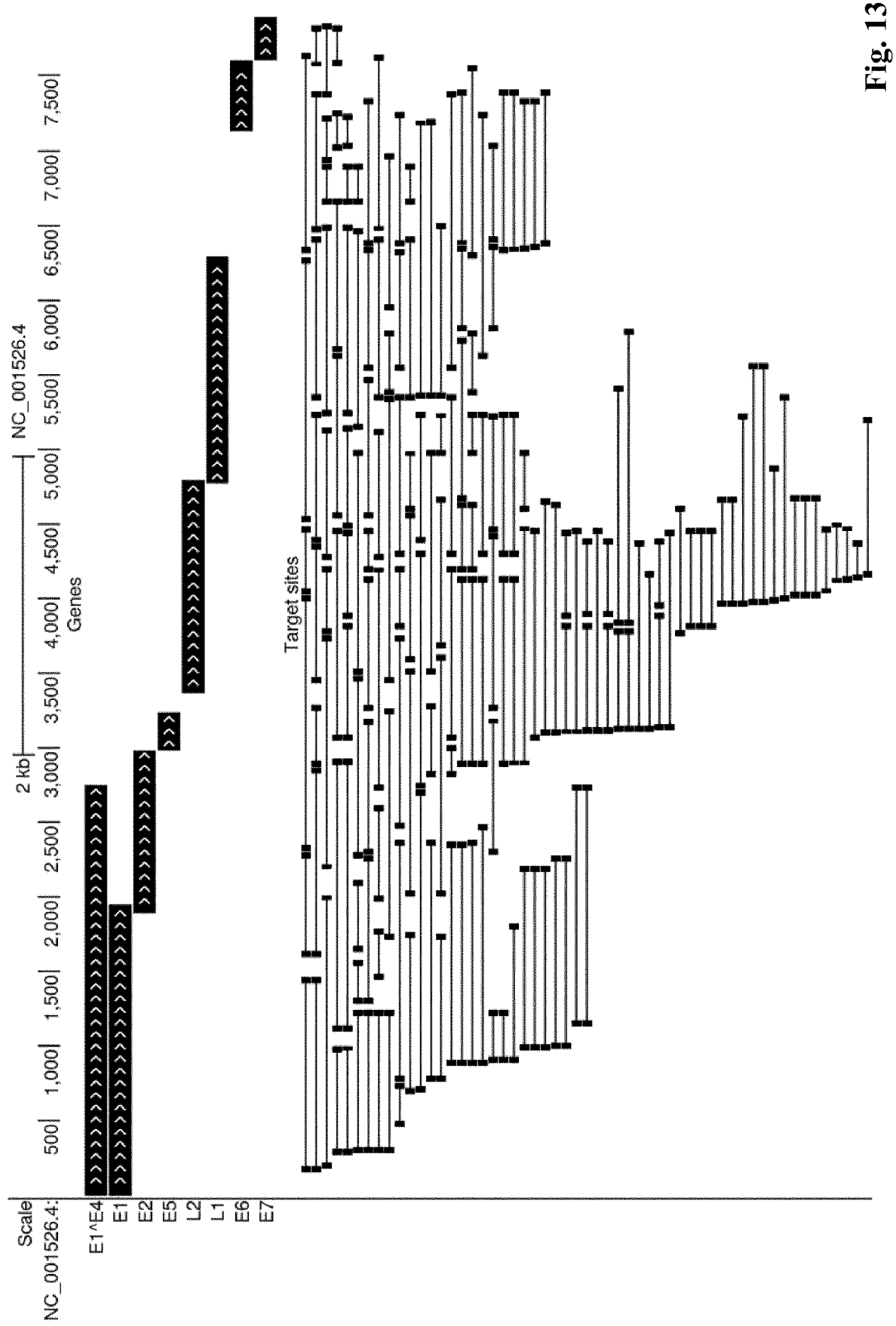

To demonstrate the utility of DRiGD, the inventors have screened the human genome for all 8bp repeats, separated by at least 150 bp: The potential target sites are indicated sequences sequences 13 bp left and 13 bp right of the 8 bp repeat not occurring elsewhere in the human genome in a window to delete a maximum of 2 kb from the genome. FIG. 12 shows the results for all 309 possible target sites for DNA recombining enzymes in the human gene PCSK9. FIG. 13 shows the results for all 176 possible target sites for DNA recombining enzymes in the human papilloma virus 16 (HPV16).

EXAMPLE 2

Figure 1:
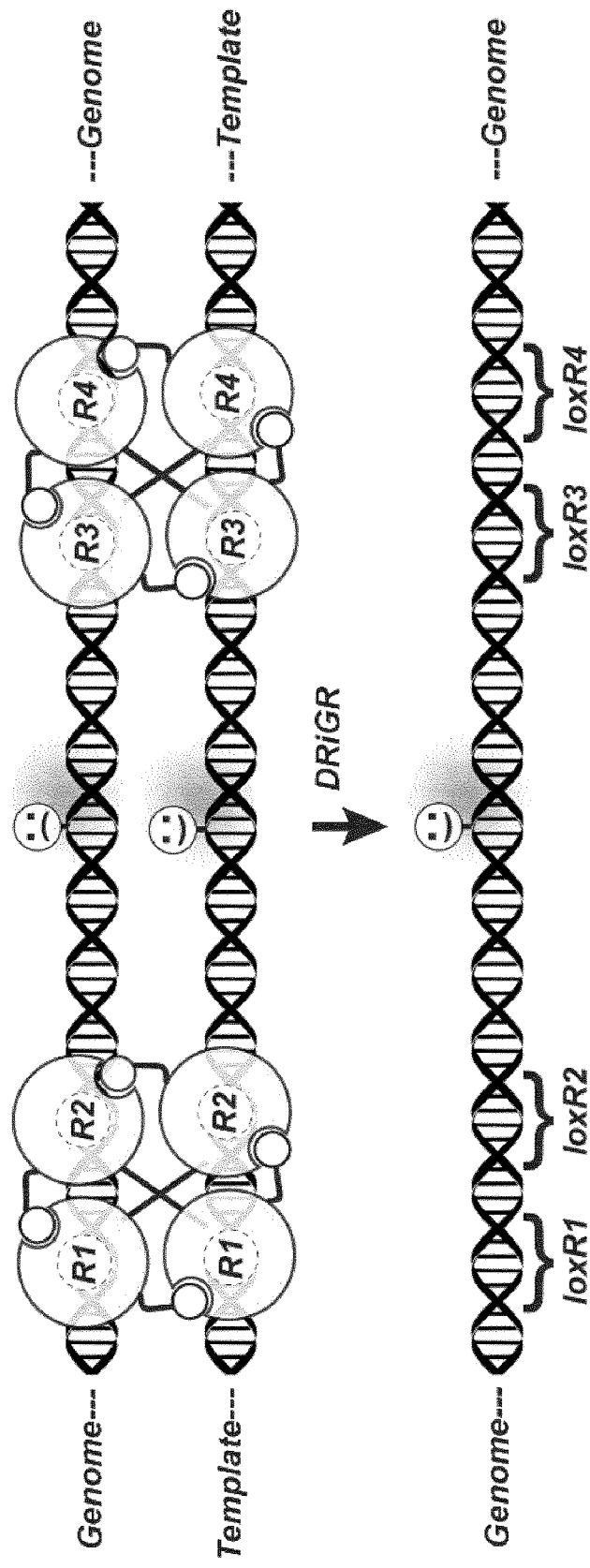
Figure 2:
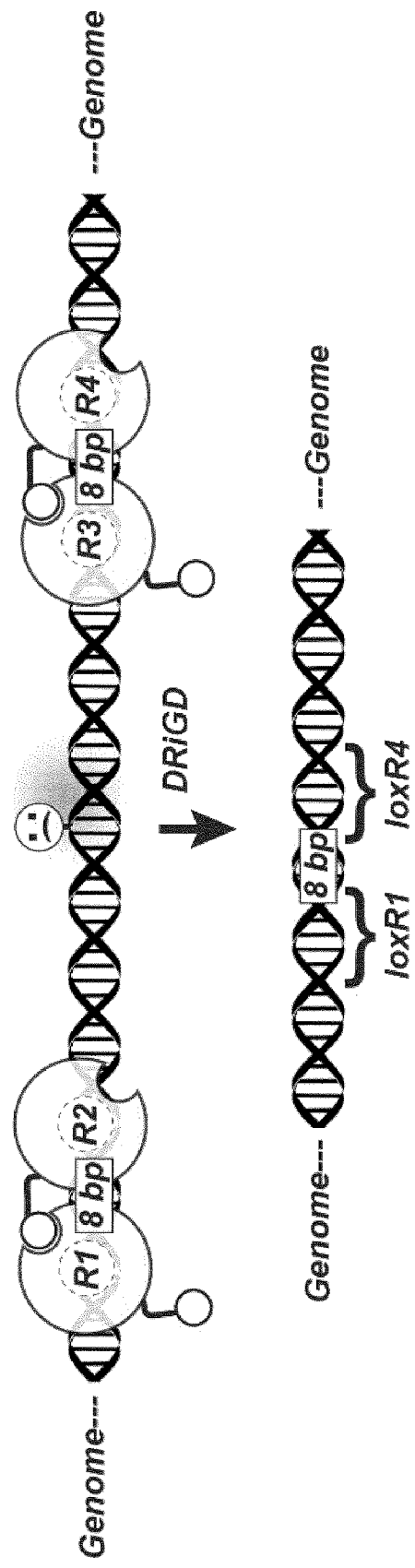
Figure 3:
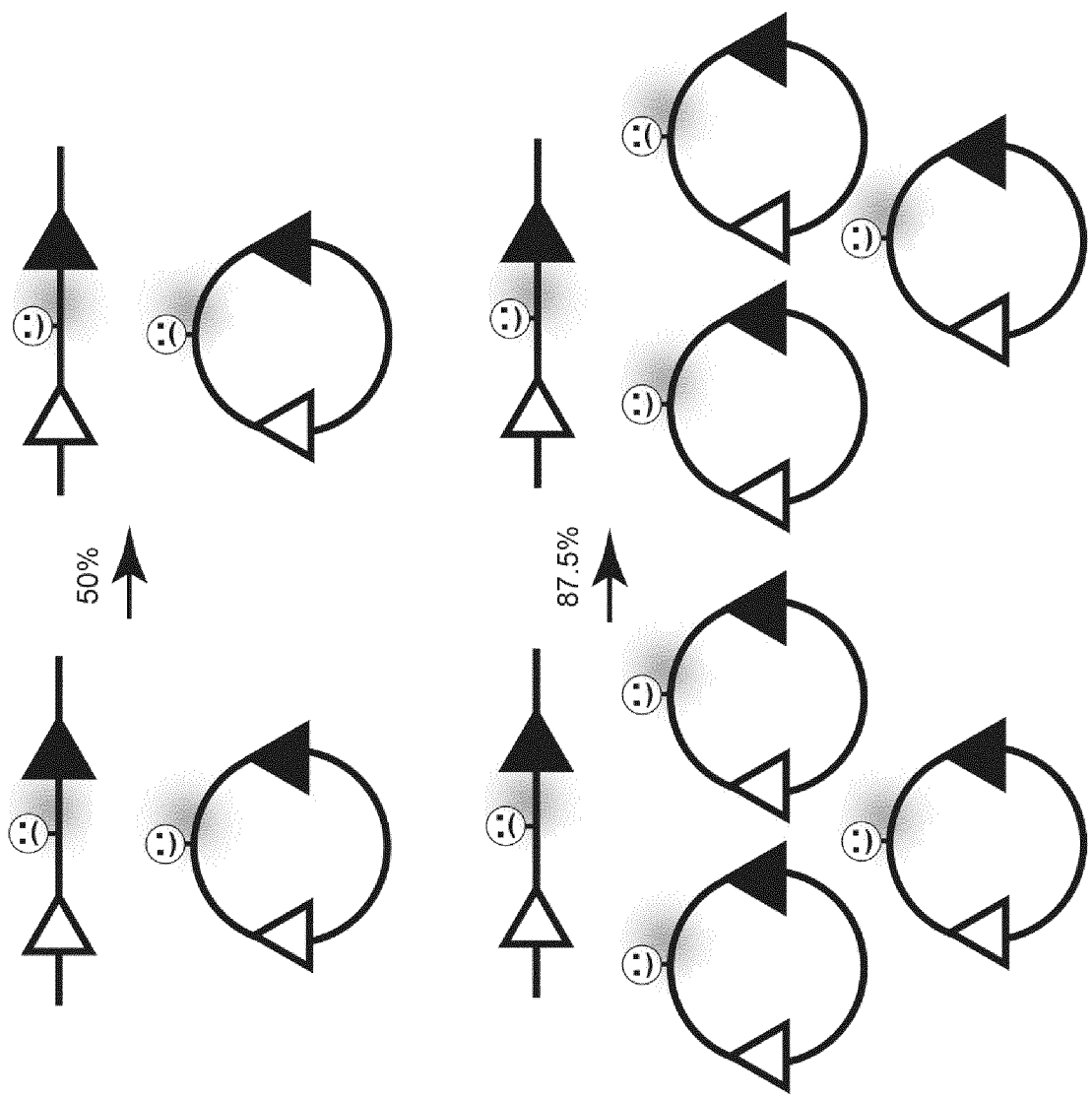
Figure 4:
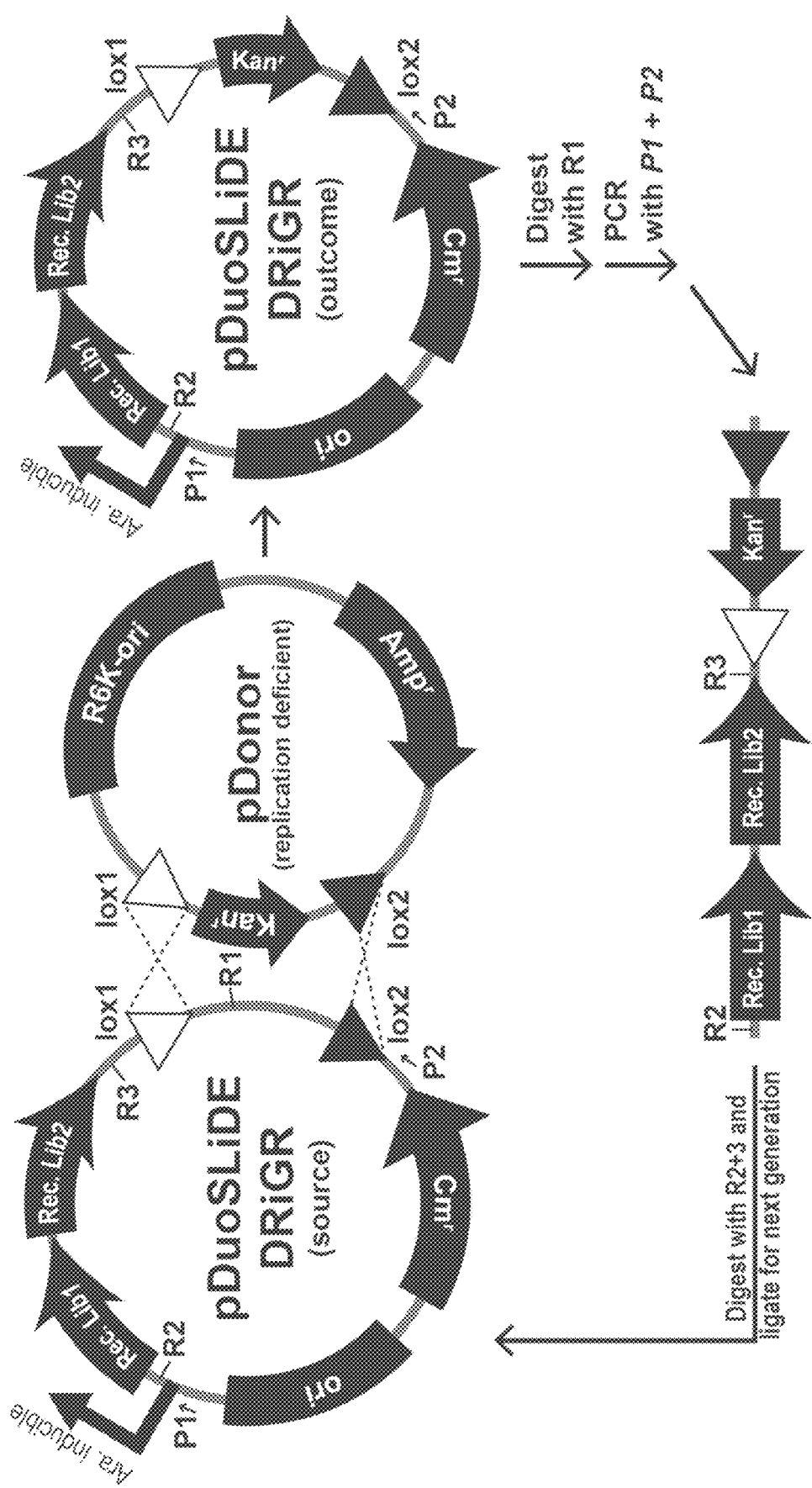
Figure 5:
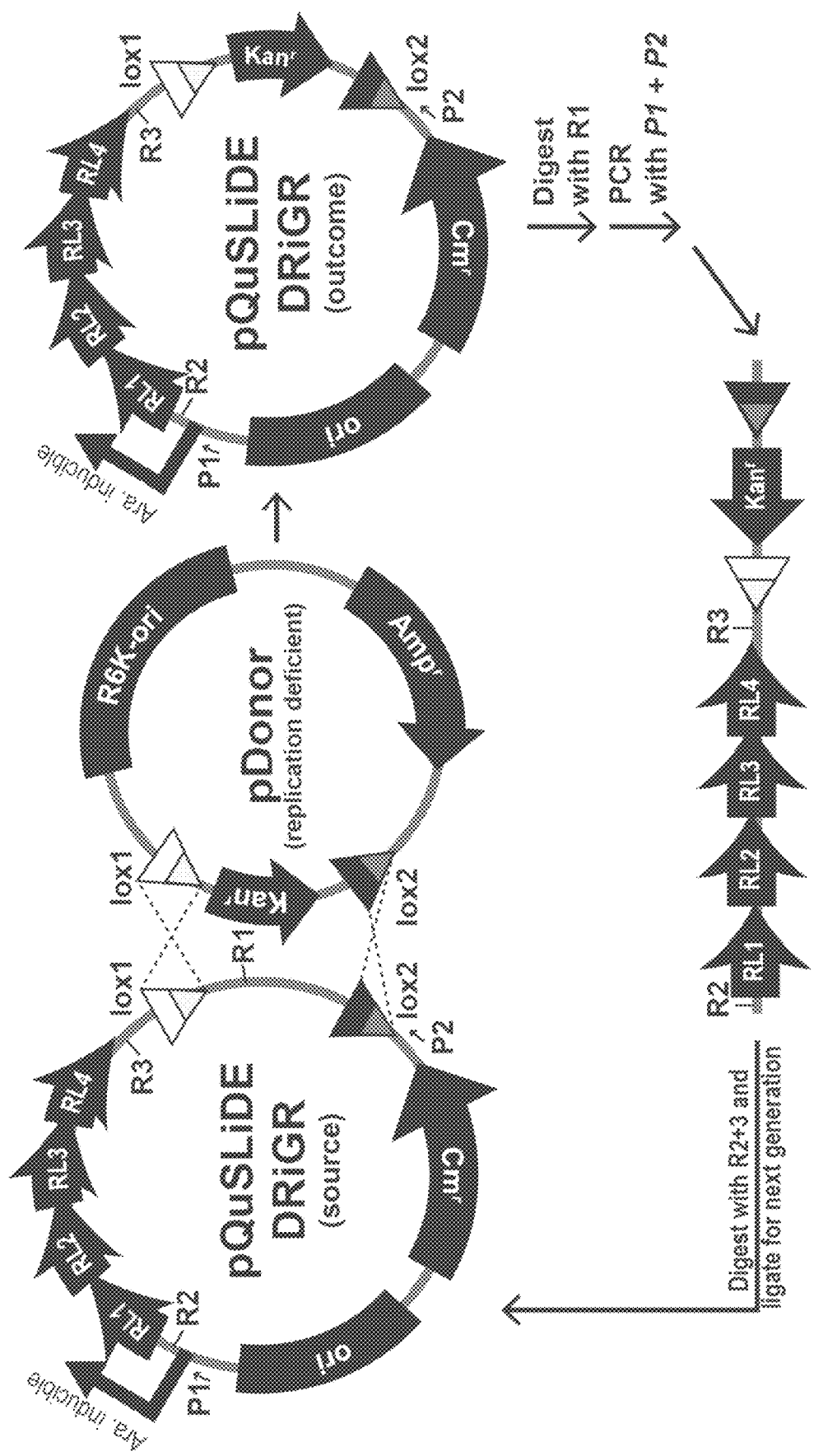
Figure 6:
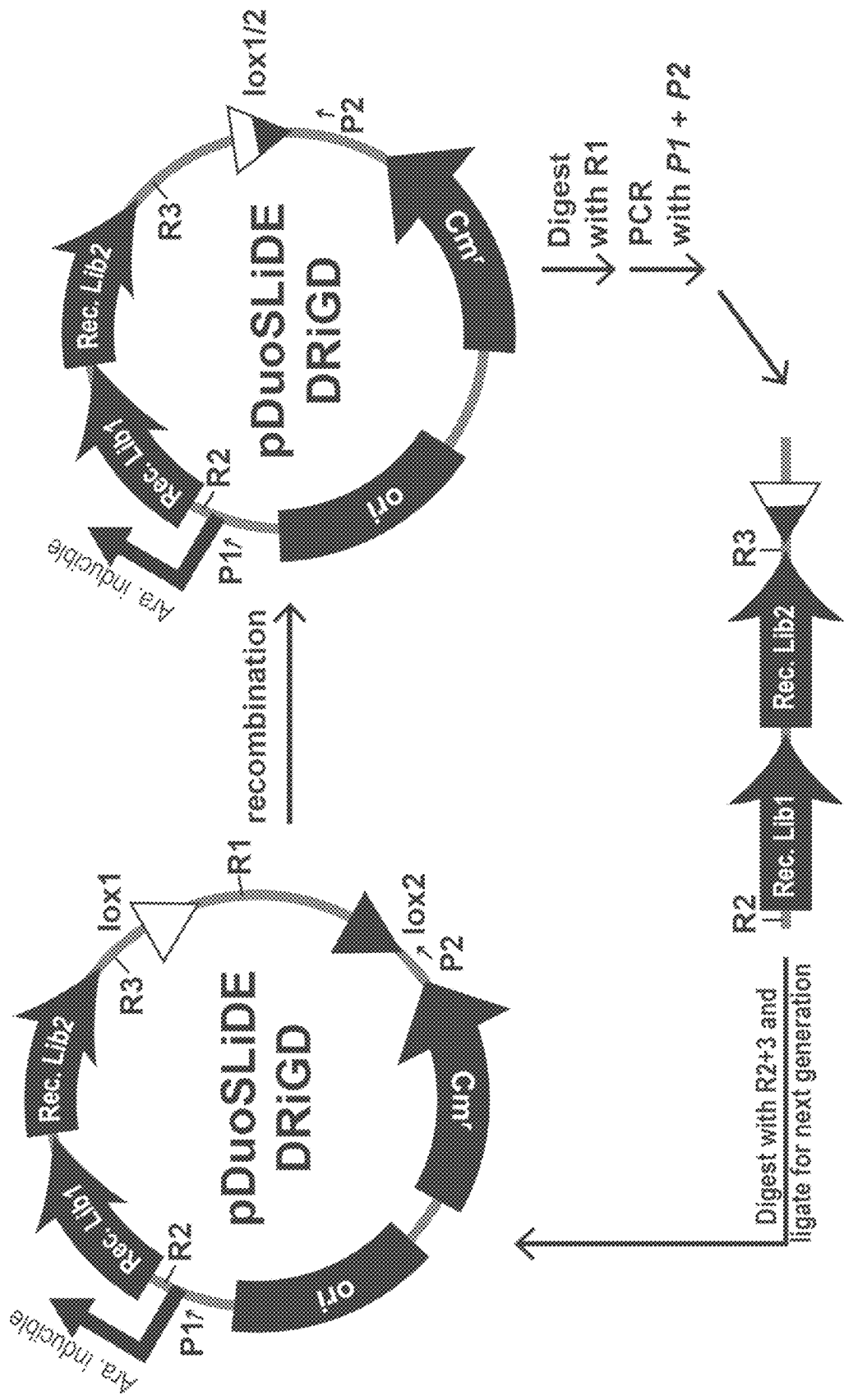
Figure 7:
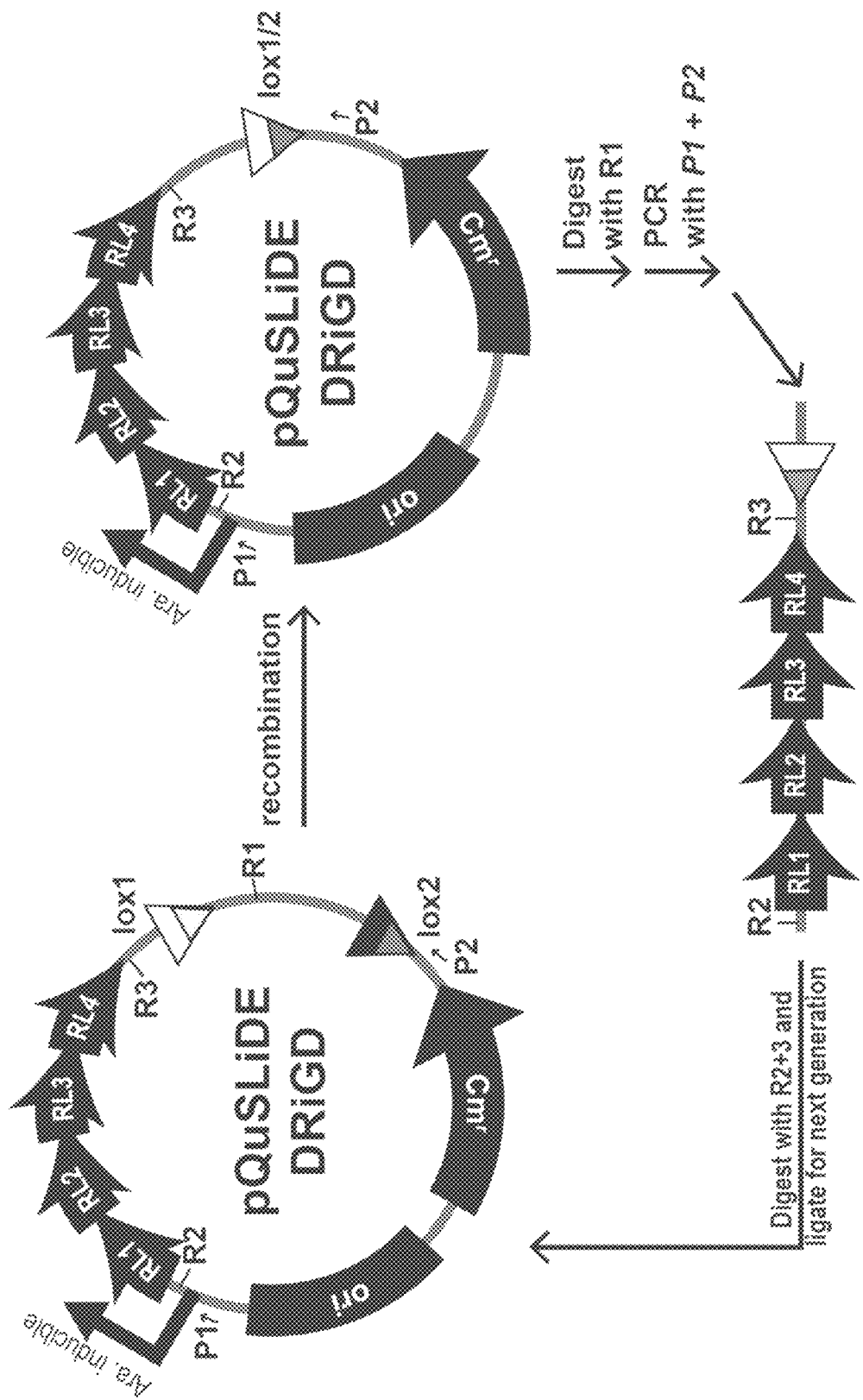
Figure 9:
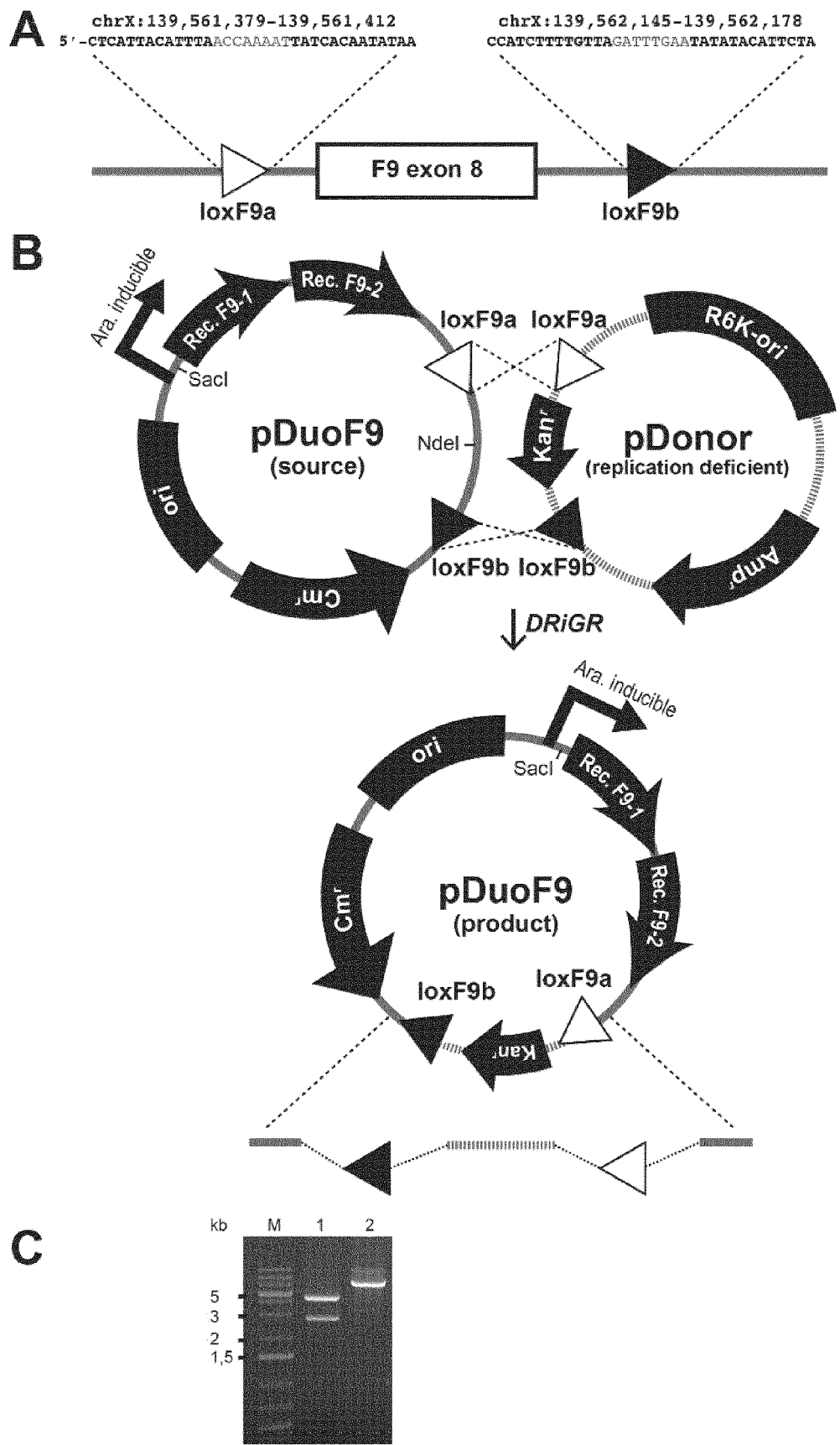
Figure 11:
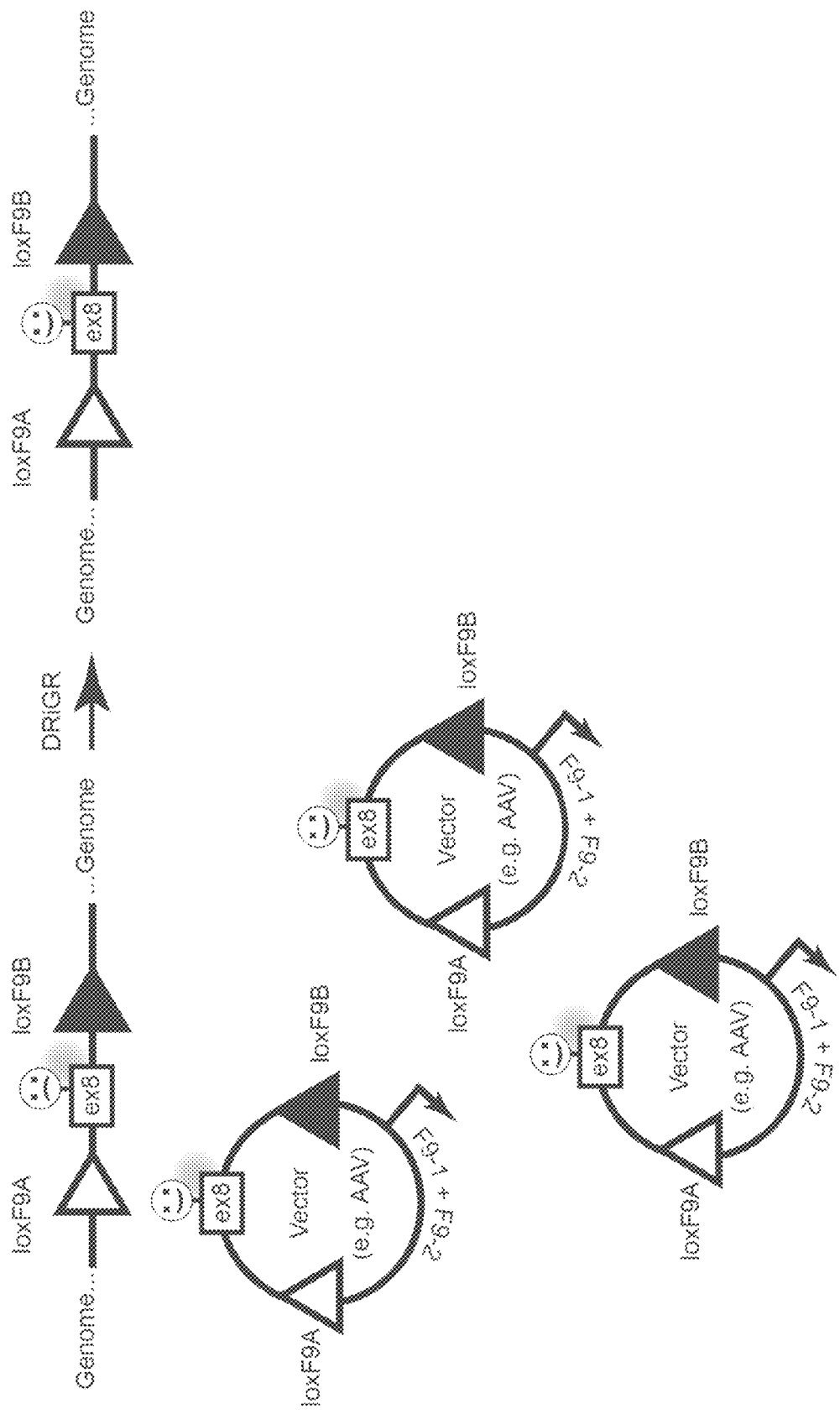

To demonstrate the feasibility of the DRiGR invention, the inventors have generated recombinases that when applied in concert can replace exon eight of the human factor 9 (F9) gene. This exon frequently carries mutations in patients suffering from hemophilia B. Our results demonstrate that this exon can be efficiently replaced for a different sequence providing an appropriate donor vector and expression of two recombinases working in concert (FIG. 6, FIG. 9 and FIG. 11).

Materials and methods as described in WO 2008/083931 A1, WO 2011/147590 A1, WO2016034553 A1 and in the publication Buchholz F and Stewart A F, 2001 are used, if not specified otherwise.

The target sequences (loxF9a—SEQ ID No. 7 and loxF9b—SEQ ID No. 8) were selected by comparing sequences in the human genome with half sites of previously identified target sites (LoxP, LoxH, LoxM7, LoxM5, loxLTR, LoxBTR) of DNA recombining enzymes:

| Name | Sequence | SEQ ID No. |
|---|---|---|
| loxF9a | <u>CTCATTACATTTA</u> ACCAAAAT <u>TATCACAATATAA</u> | 7 |
| loxF9b | <u>CCATCTTTTGTTA</u> GATTTGAA <u>TATATACATTCTA</u> | 8 |
| loxP | <u>ATAACTTCGTATA</u> ATGTATGC <u>TATACGAAGTTAT</u> | 9 |
| loxH | <u>ATATATACGTATA</u> TAGACATA <u>TATACGTATATAT</u> | 10 |
| loxM7 | <u>ATAACTCTATATA</u> ATGTATGC <u>TATATAGAGTTAT</u> | 11 |
| LoxM5 | <u>ATAACTTCGTGCA</u> ATGTATGC <u>TGCACGAAGTTAT</u> | 12 |
| loxLTR | <u>ACAACATCCTATT</u> ACACCCTA <u>TATGCCAACATGG</u> | 13 |
| loxBTR | <u>AACCCACTGCTTA</u> AGCCTCAA <u>TAAAGCTTGCCTT</u> | 14 |

In the table the first (left) and second (right) half sites in the target sites are underlined.

Figure 8:
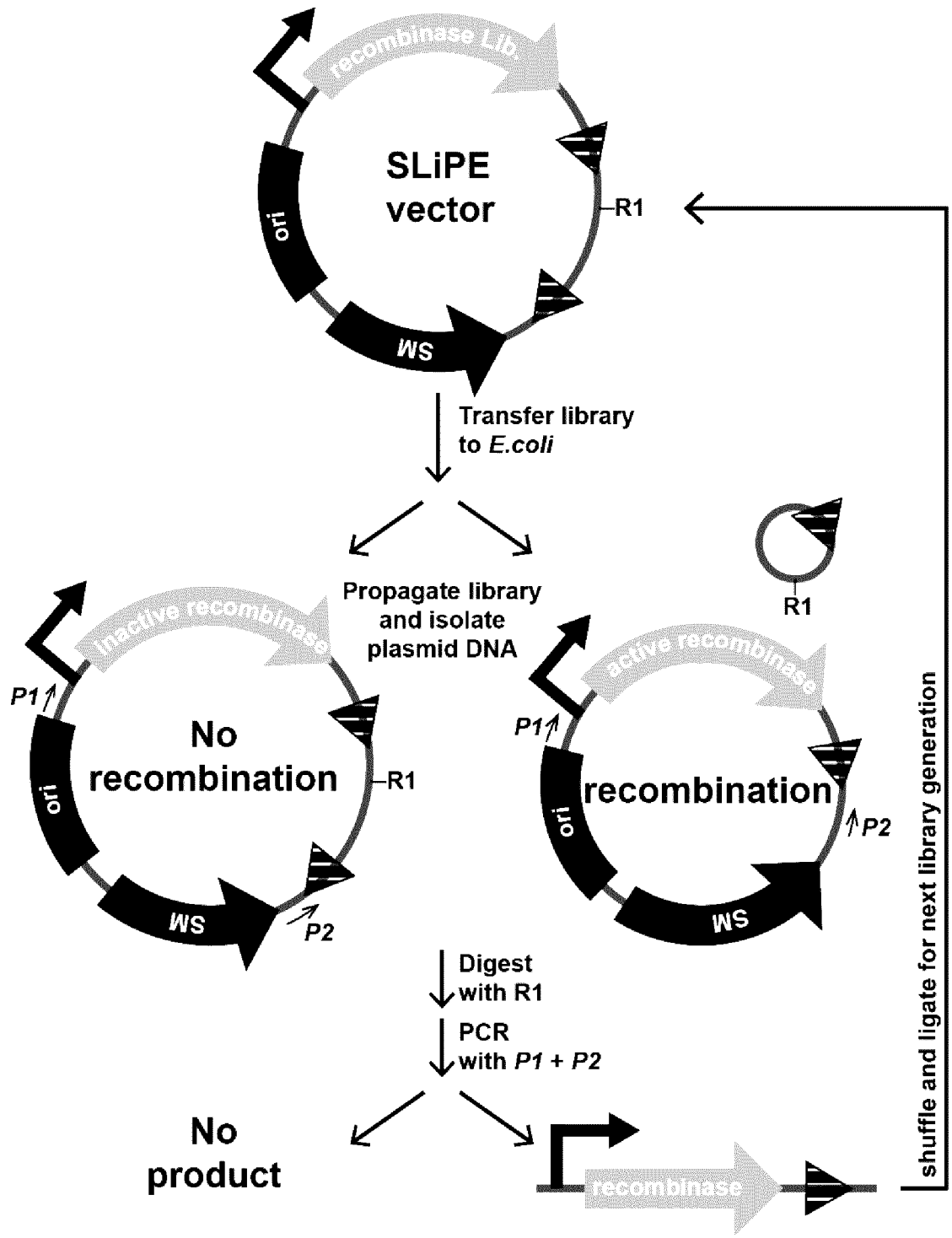

In a first step the two recombinase libraries were evolved separately using the SLiDE approach as described before (Buchholz and Stewart, 2001 and WO 2002044409 A2—s. FIG. 8). In short, each library was evolved towards recombining intermediate target sites (AL, AR, BLS, BLRS, BL, BR) and finally to recombining one of the two target sites, loxF9a or loxF9b. New mutations were introduced through error-prone PCR and DNA-shuffling and selective pressure was further regulated via the expression level of the recombinases. Active recombinases were selected by their ability to recombine the respective target site to delete the sequence flanked by the target sites from the vector (s. FIG. 8).

The following intermediate sequences were used:

| Name | Sequence | SEQ ID No. |
|---|---|---|
| loxF9-AL | <u>CTCATTACATTTA</u> ACCAAAAT <u>TAAATGTAATGAG</u> | 15 |
| loxF9-AR | <u>TTATATTGTGATA</u> ACCAAAAT <u>TATCACAATATAA</u> | 16 |
| loxF9-BLS | <u>CCAACTTTTGATA</u> GATTTGAA <u>TATCAAAGTTGG</u> | 17 |

-continued

| Name | Sequence | SEQ ID No. |
|---|---|---|
| loxF9-BRS | TAGACTTTATATA GATTTGAA TATATAAAGTCTA | 18 |
| loxF9-BL | CCATCTTTTGTTA GATTTGAA TAACAAAAGATGG | 19 |
| loxF9-BR | TAGAATGTATATA GATTTGAA TATATACATTCTA | 20 |

Recombinase coding sequences from these two libraries were then cloned in the vector backbone pDuoF9 (source) (SEQ ID No. 21, s. FIG. 9). In this vector the two recombinase libraries are expressed from a shared inducible promoter in an operon-like structure, which transcriptionally links both enzymes together. The size of this library exceeded 100.000 clones.

To carry out DRiGR, 50 µl of electrocompetent E. coli XL1-Blue cells were transformed with 1 ng pDuoF9 (source) library and grown overnight in 200 ml LB medium containing 15 µg/ml chloramphenicol. On the next day, 1 ml of the overnight culture was used to inoculate 100 ml of fresh medium and grown for 2 h. Then the culture was split into 2×50 ml and L-arabinose was added to a final concentration of 50 µg/ml to induce recombinase expression in one of the cultures. After 2.5 h of incubation the cells were put on ice and prepared for electroporation as described before (Sambrook and Russell, 2001). The electrocompetent cells were resuspended in 200 µl water, and 50 µl of the cell suspension was immediately used for transformation of 0.4 ng pDonor at 1700 V. The bacteria were then allowed to recover for 2 h in SOC medium before the entire suspension was plated on LB agar plates containing 15 µg/ml kanamycin.

No colonies had grown overnight on the agar plates where uninduced cells had been plated, validating that recombinase expression was required for the integration of the pDonor vector (SEQ ID No. 22). All colonies growing from the induced samples were pooled and cultured in 220 ml LB medium containing 15 µg/ml kanamycin and 50 µg/ml L-arabinose to allow possible recombination through the second pair of target sites.

On the next day the plasmid DNA was isolated from the culture. To enrich for clones that had undergone successful DRiGR, the DNA was digested with enzymes cleaving any non-pDuoF9 (product)—negative selection—and re-transformed. To this end, 500 ng of plasmid preparation were digested with 1 µl of each NdeI, AvrII and PspXI. After 3 h incubation at 37° C. DNA was precipitated and resuspended in 50 µl water. 1 µl of this was used for transformation of 50 µl electrocompetent E. coli XL1-Blue cells. The transformed cells were grown in 220 ml LB medium containing 15 µg/ml kanamycin—positive selection—.

Figure 10:
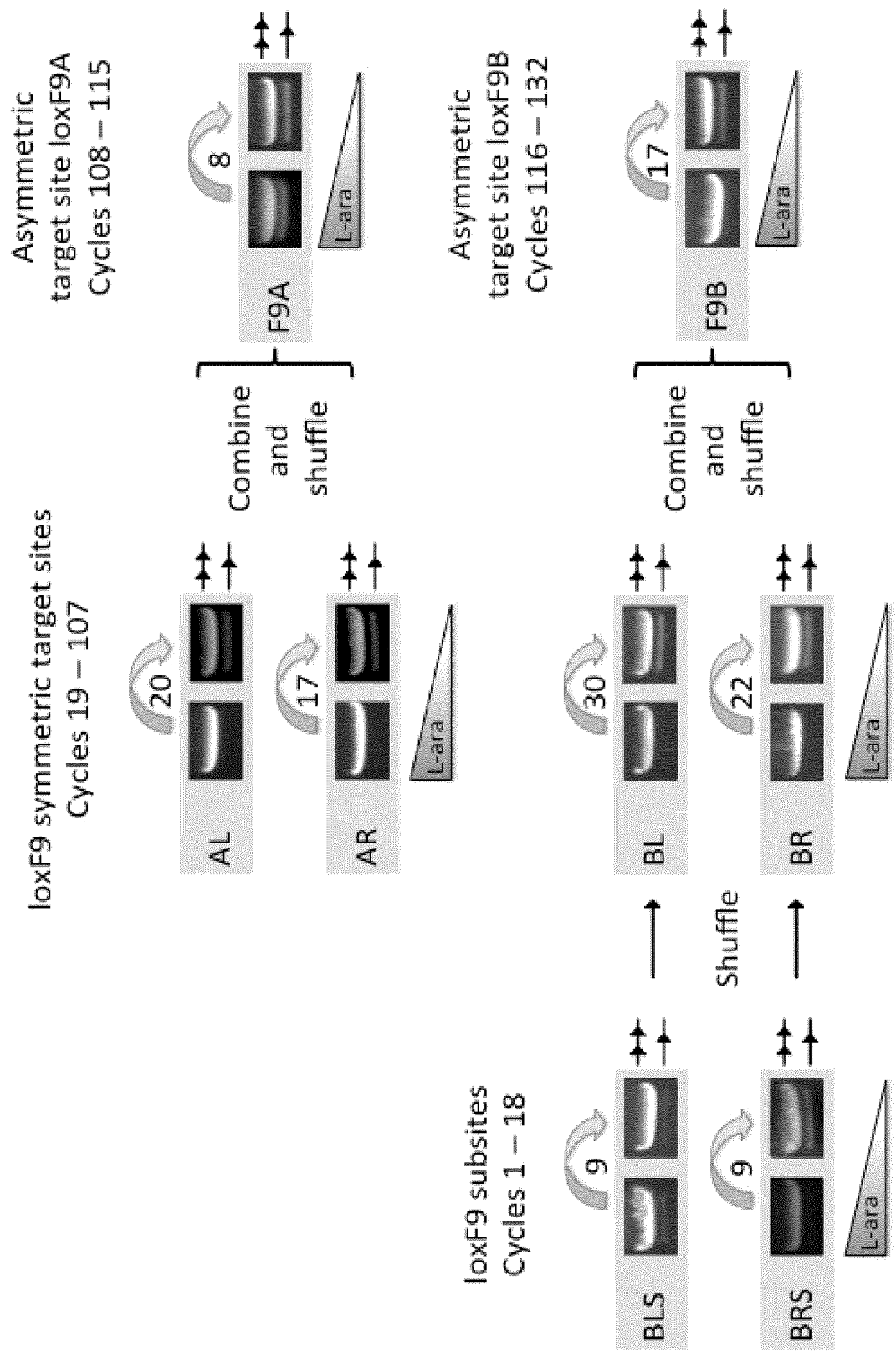

On the next day the plasmid DNA was isolated from the culture. The recombinase libraries were amplified by PCR using primers P1 and P2 (SEQ ID No.23 and 24) and the PCR products were purified on a column and subjected to a digest with the restriction enzymes SacI and SbfI. The isolated recombinase libraries were then ligated back into pDuoF9 (source) to start another cycle of DRiGR. Three rounds of Duo-SLIDE DRIGR (s. FIG. 10) were performed to enrich for recombinases that can efficiently carry out DRiGR on the target sites loxF9a and LoxF9b.

Primer Used:

| Name | Sequence | SEQ ID No. |
|---|---|---|
| P1 | CTCTACTGTTTCTCCATAC | 23 |
| P2 | AGGGAATAAGGGCGACA | 24 |

The sequences of the plasmid pDuoF9 (product) is given in SEQ ID No. 25

By this method the sequences of the following pairs of recombinase monomers were obtained:
Rec F9-1a: SEQ ID No. 3 and Rec F9-2a: SEQ ID No. 4
Rec F9-1b: SEQ ID No. 5 and Rec F9-2b: SEQ ID No. 6

EXAMPLE 3

Step 1:
In a first step the two recombinase libraries were evolved separately using the SLiDE approach as described before (Buchholz and Stewart, 2001 and WO 2002044409 A2—s. FIG. 8). In short, each library was evolved as described in example 2 towards recombining intermediate target sites (loxF9-AL, AR, BLS, BLRS, BL, BR—s. example 2) and finally to recombining one of the two target sites, loxF9a or loxF9b. New mutations were introduced through error-prone PCR and DNA-shuffling and selective pressure was further regulated via the expression level of the recombinases. Active recombinases were selected by their ability to recombine the respective target site to delete the sequence flanked by the target sites from the vector (s. FIG. 8).

Step 2:
In a second step a single recombinase library was evolved to carry out DRiGR following a selection scheme with the replication deficient pDonor (s. FIG. 9). This involved cloning the recombinase coding sequences from the libraries generated in step 1 in the vector backbone pF9 (source) (=pDuoF9 SEQ ID No. 21). In this vector one to four recombinase libraries can be expressed from a shared inducible promoter in an operon-like structure, which transcriptionally links both enzymes together. The size of this library exceeded 100.000 clones.

To carry out DRiGR, 50 µl of electrocompetent E. coli XL1-Blue cells were transformed with 1 ng pDuoF9 (source) library and grown overnight in 200 ml LB medium containing 15 µg/ml chloramphenicol. On the next day, 1 ml of the overnight culture was used to inoculate 100 ml of fresh medium and grown for 2 h. Then the culture was split into 2×50 ml and L-arabinose was added to a final concentration between 1-200 µg/ml to induce recombinase expression in one of the cultures. After 2.5 h of incubation the cells were put on ice and prepared for electroporation as described before (Sambrook and Russell, 2001). The electrocompetent cells were resuspended in 200 µl water, and 200 µl of the cell suspension was immediately used for transformation of 80 ng pDonor at 1700 V. The bacteria were then allowed to recover for 2 h in SOC medium before the entire suspension was used to inoculate 200 ml LB medium containing 15 µg/ml chloramphenicol, 5 µg/ml kanamycin and 1-200 µg/ml L-arabinose. A small part of the suspension was plated on agar plates to estimate the library size.

On the next day it was verified that no colonies had grown on the agar plates where uninduced cells had been plated, validating that recombinase expression was required for the integration of the pDonor vector (SEQ ID No. 22). The plasmid DNA was isolated from the liquid culture. To enrich for clones that had undergone successful DRiGR, the DNA was digested with enzymes cleaving any non-pDuoF9 (product)—negative selection—and re-transformed. To this end, 500 ng of plasmid preparation were digested with 1 µl of each NdeI, AvrII, PspXI and FspI. After 3 h incubation at 37° C. the DNA was cleaned-up via microdialysis on a membrane filter. 3 µl of this digest was used for transformation of 50 µl electrocompetent *E. coli* XL1-Blue cells. The transformed cells were grown in 100 ml LB medium containing 15 µg/ml chloramphenicol and 15 µg/ml kanamycin—positive selection—

On the next day the plasmid DNA was isolated from the culture, and 500 ng of DNA was digested with 1 µl of each NdeI and AvrII. The recombinase libraries were amplified by error-prone PCR using primers P1# and P2# (SEQ ID No. 30 and 31) and the PCR products were purified on a column and subjected to a digest with the restriction enzymes SacI and SbfI. The isolated recombinase libraries were then ligated back into pDuoF9 (source) to start another cycle of DRiGR. After cycles 3 and 8 DNA shuffling was carried out as described before (Buchholz and Stewart, 2001). Eleven rounds of Duo-SLIDE DRIGR were performed to enrich for recombinases that can efficiently carry out DRiGR on the target sites loxF9a and loxF9b.

Figure 14:
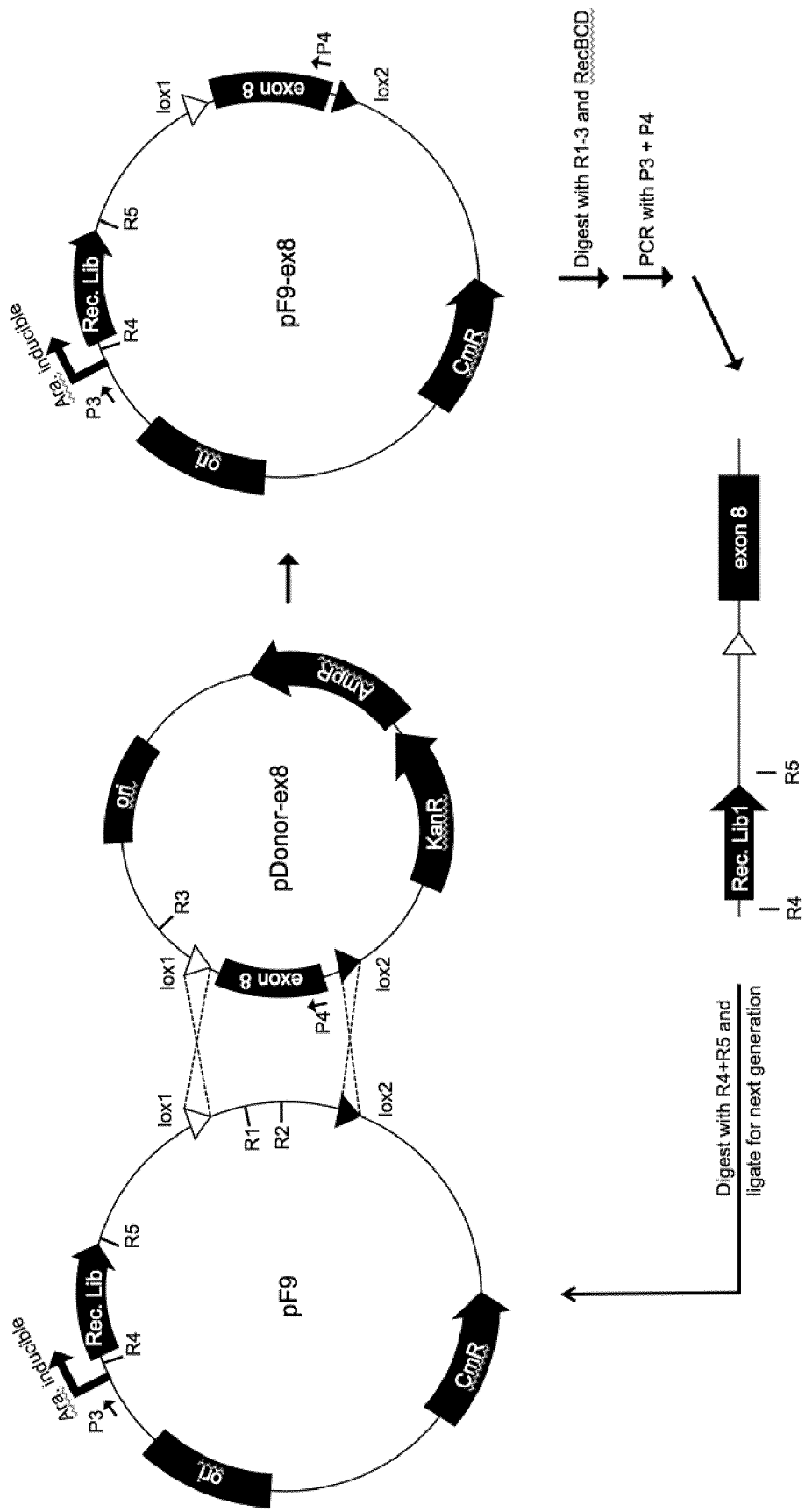

Step 3:

In a third step a single recombinase library was evolved to carry out DRiGR 2.0 following a different selection scheme (s. FIG. 14) with the high-copy number plasmid pDonor-ex8 (s. FIG. 14, SEQ ID 37) without antibiotic selection and without separating integration from resolution of the donor vector. This involved cloning the recombinase coding sequences from the library generated in step 2 in the vector backbone pF9 (source) (=pDuoF9 (source) SEQ ID No. 21). The library was then transformed into electrocompetent *E. coli* XL1-Blue cells which were already carrying pDonor-ex8. The transformed cells were grown in 100 ml LB medium containing 15 µg/ml chloramphenicol, 5 µg/ml kanamycin and 1-200 µg/ml L-arabinose. The size of this library exceeded 100.000 clones.

Figure 15:
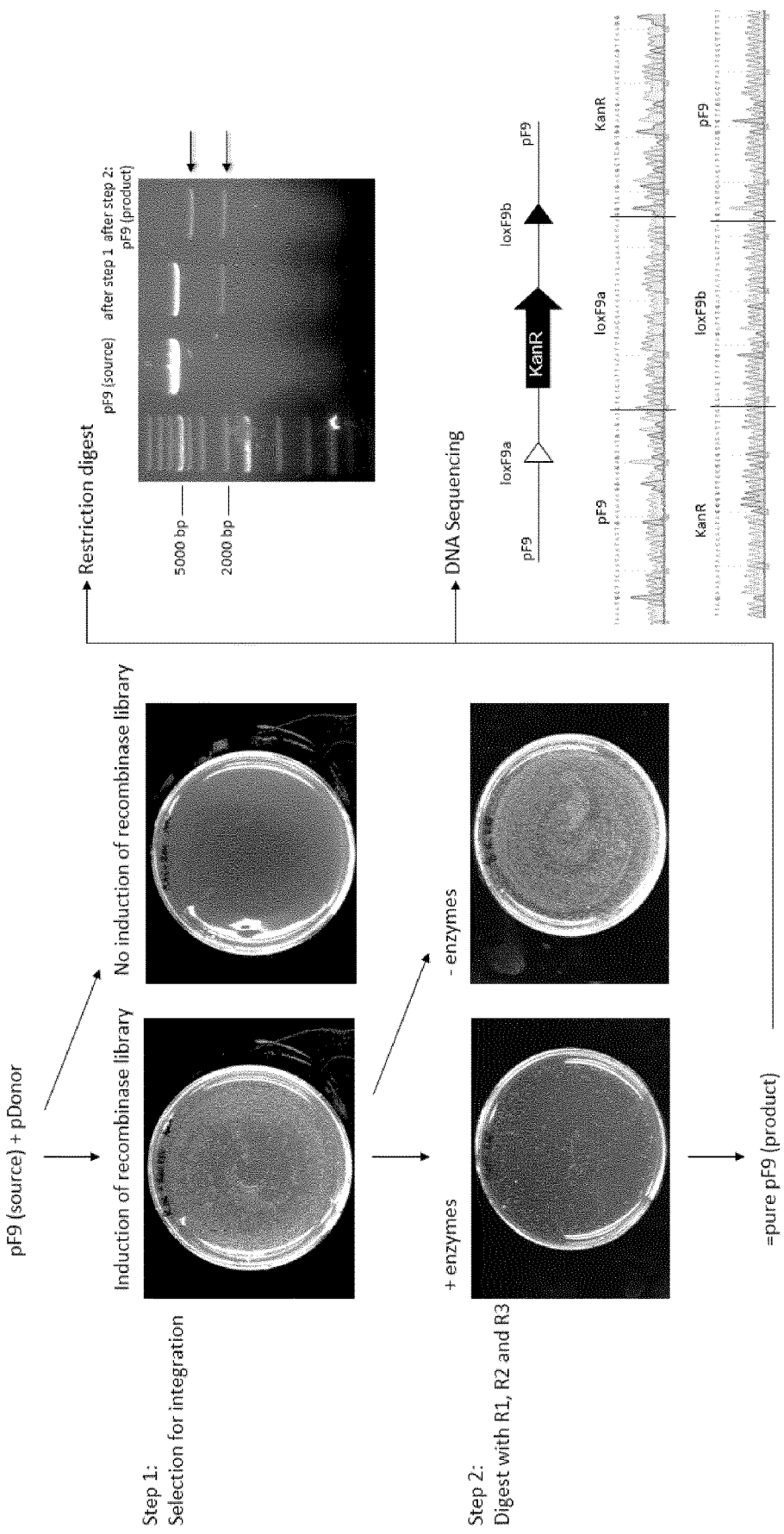
Figure 16:
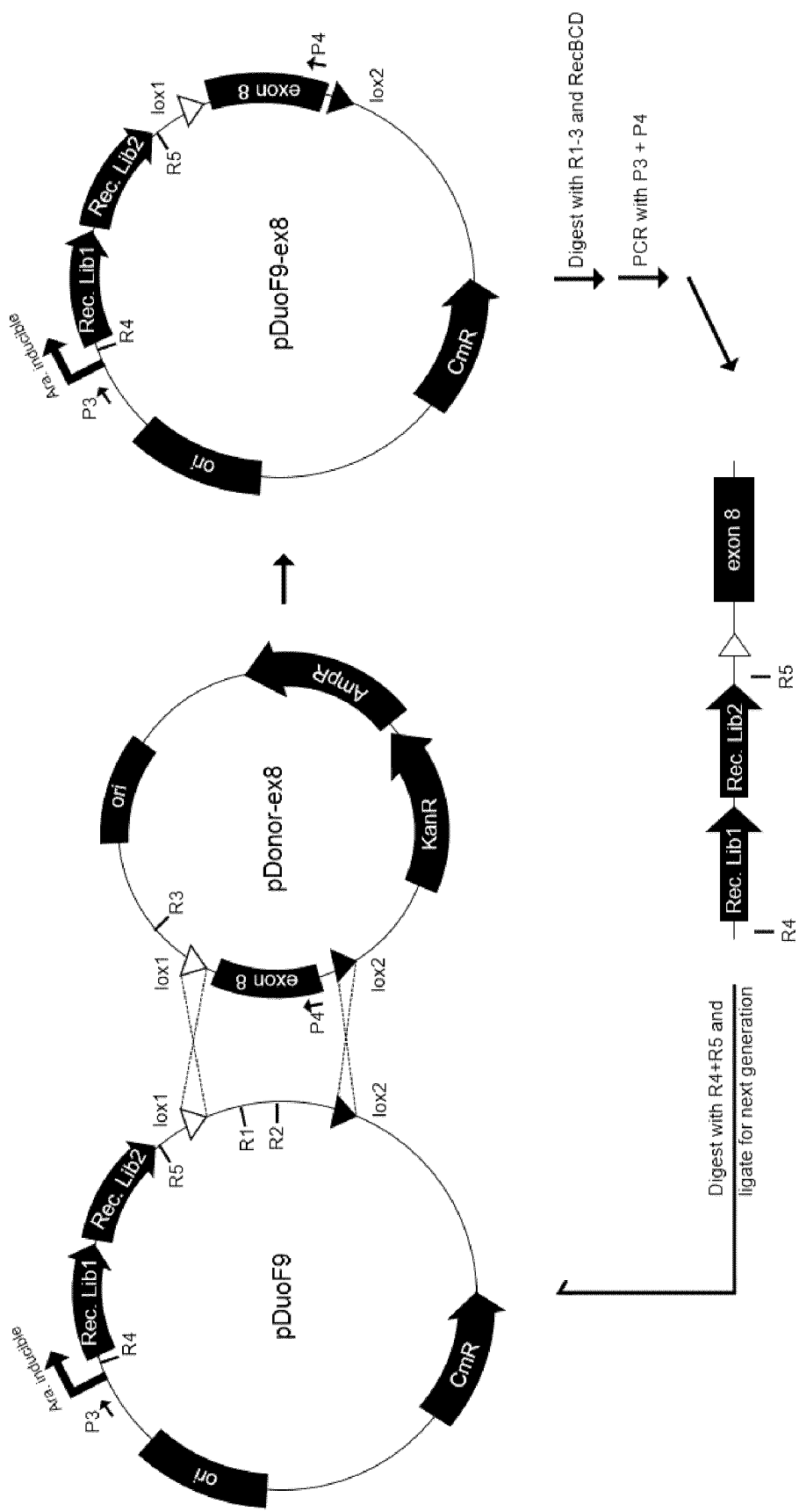
Figure 18:
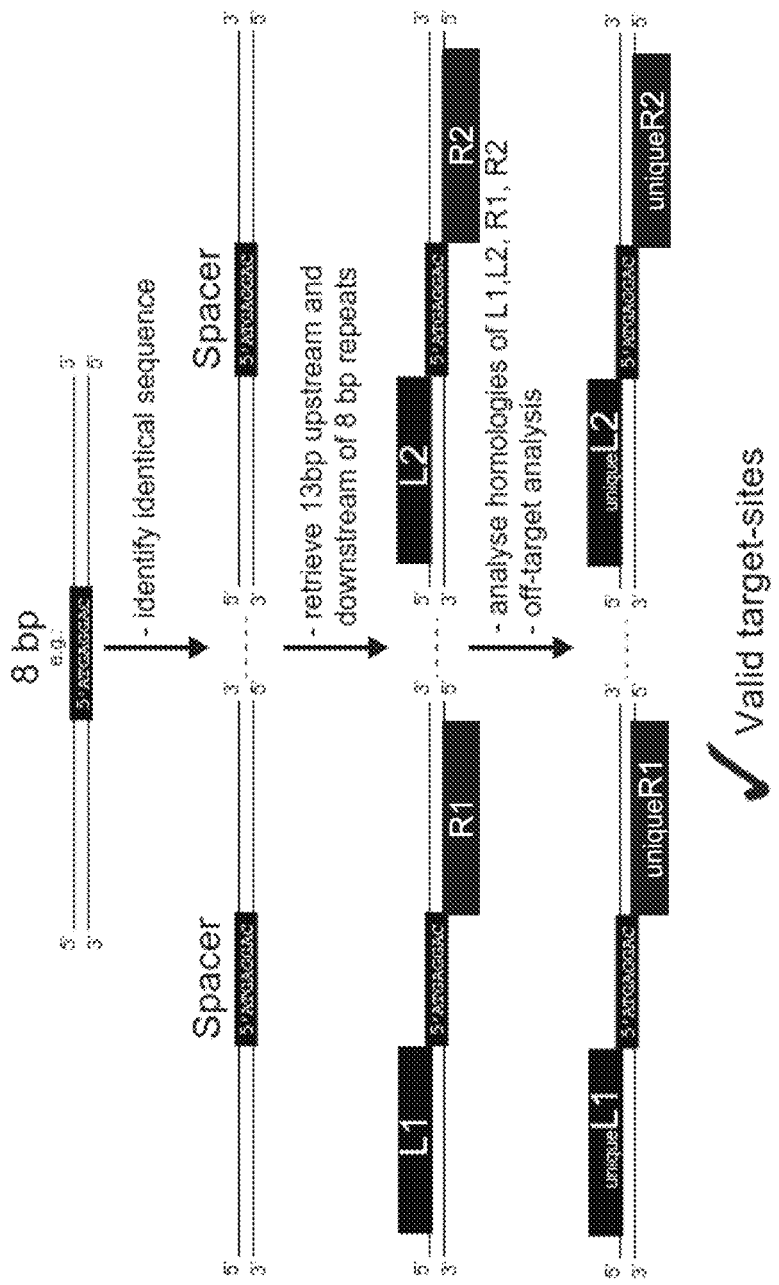
FIG. 18 shows a general scheme of the method of the invention, exemplified by the DRiGD method and steps of the invention.

On the next day the plasmid DNA was isolated from the culture, and 1000 ng of DNA was digested with 1 µl of each NdeI, AvrII, PspXI (restriction enzymes R1, R2 and R3—s. FIGS. 14 and 15) and the exonuclease RecBCD. The recombinase libraries were amplified by error-prone PCR using primers P3 and P4 (SEQ ID No. 32 and 33) and the PCR products were purified on a column and subjected to a digest with the restriction enzymes SacI and SbfI. The isolated recombinase libraries were then ligated back into pF9 (source) and transformed into electrocompetent *E. coli* XL1-Blue cells carrying pDonor-ex8. The transformed cells were grown in 100 ml LB medium containing 15 µg/ml chloramphenicol, 5 µg/ml kanamycin and 1-200 µg/ml L-arabinose and the next cycle thus began. Every three cycles DNA shuffling was carried out as described before (Buchholz and Stewart, 2001). Eleven rounds of SLIDE DRIGR (s. FIG. 14) were performed to enrich for recombinases that can efficiently carry out DRIGR on the target sites loxF9a and LoxF9b without antibiotic selection and without separating integration from resolution of the donor vector.

Primers Used:

| Name | Sequence | SEQ ID No. |
|---|---|---|
| P1# | CGGCGTCACACTTTGCTATG | 30 |
| P2# | CCCTTAAACGCCTGGTGCTA | 31 |

-continued

| Name | Sequence | SEQ ID No. |
|---|---|---|
| P3 | AAGATTAGCGGATCCTACCT | 32 |
| P4 | GTGATTAGTTAGTGAGAGGC | 33 |

By this method the sequences of the following recombinase monomers were obtained: R#1 (SEQ ID No. 34) after step 1,: R#7-B5 (SEQ ID No. 35) after step 2 and Rec F9-3 (SEQ ID No. 36) after the final step 3.

The recombinase efficiency (DRGR efficiency) of the recombinases obtained after step 1, 2 and 3 are compared in the following table:

| Step | Selection scheme | Example Recombinase obtained | SEQ ID No. | DRIGR efficiency |
|---|---|---|---|---|
| 1 | SLIDE (s. FIG. 8) | R#1 | 34 | 0.5% |
| 2 | Duo-SLIDE DRIGR (s. FIG. 9) | R#7-B5: | 35 | 12.3% |
| 3 | SLIDE-DIGR 2.0 (s. FIG. 14) | F9-3 | 36 | 90% |

EXAMPLE 4

To utilize the F9 recombinases in a therapeutic setting, both F9-1 and F9-2 coding sequences are cloned into a delivery vector (such as an adeno-associated viral vector) together with the donor sequence that contains loxF9a and loxF9a flanking the wild-type, or Padua mutation (R338L) of exon 8 of the F9 gene. Delivery of such a vector into target cells in multiple copies replaces the inactivating mutation in the genome (s. FIG. 11).

EXAMPLE 5

To demonstrate the utility of DRiGD recombinases for the excision of a specific DNA sequence on chromosome 7 of the human genome were evolved.

First, two different recombinases libraries were evolved using the described protocol of substrate linked directed evolution (Buchholz and Stewart, 2001 and WO 2002044409 A2—s. FIG. 8). The libraries were evolved against the left or the right half-site (HexL or HexR) of the final target sites Hex1 and Hex2 (s. FIG. 21A). To evolve the recombinase libraries for HexR, two intermediated target sites (HexR1 and HexR2) were used (s. FIG. 21B). Throughout the evolution process new mutations were introduced with error-prone PCR (using Primers P1# and P2#) and DNA-shuffling and selective pressure was further regulated via the expression level of the recombinases. Active recombinases were selected by their ability to recombine the respective target site to delete the sequence flanked by the target sites from the vector (s. FIG. 8—Standard SLiPE and FIG. 21B).

Next, both libraries (obtained on HexR and HexL) were combined in order to recombine the final target sites Hex1 and Hex2. Therefore, the libraries (library size was bigger than 100.000 recombinases) were cloned into the same expression plasmid and were co-expressed from a shared inducible promoter in an operon-like structure, which transcriptionally links both enzymes together (s. FIG. 6 pDUO-SLiDE DRiGD). The plasmids carrying both libraries were then transformed into XL-1 blue *E. coli* cells. After recovering the cells in 1 ml of SOC medium for one hour, 10 μl was plated on a LB agar plate with 15 μg/ml chloramphenicol. The next day 32 clones were picked and cultured in 500 μl of LB with 25 μg/ml chloramphenicol for 8 h. Next, 250 μl pre-culture was used to inoculate 2×5 ml of LB with 25 μg/ml chloramphenicol. In one of the 5 ml cultures 10 μg/ml L-arabinose was added to induce the expression of the recombinase dimer. The next day plasmid DNA was isolated and digested with SacI (R2) and SbfI (R3) to estimate the recombination efficiency in the induced and uninduced sample.

With this method two recombinase dimers (Clone#7 and Clone#30) were obtained that can carry out the excision reaction at high efficiency. The precise excision was confirmed by sequencing the recombined pDUO-SLiDE DRiGD—s. FIG. 22.

The target sites and the intermediate target sites and primers used are listed in the following table:

| Hex target sites | | SEQ-ID |
|---|---|---|
| Hex1 | TACACAGTGTATATTGATTTTTATCAAATGCCTT | 40 |
| Hex2 | TACACAATGTATATTGATTTTTATCAAATGCCTT | 41 |
| HexL | TACACAGTGTATATTGATTTTTATACATTGTGTA | 42 |
| HexR | AAGGCATTTGATATTGATTTTTATCAAATGCCTT | 43 |
| HexR1 | AAGACATTTTATATTGATTTTTATAAAATGTCTT | 44 |
| HexR2 | AACGCATTGGATATTGATTTTTATCCAATGCGTT | 45 |

| Hex target sites | | SEQ-ID |
|---|---|---|
| P1# | CGGCGTCACACTTTGCTATG | 30 |
| P2# | AAGGGAATAAGGGCGACACG | 31 |

By this method the sequences of the following pairs of recombinase monomers were obtained:
Hex-R-#7: SEQ ID No. 46 and Hex-L-#7: SEQ ID No. 47
Hex-R-#30: SEQ ID No. 48 and Hex-L-#30: SEQ ID No. 49

CITED NON-PATENT LITERATURE

Buchholz, F., & Stewart, A. F. (2001). Alteration of Cre recombinase site specificity by substrate-linked protein evolution. Nature Biotechnology, 19(11), 1047-1052.

Karpinski J, Hauber I, Chemnitz J, et al. (2016). Directed evolution of a recombinase that excises the provirus of most HIV-1 primary isolates with high specificity. Nat Biotechnol 34(4):401-9.

Sambrook, J., & Russell, D. W. (2001). Molecular Cloning: A Laboratory Manual, (3rd edition).

Surendranath, V. et al. (2010). SeLOX—a locus of recombination site search tool for the detection and directed evolution of site-specific recombination systems. Nucleic Acids Res. 2010, 38(W293-W298)

Wang M et al. (2016). Efficient delivery of genome-editing proteins using bioreducible lipid nanoparticles. PNAS 113:2868-2873.

Zhang, C et al. (2015) Redesign of the monomer-monomer interface of Cre recombinase yields an obligate heterotetrameric complex. Nucleic Acids Res. 2015, 43 (18): 9076-9085.

The invention claimed is:

1. A DNA-recombining enzyme monomer, comprising the amino acid sequence according to SEQ ID NO: 1 (Rec F9-1) or an amino acid sequence with a least 95% sequence identity to SEQ ID NO: 1.

2. The DNA-recombining enzyme monomer of claim 1, comprising the amino acid sequence according to any one of SEQ ID NOs: 3, 5, 28, and 29.

3. A pharmaceutical composition comprising the DNA-recombining enzyme of claim 1.

4. A DNA-recombining enzyme monomer, comprising the amino acid sequence according of SEQ ID NO: 2 (Rec F9-2) or an amino acid sequence with a least 95% sequence identity to SEQ ID NO:2.

5. The DNA-recombining enzyme monomer of claim 4, comprising the amino acid sequence according to SEQ ID NO: 2 or SEQ ID NO: 4.

6. A pharmaceutical composition comprising the DNA-recombining enzyme of claim 4.

7. A DNA-recombining enzyme dimer comprising two of the DNA-recombining enzyme monomers of claim 1.

8. A DNA-recombining enzyme dimer comprising two of the DNA-recombining enzyme monomers of claim 4.

9. A DNA-recombining enzyme dimer comprising two DNA-recombining enzyme monomers: a first monomer comprising the DNA-recombining enzyme monomer comprising the amino acid sequence according of SEQ ID NO: 1 (Rec F9-1) or an amino acid sequence with a least 95% sequence identity to SEQ ID NO:1; and a second monomer comprising the DNA-recombining enzyme monomer comprising the amino acid sequence according of SEQ ID NO: 2 (Rec F9-2) or an amino acid sequence with a least 95% sequence identity to SEQ ID NO:2.

10. A pharmaceutical composition comprising the DNA-recombining enzyme of claim 7.

11. A pharmaceutical composition comprising the DNA-recombining enzyme of claim 8.

12. A pharmaceutical composition comprising the DNA-recombining enzyme of claim 9.

* * * * *

UNITED STATES PATENT AND TRADEMARK OFFICE
CERTIFICATE OF CORRECTION

| | | |
|---|---|---|
| PATENT NO. | : 11,845,954 B2 | Page 1 of 1 |
| APPLICATION NO. | : 16/622937 | |
| DATED | : December 19, 2023 | |
| INVENTOR(S) | : Buchholz et al. | |

It is certified that error appears in the above-identified patent and that said Letters Patent is hereby corrected as shown below:

In the Claims

Column 135, Line 2, Claim 4, delete "of" and insert --to--.

Column 135, Line 17, Claim 9, delete "of" and insert --to--.

Column 135, Line 22, Claim 9, delete "of" and insert --to--.

Signed and Sealed this
Twentieth Day of February, 2024

*Katherine Kelly Vidal*

Katherine Kelly Vidal
*Director of the United States Patent and Trademark Office*